United States Patent [19]
Oppenheim et al.

[11] Patent Number: 5,759,816
[45] Date of Patent: *Jun. 2, 1998

[54] EXPRESSION VECTORS CONTAINING λP$_L$ PROMOTER AND T$_1$T$_2$ RRNA TERMINATION SEQUENCE PLASMIDS CONTAINING THE VECTORS HOSTS CONTAINING THE PLASMIDS AND RELATED METHODS

[75] Inventors: Amos B. Oppenheim, Jerusalem; Avigdor Levanon, Netanya; Hilla Locker-Giladi, Jerusalem; Marian Gorecki; Tikva Vogel, both of Rehovot, all of Israel

[73] Assignee: Bio-Technology General Corp., New York, N.Y.

[ * ] Notice: The term of this patent shall not extend beyond the expiration date of Pat. No. 5,112,744.

[21] Appl. No.: 450,014

[22] Filed: May 25, 1995

Related U.S. Application Data

[63] Continuation of Ser. No. 89,903, Jul. 12, 1993, abandoned, which is a continuation of Ser. No. 873,573, Apr. 21, 1992, abandoned, which is a continuation of Ser. No. 464,616, Jan. 3, 1990, abandoned, which is a continuation of Ser. No. 896,750, Aug. 14, 1986, abandoned, which is a continuation-in-part of Ser. No. 644,671, Aug. 27, 1984, abandoned.

[51] Int. Cl.[6] .............. C12P 21/02; C12N 1/21; C12N 15/63; C12N 15/70
[52] U.S. Cl. .............. 435/69.4; 435/252.33; 435/320.1
[58] Field of Search .............. 435/320.1, 252.33, 435/69.4

[56] References Cited

U.S. PATENT DOCUMENTS

| | | | |
|---|---|---|---|
| 4,363,877 | 12/1982 | Goodman et al. | 435/320.1 |
| 4,436,815 | 3/1984 | Hershberger et al. | 435/34 |
| 4,512,922 | 4/1985 | Jones et al. | 260/112 R |

(List continued on next page.)

FOREIGN PATENT DOCUMENTS

| | | | |
|---|---|---|---|
| 49619 | 10/1980 | European Pat. Off. | C12N 15/00 |
| 41767 | 12/1981 | European Pat. Off. | C12N 15/00 |
| 0104920 | 9/1983 | European Pat. Off. | |
| 138111 | 10/1983 | European Pat. Off. | C12N 9/02 |
| 0131843 | 1/1985 | European Pat. Off. | C12N 15/00 |
| 8401150 | 3/1984 | WIPO | |
| 8402918 | 8/1984 | WIPO | |

OTHER PUBLICATIONS

Remaut, E. et al., Gene 15: 81–93 (1981).
Derynck, R. et al., Nature 287: 193–197 (1980).
Oppenheim, A.B. et al., J. Mol. Biol. 158: 327–346 (1982).

(List continued on next page.)

*Primary Examiner*—Nancy Degen
*Attorney, Agent, or Firm*—John P. White

[57] ABSTRACT

An improved vector upon introduction into a suitable host containing the thermolabile repressor $C_I$ renders the host capable of effecting expression of a desired gene. The vector is a double-stranded DNA molecule which includes in 5' to 3' order the following: the promoter and operator $P_LO_L$ from lambda bacteriophage; the N utilization site; a first restriction enzyme site permitting replacement of the ribosomal binding site which follows thereafter; a ribosomal binding site; an ATG initiation codon or DNA which is converted into an ATG initiation codon upon insertion of the desired gene into the vector; a second restriction enzyme site for inserting the gene in phase with the ATG codon; a $T_1T_2$ rRNA transcription termination sequence; an origin of replication and a gene associated with a selectable or identifiable phenotypic trait manifested when the vector is present in the host. The distance between the 3' end of the $P_LO_L$ promoter and operator sequence and the 5' end of the N utilization site is less than about 80 base pairs and the distance between the 3' end of the N utilization site and the 5' end of the ribosomal binding site is less than about 300 base pairs. Plasmids have been constructed from the vectors and used to produce bovine, chicken and porcine growth hormones, human apolipoprotein E and human superoxide dismutase.

3 Claims, 51 Drawing Sheets

U.S. PATENT DOCUMENTS

| | | | |
|---|---|---|---|
| 4,559,300 | 12/1985 | Kovacevic et al. | 435/68 |
| 4,578,355 | 3/1986 | Rosenberg | 435/317 |
| 4,637,980 | 1/1987 | Auerbach et al. | 435/252.33 |
| 4,650,761 | 3/1987 | Hershberger et al. | 435/34 |
| 4,670,393 | 6/1987 | Seeburg | 435/240 |
| 4,710,473 | 12/1987 | Morris | 435/172.3 |
| 5,112,744 | 5/1992 | Oppenheim et al. | 435/189 |
| 5,126,252 | 6/1992 | Oppenheim et al. | 435/69.4 |
| 5,143,836 | 9/1992 | Hartman et al. | 435/189 |
| 5,162,217 | 11/1992 | Hartman et al. | 435/189 |
| 5,198,361 | 3/1993 | Aviv et al. | 435/252.33 |
| 5,256,546 | 10/1993 | Aviv et al. | 435/69.4 |

OTHER PUBLICATIONS

Shimatake, H. et al., Nature 292: 128–132 (1981).
Courtney, M. et al., Proc. Natl. Acad. Sci. (USA) 81: 669–673 (1984).
Lautenberger, J.A. et al., Gene 23: 75–84 (1983).
Lautenberger, J.A. et al., Science 221: 858–860 (1983).
Shatzman, A.R. et al., 14 Miami Winter Symposium, abstract p. 98 (1982).
Amann, E. et al., Gene 25: 167–178 (1983).
Gelfand, D.H. et al., Proc. Natl. Acad. Sci. (USA) 75: 5869–5873 (1978).
Zabeau, M. et al., The EMBO Journal 10: 1217–1224 (1982).
Gentz, R. et al., Proc. Natl. Acad. Sci. USA 78(8) 4936–4940 (1981).
Spence, C.A. et al., Amer. Soc. of Animal Science, abstract (University of Missouri, Aug. 7–10, 1984).
Muesing et al., Cell 24:235–242 (1981) (Exhibit 7).
Seeburg et al., DNA 2(1):37–45 (1983) (Exhibit 8).
Souza et al., J. Exp. Zool. 232(3):465–474 (1984) (Exhibit 9).
Souza et al., J. Ce., Biochem., abstract 1070:85 (1984) (Exhibit 10).
Proudman, Proc. Soc. Exp. Biol. Med. 175(4):417–419 (1984) (Exhibit 11).
Hedgpeth et al., Mol. Gen. Genet. 163:197–203 (1978) (Exhibit 12).
Maniatis et al., In Molecular Cloning, A Laboratory Manual, Cold Spring Harbor, pp. 411–413 and 418–419 (1982) (Exhibit 13).
DeBoer et al., DNA 2(3):231–235 (1983) (Exhibit 14).
Backman et al., Cell 13:65–71 (1978) (Exhibit 15).
Guarante et al., Cell 20:543–553 (1980) (Exhibit 16).
Guarante et al., Science 209:1428–1430 (1980) (Exhibit 17).
Rosenberg et al., Methods in Enzymology 101:123–138 (1983) (Exhibit 18).
Glaser et al., Nature 302:74–76 (1983) (Exhibit 19).
Nilsson et al., Nucleic Acids REs. 11(22):8019–8030 (1983) (Exhibit 20).
Sarmientos et al., Cell 32:1337–1346 (1983) (Exhibit 21).
Williams et al., Virology 29:555–575 (1979) (Exhibit 22).
Watson et al., Recombinant DNA, A Short Course, W.H. Freeman and Company, New York (1983) (Exhibit 23).
Bernard, H.V. et al., Gene 5: 59–76 (1979).
Derom, C. et al., Gene 17: 45–54 (1982).
Gheysen, D. et al., Gene 17: 55–63 (1982).
Eppard, P.J. et al., Proceeding of 1984 Cornell Nutrition Conference for Feed Manufacturers, pp. 5–12.
Chapon (1982) EMBO J vol. 1(3):369–374.
Warburton et al. (1983), NAR, vol. 11(17)5837–5854.
Brosius (1984), Gene, vol. 27, pp. 161–172.
Brosius et al (1981), JMB, vol. 148, pp. 107–127.
Stueber et al (1982), EMBO J., vol. 1(11), pp. 1399–1404.
ATCC Recombinant DNA materials, host notes p. 116.
Holmes et al Cell 32:1029–23, 1983.

1. Partial NdeI
2. Fill in
3. Ligase

*In each case a different primer was used, see Table VIII

1. StuI
2. Self Ligation

1. NdeI
2. Isolate large fragment

T4 DNA Ligase

EXPRESSION VECTORS CONTAINING λP_L PROMOTER AND T₁T₂ RRNA TERMINATION SEQUENCE PLASMIDS CONTAINING THE VECTORS HOSTS CONTAINING THE PLASMIDS AND RELATED METHODS

This application is a continuation of U.S. Ser. No. 08/089,903, filed Jul. 12, 1993, now abandoned; which is a continuation of U.S. Ser. No. 07/873,573, filed Apr. 21, 1992, now abandoned; which is a continuation of U.S. Ser. No. 07/464,616, filed Jan. 3, 1990, now abandoned; which was a continuation of U.S. Ser. No. 06/896,750, filed Aug. 14, 1986, now abandoned; which was a continuation-in-part of U.S. Ser. No. 06/644,671, filed Aug. 27, 1984, now abandoned.

BACKGROUND OF THE INVENTION

One aspect of genetic engineering involves the insertion of foreign DNA sequences derived from eucaryotic sources into *Escherichia coli* or other microorganisms. A further refinement of genetic engineering concerns inducing the resulting microorganism to produce polypeptides encoded by the foreign DNA. Production of polypeptides can be considered a two-step process, with each step including numerous substeps. The two steps are transcription and translation. To produce a polypeptide efficiently and in quantity both steps of the process must be efficient. Transcription is the production of mRNA from the gene (DNA). Translation is the production of polypeptide from the mRNA.

A critical substep of the transcription process is initiation, that is, the binding of RNA polymerase to a promoter-operator region. The sequence of deoxyribonucleotide bases which make up the promoter region may vary and thereby affect the relative efficiency of the promoter. The efficiency depends on the affinity of the RNA polymerase for the promoter.

The efficiency of translation is affected by the stability of the mRNA. Increased stability of the mRNA permits improved translation. Although the exact determinants of mRNA stability are not precisely known, it is known that mRNA secondary structure as determined by the sequence of its bases has a role in stability.

The initial substep of translation involves binding of the ribosome to a base sequence on the MRNA known as the Shine-Dalgarno sequence or the ribosomal binding site (RBS). The synthesis of polypeptides begins when the ribosome migrates along the mRNA to the AUG start codon for translation. Generally these codons are found approximately 10 bases "downstream" from the Shine-Dalgarno site. Factors which increase the efficiency of translation include those which enhance binding of the ribosomes to the ShineDalgarno site. It has been shown that the structure of the MRNA in the region of the Shine-Dalgarno sequence and the AUG codon and the distance between the Shine-Dalgarno sequence and the AUG codon each play a critical role in determining the efficiency of translation. Other factors which affect the efficiency of translation are premature termination and attenuation. Efficiency of translation can be improved by removing the attenuation sites.

A difficulty encountered in attempts to produce high amounts of eucaryotic polypeptides in bacterial cells involves the inability of cells producing large amounts of mRNA to grow efficiently. This difficulty can be eliminated by preventing transcription by a process known as repression. In repression genes are switched off due to the action of a protein inhibitor (repressor protein) which prevents transcription by binding to the operator region. After microorganisms have grown to desired cell densities, the repressed genes are activated by destruction of the repressor or by addition of molecules known as inducers which overcome the effect of the repressor.

Numerous reports may be found in the literature concerning the cloning of eucaryotic genes in plasmids containing the PL promoter from λ bacteriophage. (Bernard, H.V., et al., Gene (1979) 5, 59; Derom, C., et al., Gene (1982) 17, 45; Gheysen, D., et al., Gene (1982) 17, 55; Hedgpeth, J., et al., Mol. Gen. Genet. (1978) 163, 197; Remaut, E., et al., (1981) Gene 15, 81 and Derynck, R., et al., Nature (1980) 287, 193). In addition, European Patent Application No. 041,767, published Dec. 16, 1981, describes expression vectors containing the $P_L$ promoter from λbacteriophage. However, none of these references describe the use of the $C_{II}$ ribosomal binding site.

The use of a vector containing the $P_L$ promoter from λbacteriophage and the $C_{II}$ ribosomal binding site has been described. (Oppenheim, A.B., et al., J. Mol. Biol. (1982) 158, 327 and Shimatake, H. and Rosenberg, M., Nature (1981) 292, 128.) These publications describe the production of increased levels of $C_{II}$ protein but do not involve or describe the production of eucaryotic proteins.

Other vectors which contain the λ$P_L$ promoter and the $C_{II}$ ribosomal binding site have also been described (Courtney, M., et al., PNAS (1984) 81, 669–673; Lautenberger, J.A., et al., Gene (1983) 23, 75–84 and Lautenberger, J.A., et al., Science (1983) 221, 858–860). However, all of these vectors lead to the production of fused proteins which contain the amino terminal portion of the $C_{II}$ protein.

In 1982 Shatzman and Rosenberg presented a poster at the 14th Miami Winter Symposium (Shatzman, A.R. and Rosenberg, M., 14 Miami Winter Symposium, abstract p98 [1982]). This abstract provides a non-enabling disclosure of the use of a vector containing $P_L$ from λbacteriophage, Nut and the $C_{II}$ ribosomal binding site to synthesize a "eucaryotic" polypeptide (SV40 small T antigen is actually not a eucaryotic polypeptide but a viral protein) in an amount greater than 5% of the cell protein in an unnamed bacterial host. The operator used is not defined. Neither an origin of replication nor a gene for a selectable phenotype is identified. This system with which the vector is used is described as including certain host lysogens into which the vector can be stably transformed.

Applicants are aware of the existence of a pending U.S. patent application in the name of M. Rosenberg filed under Ser. No. 06/457,352 now U.S. Pat. No. 4,578,355, by the National Institutes of Health, Dept. of Health and Human Services, U.S.A. Portions of this application have been obtained from the National Technical Information Service, U.S. Dept. of Commerce. However, the claims are not available and are maintained in confidence. The available portions of the application have been reviewed. This disclosure is not enabling. It indicates that the host is important (p8, line 17) but fails to identify any suitable host. It further depends upon the use of a X mutant which is not specified (p4, line 20). It indicates that the host contains lysogens (p8, line 18) unlike the present invention in which the host is not lysogenic. It mentions cloning and expression of a eucaryotic gene, monkey metallothionein gene, (p7, line 18) but does not provide details. It specifies that neither the sequence nor the position of any nucleotide in the $C_{II}$ ribosomal binding region has been altered (p3, line 27).

Pending, co-assigned U.S. patent application Ser. No. 06/514,188, filed Jul. 15, 1983, now abandoned, describes novel vectors useful for the expression of polypeptides in bacteria.

These vectors include $P_LO_L$, N utilization site for binding antiterminator N protein, ribosomal binding site, ATG codon, restriction enzyme site for inserting the gene encoding the desired polypeptide, an origin of replication and a selectable marker. In these vectors the distance between the N utilization site and the ribosomal binding site is greater than about 300 base pairs. In addition, each of these vectors contains a specific ribosomal binding site which cannot be readily replaced. These vectors were not equally useful for expression of different polypeptides.

$T_1T_2$ rRNA transcription termination sequences have been described. (Brosius, J., et al., J. Mol. Biol. 148, 107 (1981)). The placement of $T_1T_2$ rRNA transcription termination sequences at the 3' end of a procaryotic gene and the expression of such gene under the control of a promoter have been described. (Amann, E., et al., Gene (1983) 25, 167; Zabeau, M., et al., The EMBO Journal (1982) 1, 1217).

The present invention relates to expression vectors which unexpectedly provide enhanced expression of different polypeptides. By employing different ribosomal binding sites in the vectors of this invention it is possible to achieve enhanced expression levels of different polypeptides relative to the levels achieved with the previous vectors. In addition, using the same ribosomal binding sites as in the previous vectors, it is possible to achieve enhanced expression of the same polypeptides. Moreover, by placing $T_1T_2$ rRNA transcription termination sequences at the 3' end of the gene encoding a polypeptide whose expression is desired, it is possible to increase the amount of desired polypeptide relative to the total polypeptide produced by a bacterial host.

Bovine growth hormone (bGH), porcine growth hormone, chicken growth hormone, human growth hormone (hGH), superoxide dismutase (SOD), human apolipoprotein E and analogs thereof are some of several polypeptides which may be produced using the novel expression vectors of this invention.

The present invention relates in particular to expression plasmids which unexpectedly provide enhanced expression of bovine growth hormone, porcine growth hormone, human growth hormone, human apolipoprotein E and analogs thereof using the same ribosomal binding sites as in the previous vectors and by employing different ribosomal binding sites as described in this invention.

The present invention also relates to methods for enhanced production of these polypeptides or analogs thereof in bacteria, including prototrophic and lytic bacterial hosts, utilizing these plasmids.

The invention is also directed to expression vectors, plasmids and methods for producing mutant analogs of human apolipoprotein E.

This invention also includes methods of increasing milk production in pregnant sows and preventing the death of suckling piglets by administering porcine growth hormone or analogs thereof to pregnant sows.

SUMMARY OF THE INVENTION

This invention concerns an improved expression vector which upon introduction into a suitable bacterial host cell, e.g., *Escherichia coli*, containing the thermolabile repressor $C_I$ renders the host cell capable, upon increasing the temperature of the host cell to a temperature at which the repressor is inactivated, of effecting expression of a desired gene inserted into the vector and production of the polypeptide encoded by the gene comprising:

a double-stranded DNA molecule which includes in 5' to 3' order the following:

a DNA sequence which contains the promoter and operator $P_LO_L$ from lambda bacteriophage;

the N utilization site for binding antiterminator N protein;

a first restriction enzyme site permitting replacement of the DNA sequence containing the ribosomal binding site which follows thereafter;

a DNA sequence which contains a ribosomal binding site for rendering the mRNA of the desired gene capable of binding to ribosomes within the host cell;

an ATG initiation codon or a DNA sequence which is converted into an ATG initiation codon upon insertion of the desired gene into the vector;

a second restriction enzyme site for inserting the desired gene into the vector in phase with the ATG initiation codon; and a DNA sequence which contains a $T_1T_2$ rRNA sequence;

and which additionally includes a DNA sequence which contains an origin of replication from a bacterial plasmid capable of autonomous replication in the host cell and a DNA sequence which contains a gene associated with a selectable or identifiable phenotypic trait which is manifested when the vector is present in the host cell, the distance between the 3' end of the $P_LO_L$ promoter and operator sequence and the 5' end of the N utilization site being less than about 80 base pairs and the distance between the 3' end of the N utilization site and the 5' end of the ribosomal binding site being less than about 300 base pairs. Desirably, the $T_1T_2$ rRNA termination sequence is less than about 100 base pairs from the 3' end of the second restriction enzyme site, more desirably it is less than about 20 base pairs from the 3' end of the site. The presently preferred vector is p579.

Genes, e.g., cDNAs, encoding desired polypeptides, such as growth hormones, e.g., bovine, porcine, chicken or human growth hormones, human superoxide dismutase, human apolipoprotein E or analogs thereof, may be inserted into the second restriction enzyme site of the vector to create plasmids. The plasmids in turn can be introduced into suitable hosts where the genes can be expressed and the desired polypeptide produced. The presently preferred plasmids are: for bovine growth hormone (bGH), p9200; for porcine growth hormone (pGH), pAs 575; for human growth hormone (hGH), pTV300; for human apolipoprotein E (ApoE), pTV-264-45; pTVR 279-8; pTHR 315-18; pTVR 298-34; pTHR 530-40; pTHR 531-6II; pTHR 532-18; pTHR 533-4; pTHR 299-40; pTHR 526-6; pTHR 324-20; pTHR 501; pTHR 514-7; pTHR 520-3; pTHR 325-22; pTVR 289-18; pTHR 525-2; pTHR 540-37; pTHR 539-5II. Preferred hosts include auxotrophic, prototrophic or lytic *Escherichia coli*. Preferred prototrophic hosts include *E. coli* A4200, A4255 and biotin independent A4200. A preferred lytic host is A4048.

The resulting host vector systems can be employed to manufacture polypeptides. Host cells containing the plasmids are grown under suitable conditions permitting production of polypeptide and the resulting polypeptide is recovered. Using the host vector systems, analogs of bovine growth hormone, porcine growth hormone, human growth hormone and human apolipoprotein E have been prepared. The porcine growth hormone analogs have been employed to increase the milk produced in lactating sows and prevent the death of suckling piglets.

BRIEF DESCRIPTION OF THE FIGURES

The restriction maps for each of the plasmids shown in FIGS. 1–50 do not identify all restriction sites present on each plasmid. In some cases restriction sites are shown in one figure but not in another. However, in all cases those restriction sites necessary for a complete understanding of the invention are shown.

A plasmid containing bGH CDNA, D4 (ATCC No. 31826), was digested with HaeII. The resulting 1600 base pair large fragment was purified and digested at 37° C. for 5 minutes with S1 exonuclease. A synthetic EcoRI linker with the sequence:

GGAATTCC

CCTTAAGG was attached to the ends of the resulting fragments by ligation. The ligation mixture was cleaved with EcoRI and inserted into pBR322 (ATCC No. 37017) which had been cleaved with EcoRI. A clone, pALRI, was obtained which upon cleavage with EcoRI released a 1200 base pair fragment with the sequence:

AATTCCCAGCCATG ...

GGGTCGGTAC ...

at the 5' end. This sequence demonstrates that PALRI contains an EcoRI restriction site which includes the TTC codon for residue number 1 (phenylalanine) of natural bGH. pALRI was subjected to a partial cleavage with PstI. The digest was treated with DNA- polymerase I large fragment (Klenow) and HindIII linkers with the sequence:

GAAGCTTC

CTTCGAAG were attached by ligation. The ligation mixture was cleaved with EcoRI and HindIII. The fragment containing bGH CDNA was isolated and subcloned into pBR322 between the EcoRI and HindIII restriction sites to give pAL500 (ATCC No. 39782).

Figure 1:
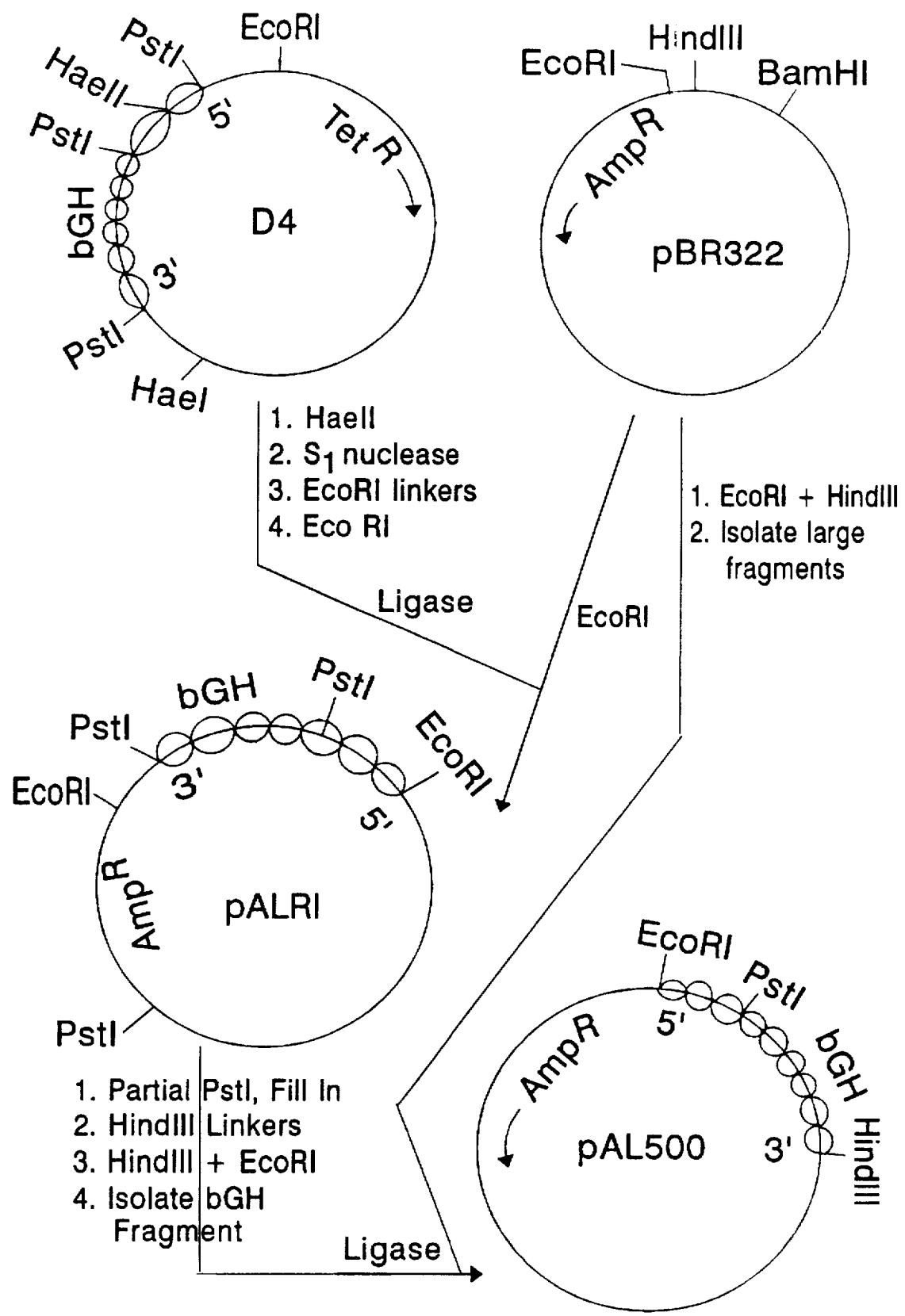
FIG. 1. Construction of pAL500.
Figure 2:
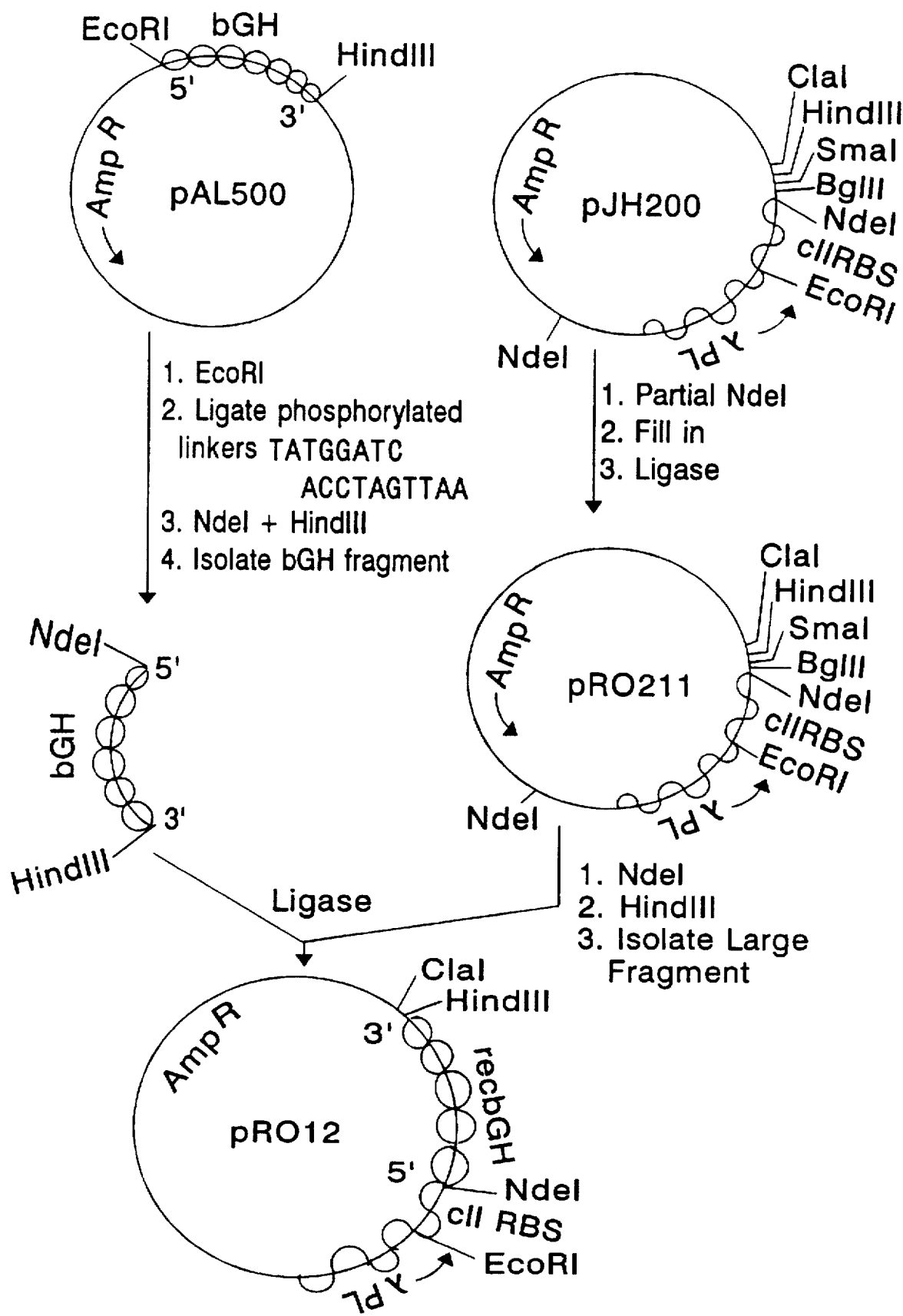

FIG. 2. Construction of pRO211 and pRO12.

The plasmid pJH200 (ATCC No. 39783) was partially digested with NdeI, treated with DNA polymerase I (Klenow) to fill in the ends and the resulting ends were religated to form the expression vector pRO211. The expression vector pRO211 was digested with NdeI and HindIII, the large fragment isolated and ligated to an NdeI-HindIII bGH fragment isolated from pAL500 (ATCC No. 39782) to give pRO12. (The NdeI-HindIII fragment was produced from pAL500 by digesting it with EcoRI and ligating to the ends of the digestion product synthetic linkers with the sequence:

TATGGATC

ACCTAGTTAA

The ligation mixture was digested with NdeI and HindIII and the resulting NdeI-HindIII bGH fragment isolated.)

Figure 3:
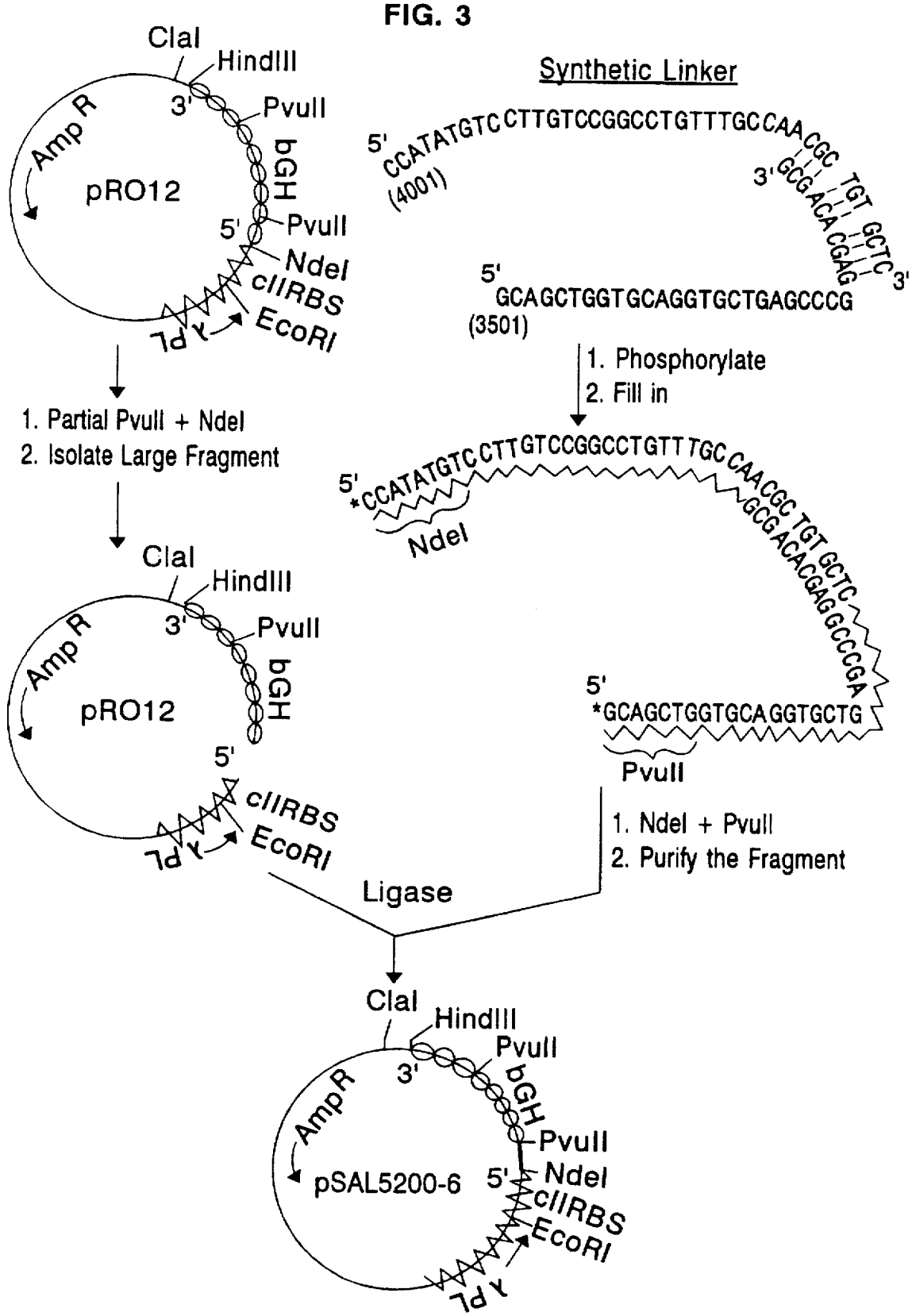

FIG. 3. Construction of pSAL 5200-6 pRO12 (FIG. 2) was partially digested with PvuII followed by digestion with NdeI to eliminate a 72 base pair fragment. A synthetic DNA fragment coding for the first 24 amino acids of the N-terminus of authentic bGH was ligated to the digested pRO12.

The synthetic DNA fragment was constructed by annealing two phosphorylated synthetic single-stranded DNAs of the sequence:

CCATATGTTCCCAGCCATGTCCTTGTC-
CGGCCTGTTTGCCAACGCTGTGCTC-3'

3'-GCGACACGAGGCCCGAGTCGTGGACGTGGTCGACG

The annealed fragment was treated with DNA polymerase I (Klenow) in the presence of all four deoxyribonucleoside triphosphates in order to form the full length double-stranded DNA. The fragment was digested with PvuII and NdeI before ligation to pRO12 to form pSAL 5200-6.

Figure 4:
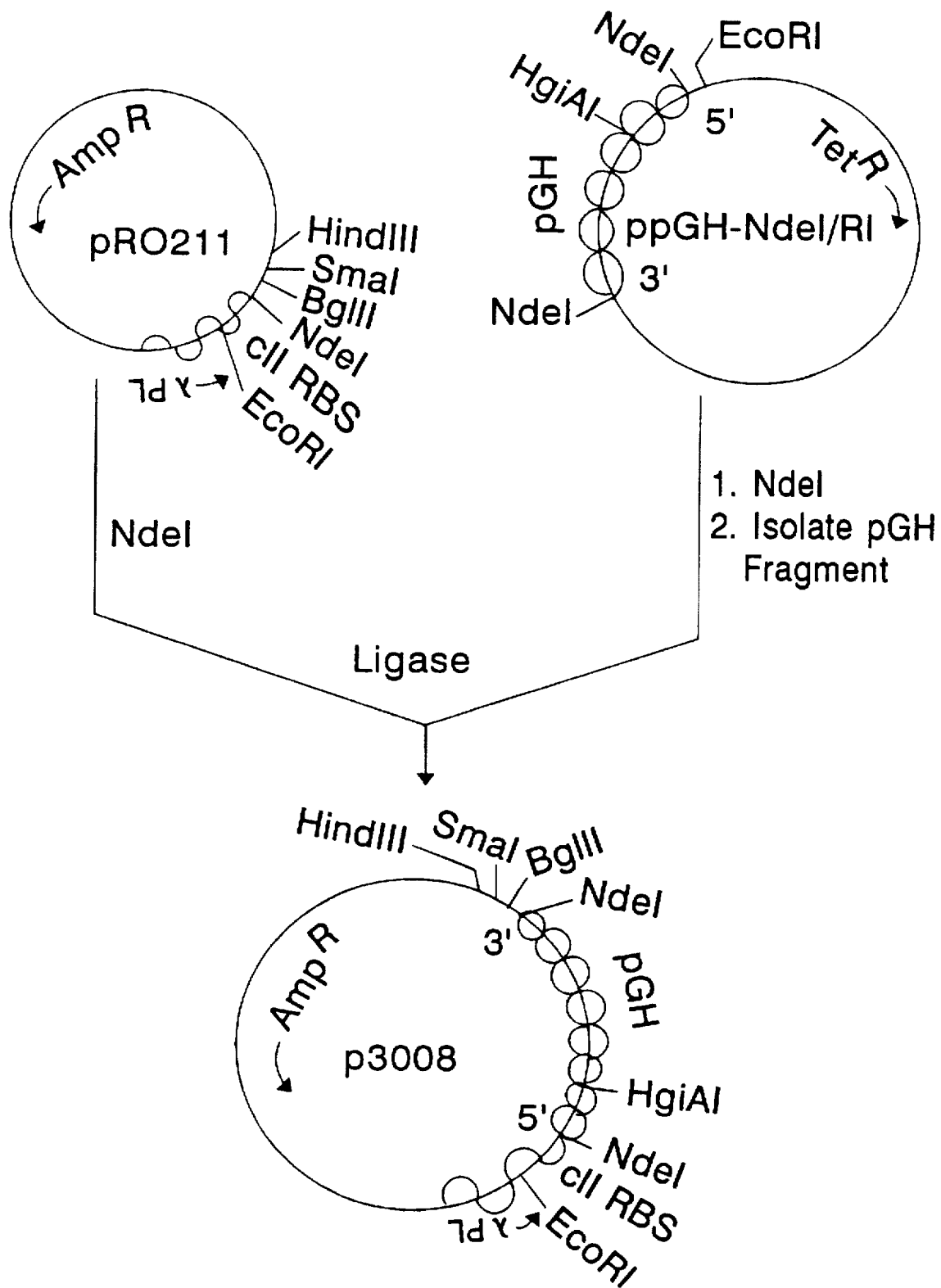

FIG. 4. Construction of p3008.

p3008 (ATCC No.39804) was constructed by ligating NdeI-digested pRO211 (FIG. 2) with the pGH fragment isolated from an NdeI digest of the plasmid ppGH-NdeI/RI.

ppGH-NdeI/RI contains full length pGH cDNA to both ends of which NdeI sites have been added by means of synthetic linkers.

Figure 5:
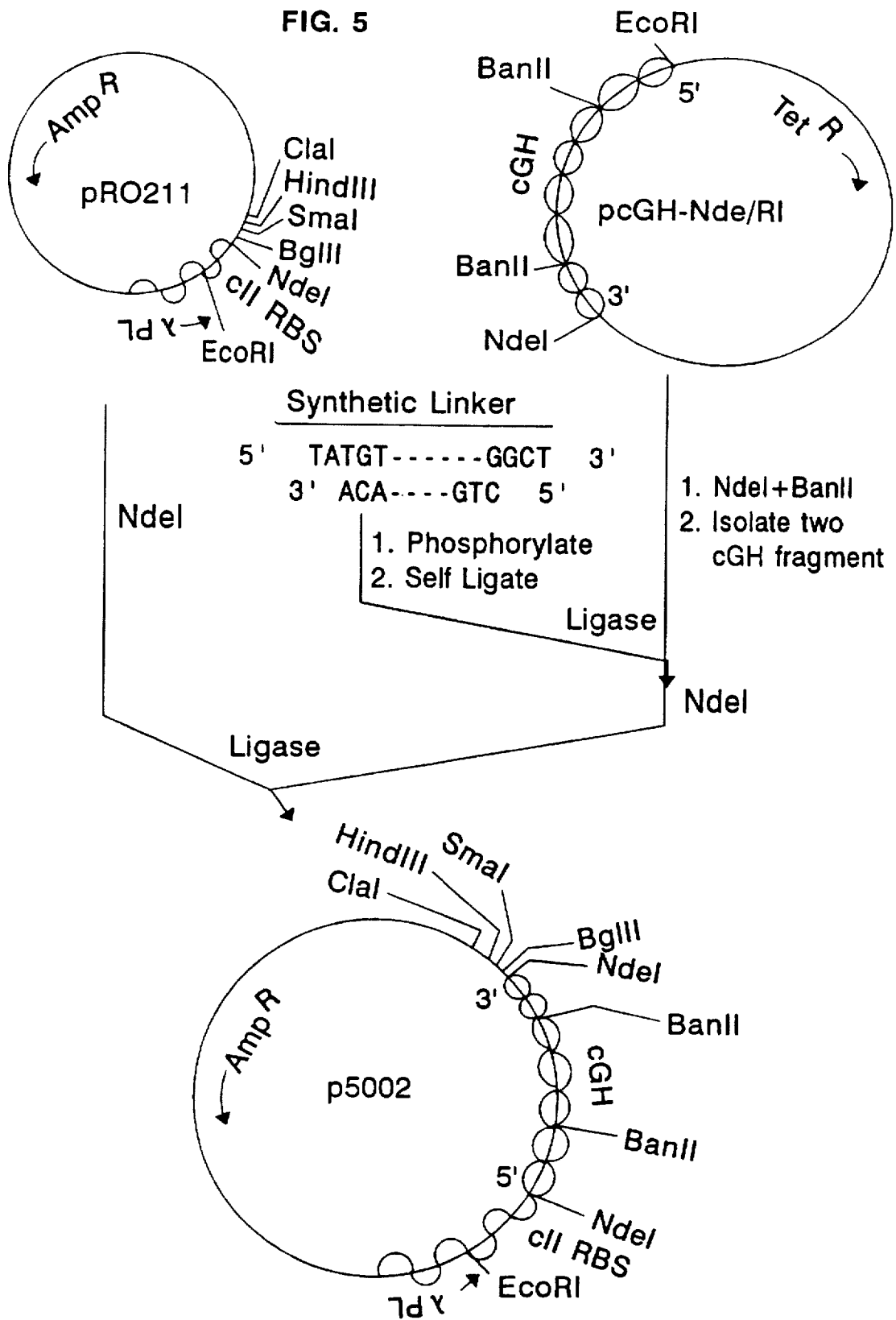

FIG. 5. Construction of p5002.

p5002 was constructed by tripartite ligation of a dimerized synthetic linker and the 2 cGH fragments isolated from an NdeI and BanII digest of the plasmid pcGH-NdeI/RI. The ligation mixture was digested with NdeI and then ligated to the expression vector pRO211 (FIG. 2) after it had been restricted with NdeI. A colony containing the plasmid p5002 was isolated.

The synthetic linker was constructed from two single-stranded synthetic DNAs of the sequence:

TATGTTCCCTGCCATGCCCCTCTCCAAC-
CTGTTTGCCAACGCTGTGCTGAGGGCT

ACAAGGGACGGTACGGGGAGAGGTTGGA-
CAAACGGTTGCGACACGACTC

The linker was phosphorylated before ligation. The linker codes for the first 18 amino acids of the N-terminus of the authentic cGH.

The plasmid pcGH-NdeI/RI contains full length cGH cDNA at the 5' end of which there is an EcoRI restriction site and at the 3' end of which there is an NdeI restriction site. These restriction sites were added by means of synthetic linkers.

Figure 6:
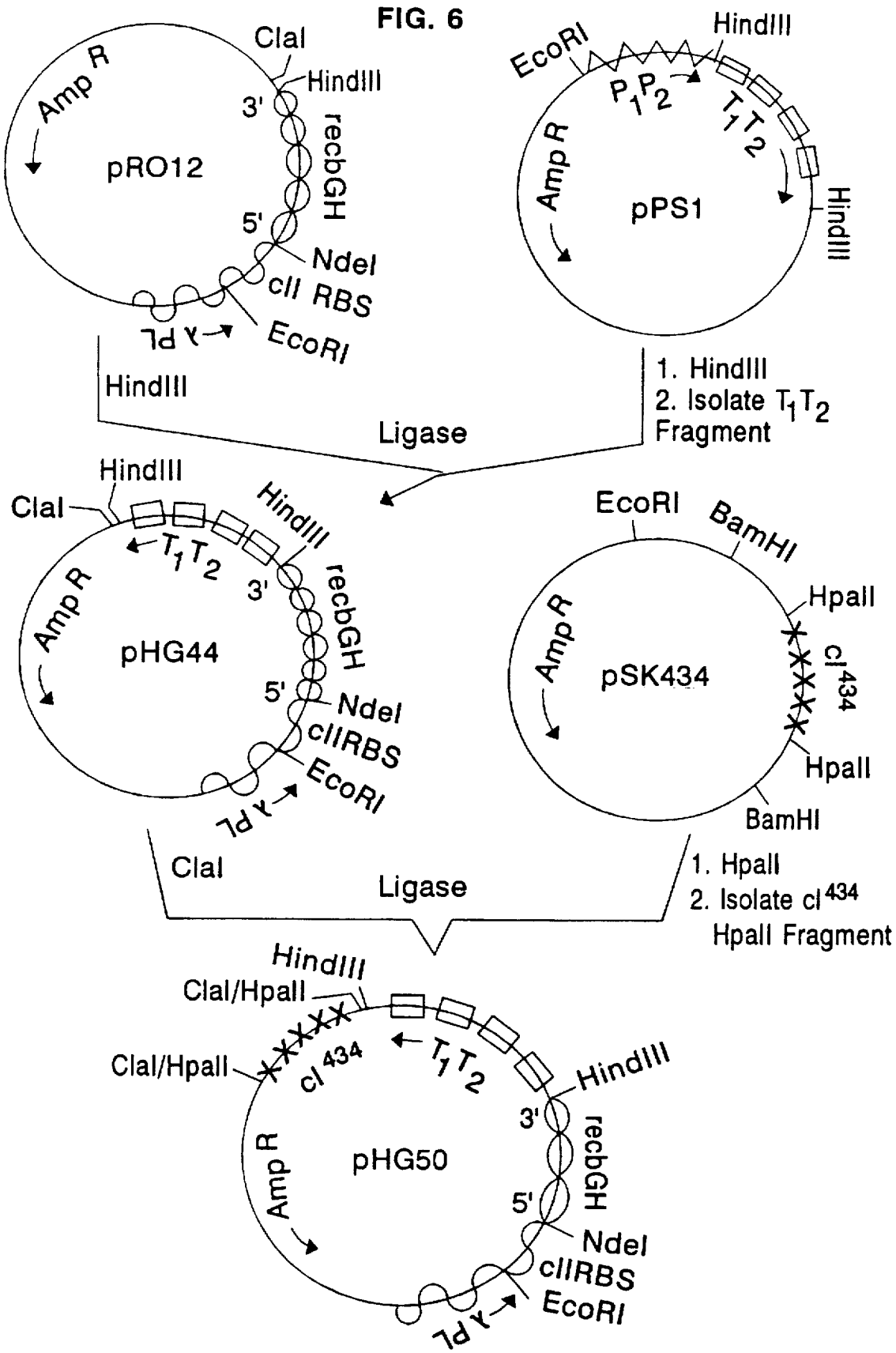

FIG. 6. Construction of pHG44 and pHG50.

pRO12 (FIG. 2) was digested with HindIII. The linear form DNA (form III) was purified from agarose gel and ligated to a HindIII-HindIII fragment of about 1200 base pairs which contains the rRNA operon transcription termination sequences $T_1T_2$. The $T_1T_2$ HindIII-HindIII fragment was isolated from plasmid pPS1 (ATCC No. 39807) which had been digested with HindIII. The resulting plasmid pHG44 (ATCC No. 39806) contains the $T_1T_2$ sequences at the 3' end of the recombinant (rec) bGH sequence.

The plasmid pSK434 (ATCC No. 39784) containing the $\lambda cI^{434}$ repressor sequences was digested with HpaII. The $\lambda cI^{434}$ HpaII-HpaII fragment was isolated and ligated to pHG44 which had been digested with ClaI. The resulting plasmid pHG50 (ATCC No. 39805) contains the $T_1T_2$ transcription termination sequences and the $\lambda cI^{434}$ repressor sequence.

Figure 7:
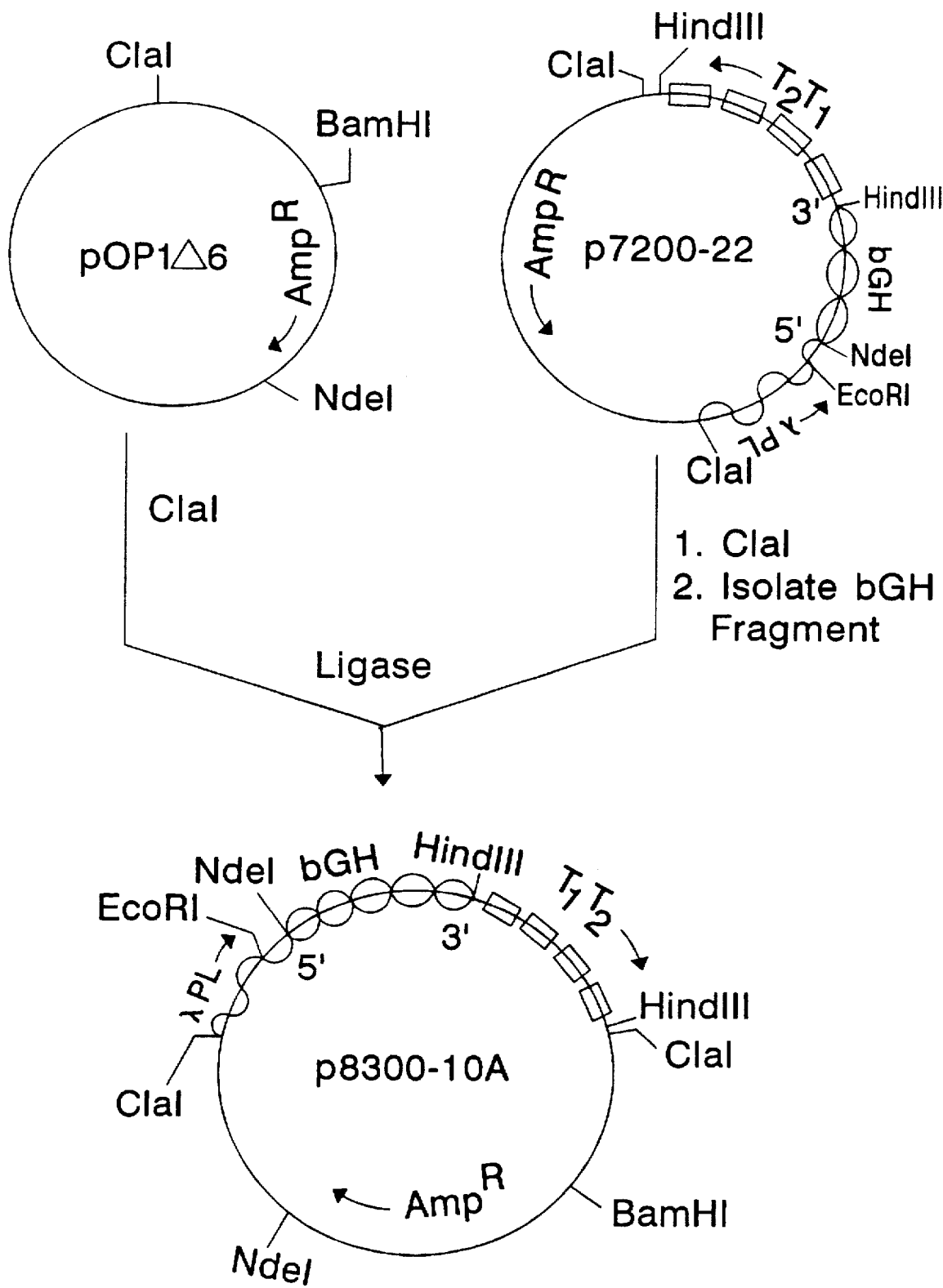

FIG. 7. Construction of p8300-10A.

The plasmid p8300-10A (ATCC No. 39785) which expresses an analog of the natural phenylalanine form of bGH having methionine at the N-terminus (met-phe bGH) was prepared as follows. The plasmid p7200-22 contains the $\lambda P_L$ promoter and ribosomal binding site derived from pJH200 (ATCC No. 39783). DNA encoding met-phe bGH and the $T_1T_2$ rRNA termination sequences. The ClaI-ClaI fragment containing the $\lambda P_L$ promoter, the $C_{II}$ ribosomal binding site, the met-phe bGH gene and the $T_1T_2$ transcription termination sequences was inserted into the unique ClaI site of plasmid pOP1Δ6, a constitutive high copy number plasmid, to form p8300-10A.

Figure 8:
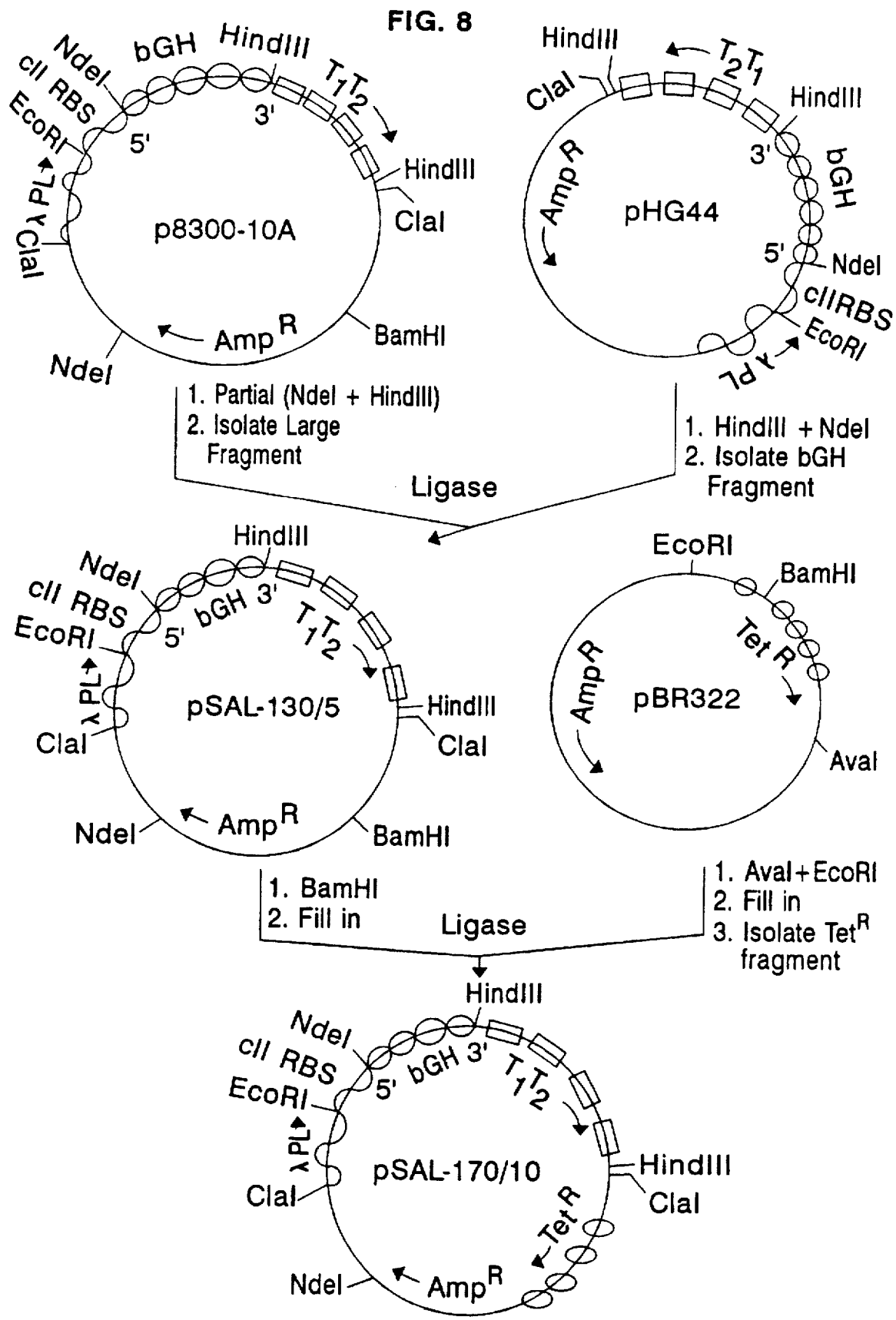

FIG. 8. Construction of pSAL-130/5 and pSAL-170/10.

The plasmid pHG44 (ATCC No. 39806) expressing met-asp-gln bGH protein was digested with NdeI and HindIII. The resulting NdeI-HindIII bGH fragment was isolated and ligated to a fragment from p8300-10A (ATCC No. 39785) prepared by partial digestion with both NdeI and HindIII. Such a ligation replaces the met-phe bGH gene fragment with the met-asp-gln bGH gene fragment. The plasmid so obtained, pSAL-130/5, expresses rec bGH. pSAL-170/10 was obtained by treating the EcoRI-AvaI fragment containing the $Tet^R$ gene of pBR322 plasmid (ATCC No. 37017) with DNA polymerase I (Klenow) and inserting it into pSAL-130/5 which had been digested with BamHI and filled in with DNA polymerase I (Klenow).

Figure 9:
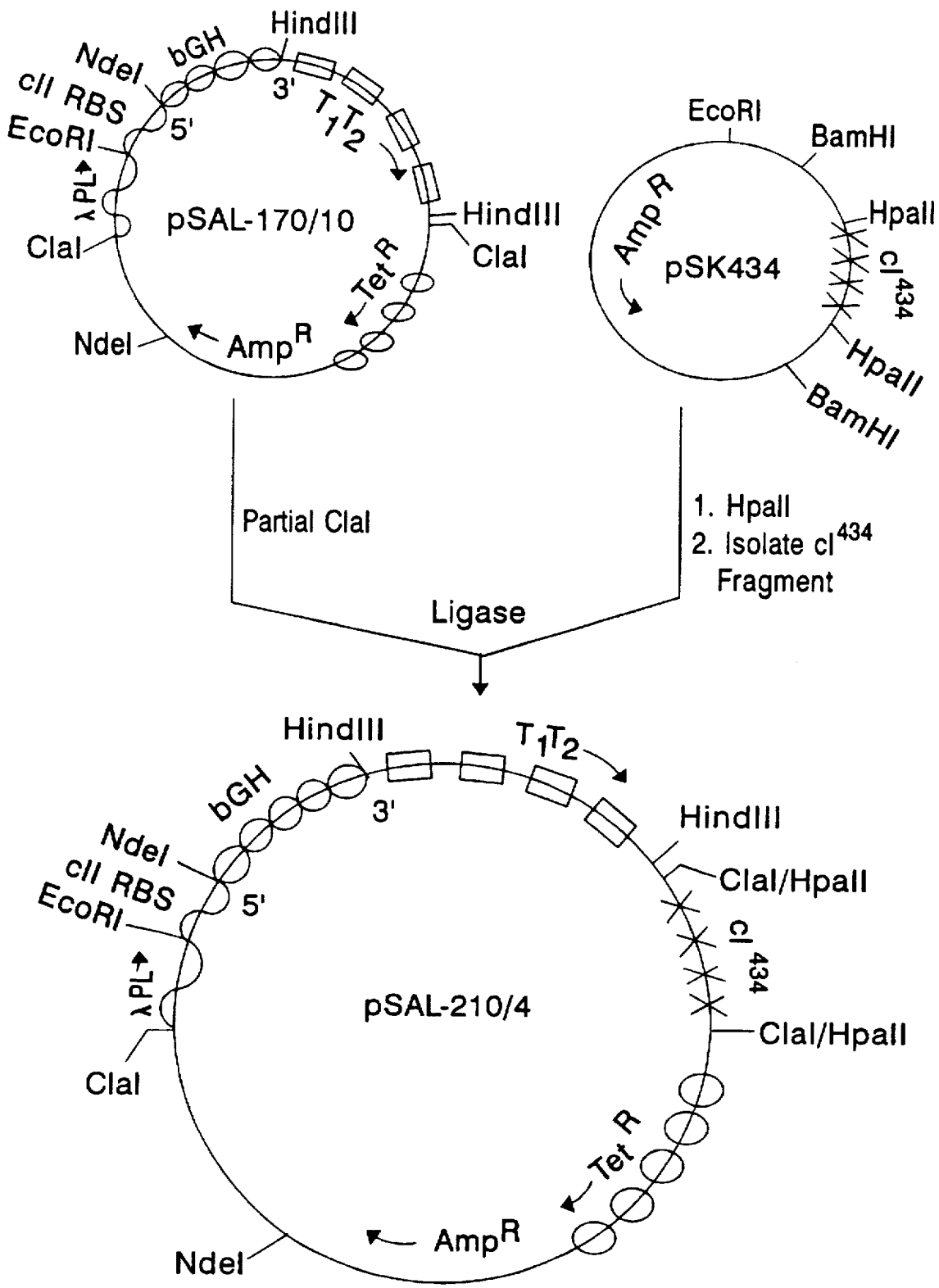

FIG. 9. Construction of pSAL-210/4.

Linear form DNA (form III) was prepared by partial ClaI digestion of pSAL-170/10. It was purified from an agarose gel and ligated to a HpaII-HpaII $cI^{434}$ gene fragment which was isolated from a HpaII digest of the plasmid pSK434 (ATCC No. 39784).

Figure 10:
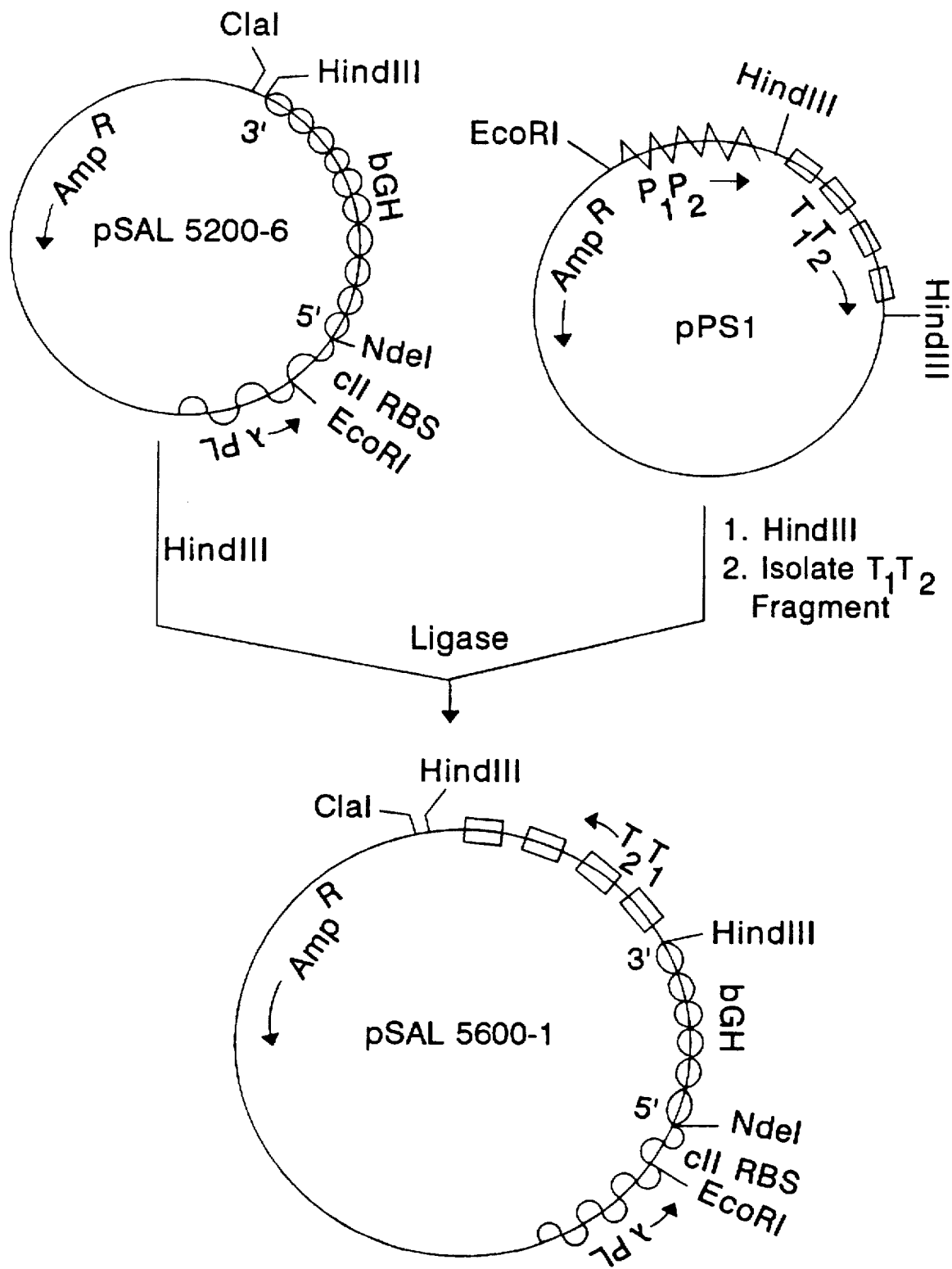

FIG. 10. Construction of pSAL 5600-1.

pSAL 5200-6 (FIG. 3) was digested with HindIII. The linear form DNA (form III) was purified from an agarose gel and ligated to a HindIII-HindIII fragment of about 1200 base pairs which contains the rRNA operon transcription termination sequences, $T_1T_2$. The $T_1T_2$ HindIII-HindIII fragment was isolated from the plasmid pPS1 (ATCC No. 39807) which was digested with HindIII. The resulting plasmid pSAL 5600-1 contains the $T_1T_2$ sequences at the 3' end of the met-asp-gln bGH sequence.

Figure 11:
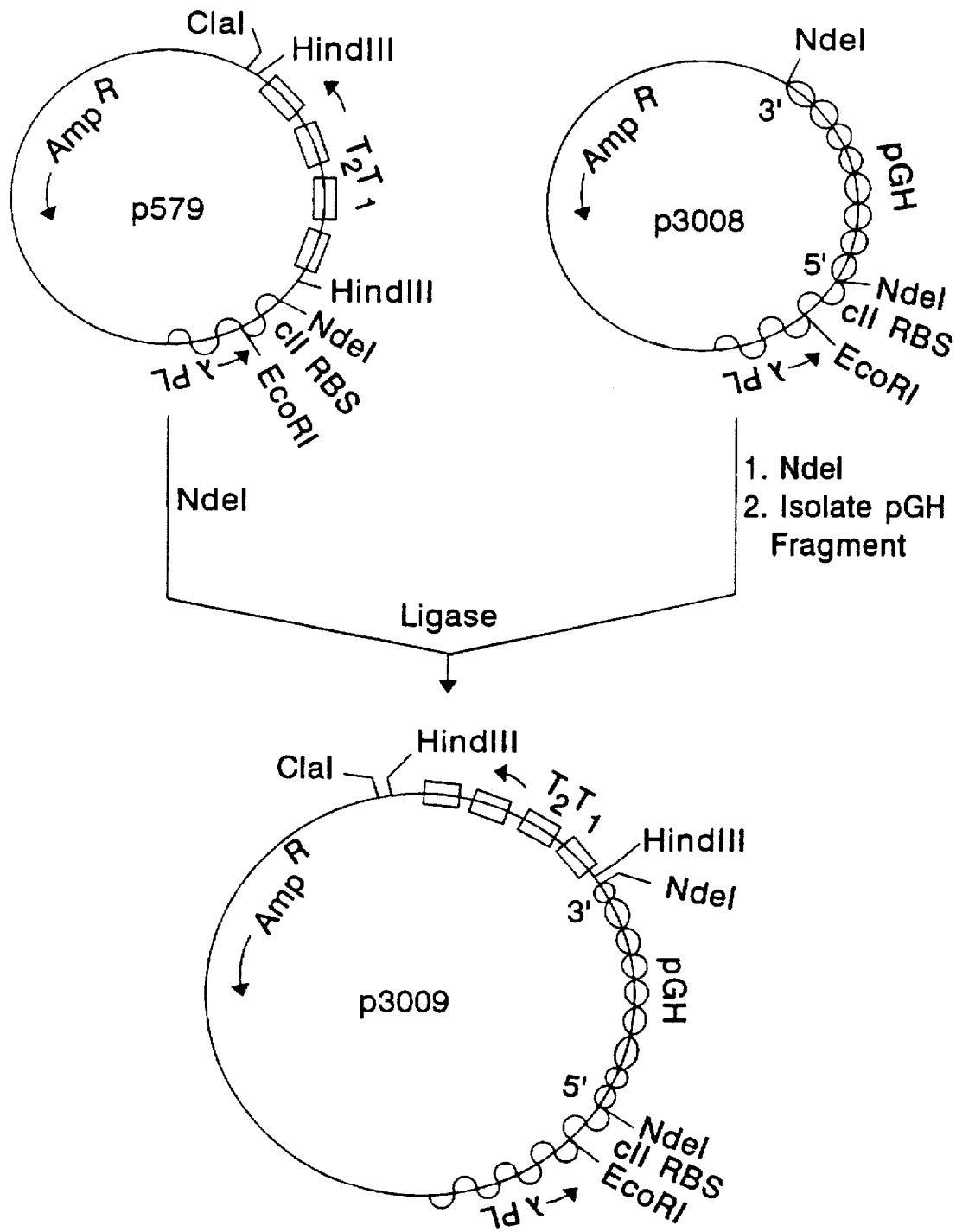

FIG. 11. Construction of p3009.

The NdeI-NdeI pGH fragment was isolated from plasmid p3008 (ATCC No. 39804) (FIG. 5). The fragment was inserted into the unique NdeI site of the expression vector p579 (FIG. 19) which had been digested with NdeI. The resulting plasmid p3009 expresses an analog of natural porcine growth hormone protein having a methionine residue added at the N-terminus.

Figure 12:
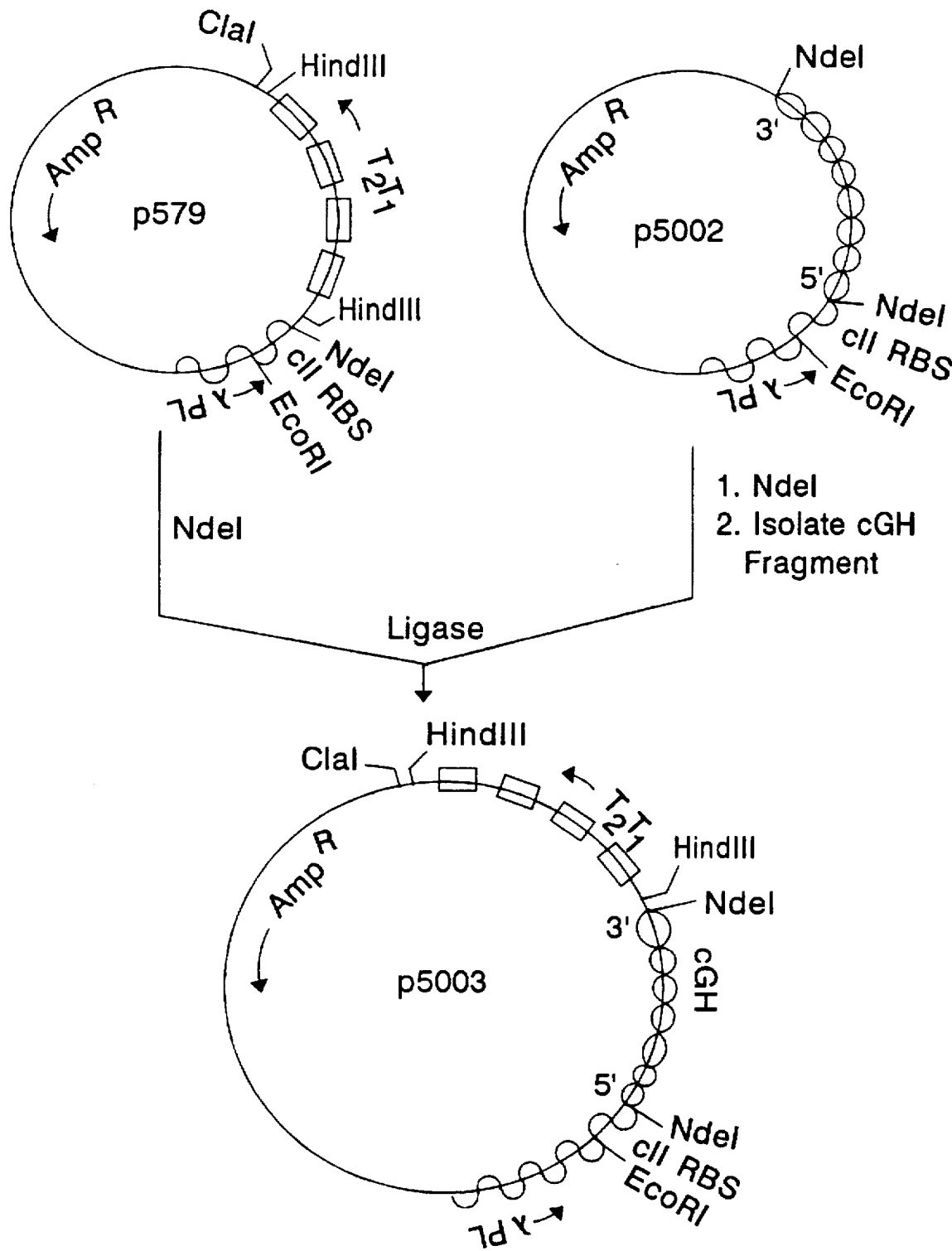

FIG. 12. Construction of p5003.

The NdeI-NdeI cGH fragment was isolated from plasmid p5002. The fragment was inserted into the unique NdeI site of the expression vector p579 (FIG. 19) which had been digested with NdeI. The resulting plasmid p5003 (ATCC No. 39792) expresses an analog of natural chicken growth hormone protein having a methionine residue added at the N-terminus.

Figure 13:
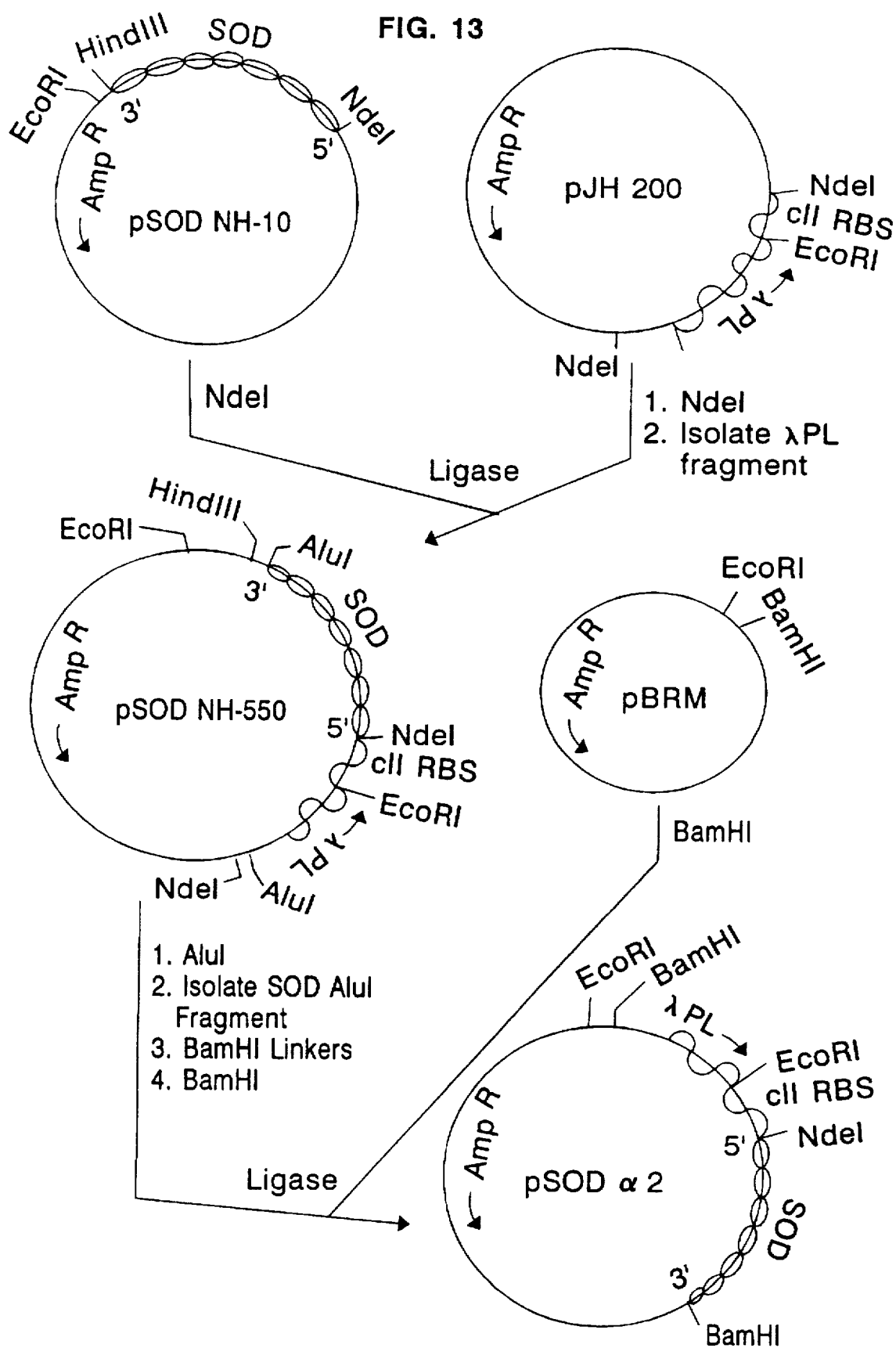

FIG. 13. Construction of pSODα2.

The pJH200 (ATCC No. 39783) expression vector was digested with NdeI. The 550 base pair NdeI fragment containing the $\lambda P_L$ promoter and $C_{II}$ ribosomal binding site was isolated and inserted into the unique NdeI site of plasmid pSOD NH-10 which had been digested with NdeI. (Plasmid pSOD NH-10 is derived from a cDNA clone of human SOD [Lieman-Hurwitz, J., et al., PNAS (1982) 79: 2808]) The resulting plasmid pSOD NH-550 was digested with AluI. (Only the relevant AluI site is shown in the figure.) The large AluI fragment containing the $\lambda P_L$ promoter and the SOD gene was isolated. BamHI linkers were attached and the resulting fragment was digested with BamHI. The BamHI digestion product was inserted into the unique BamHI site of pBRM (ATCC No. 37283) to form pSODα2 (ATCC No. 39786).

Figure 14:
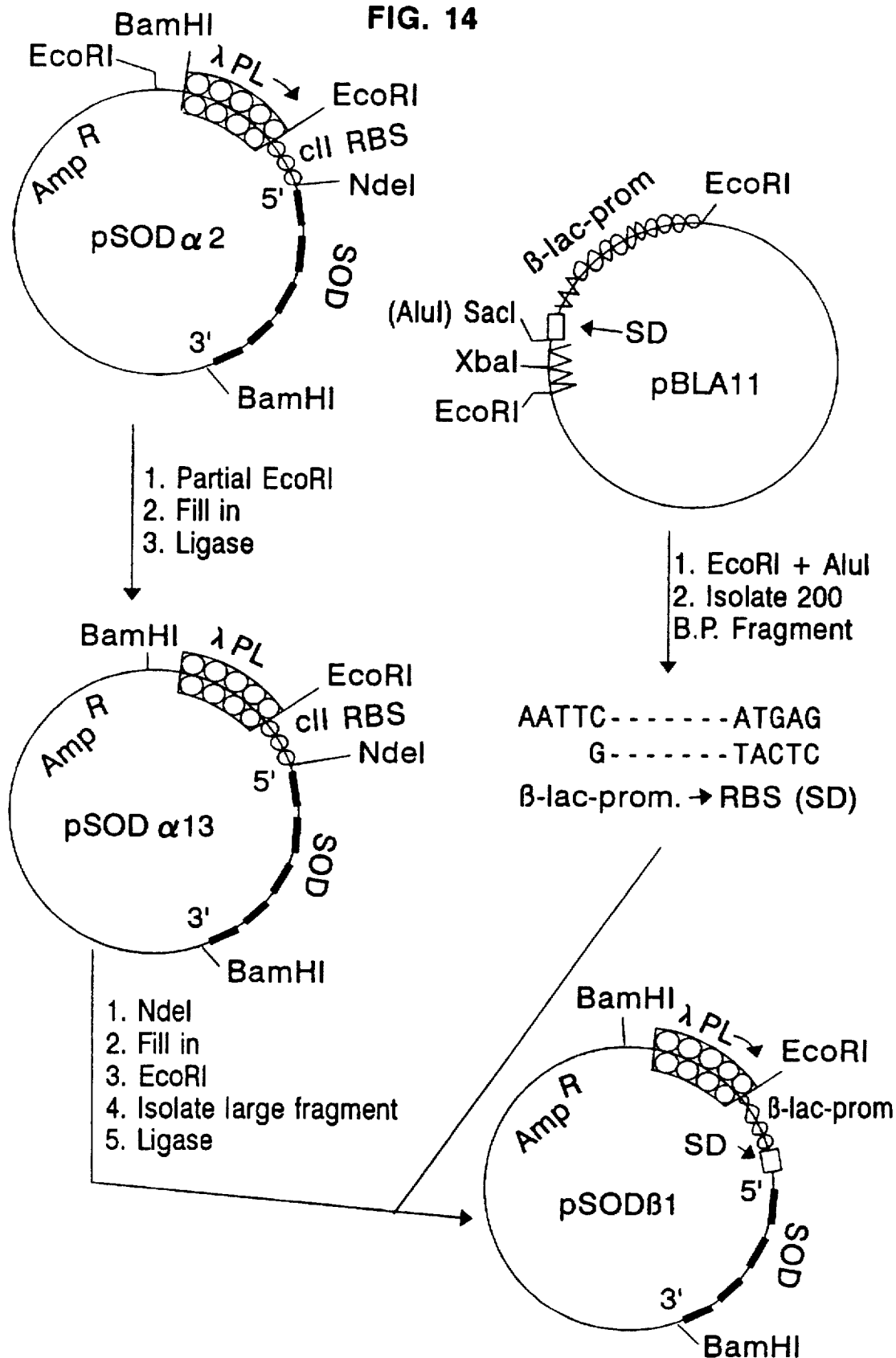

FIG. 14. Construction of pSODα13 and pSODβ1.

The plasmid pSODα2 (ATCC No. 39786) was partially digested with EcoRI and the resulting linear form DNA was isolated from an agarose gel. The purified DNA was filled in with DNA polymerase I (Klenow) and religated. The resulting clone pSODα13 contains one EcoRI site located at the 5' end of the ribosomal binding site. A fragment containing the β-lactamase promoter and ribosomal binding site was isolated from plasmid pBLA11 (ATCC No. 39788) which had been digested with EcoRI and AluI. The 200 base pair fragment was ligated to the large fragment isolated from pSODα13 which had been digested with NdeI, filled in with DNA polymerase I (Klenow) and then digested with EcoRI. The resulting plasmid pSODβ1 contains the ribosomal binding site of the β-lactamase gene and the $\lambda P_L$ promoter.

Figure 15:
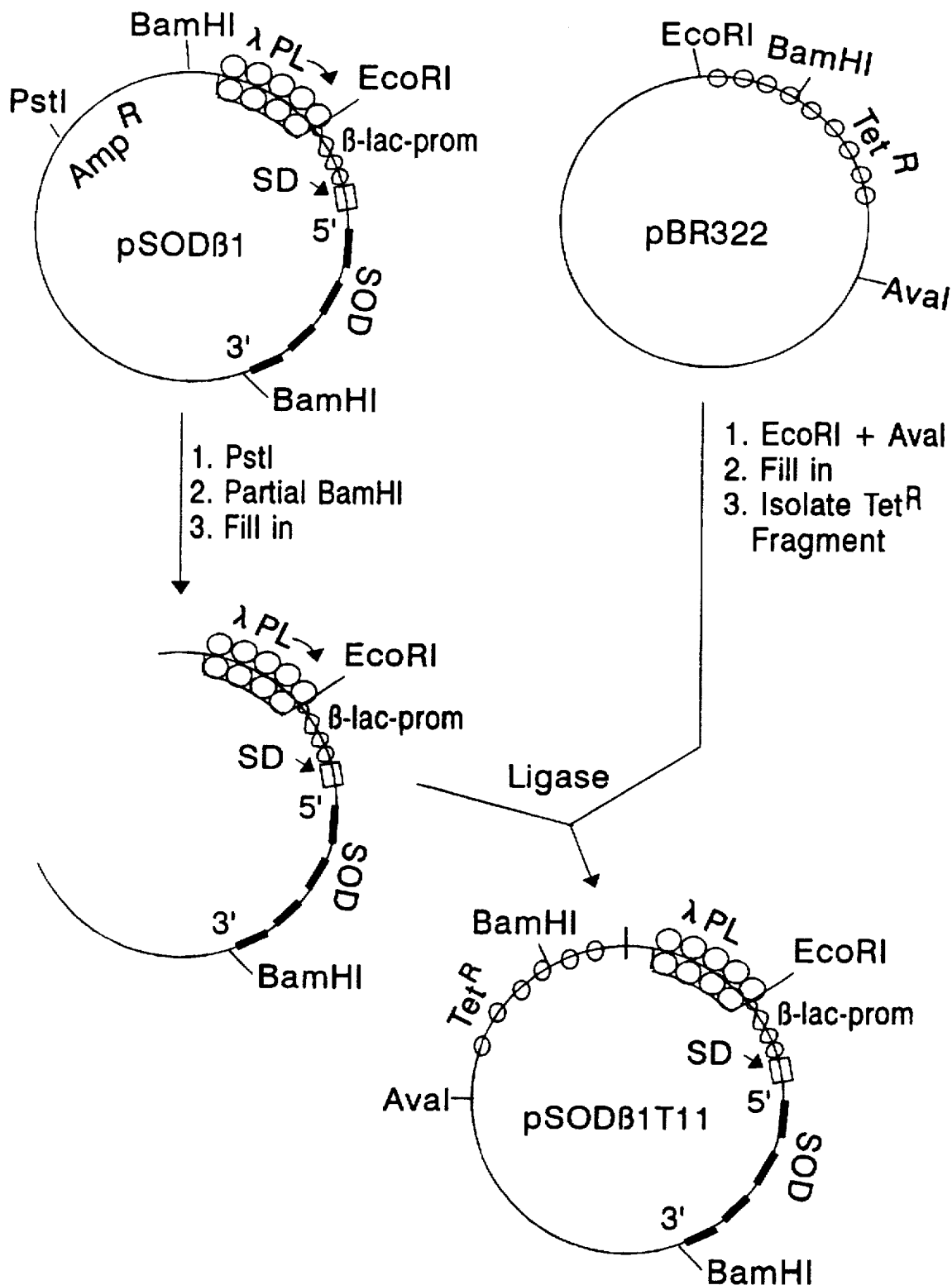

FIG. 15. Construction of pSODβ$_1$T$_{11}$.

Plasmid pBR322 (ATCC No. 37017) was digested with EcoRI and AvaI. The resulting DNA was filled in with DNA polymerase I (Klenow). The $Tet^R$ gene fragment was then isolated and ligated to the large fragment isolated from pSODβ1 (FIG. 14) plasmid which had been digested with PstI followed by a partial BamHI digest and then filled in with DNA polymerase I (Kienow). The resulting plasmid pSODβ$_1$T$_{11}$ contains the $Tet^R$ gene.

Figure 16:
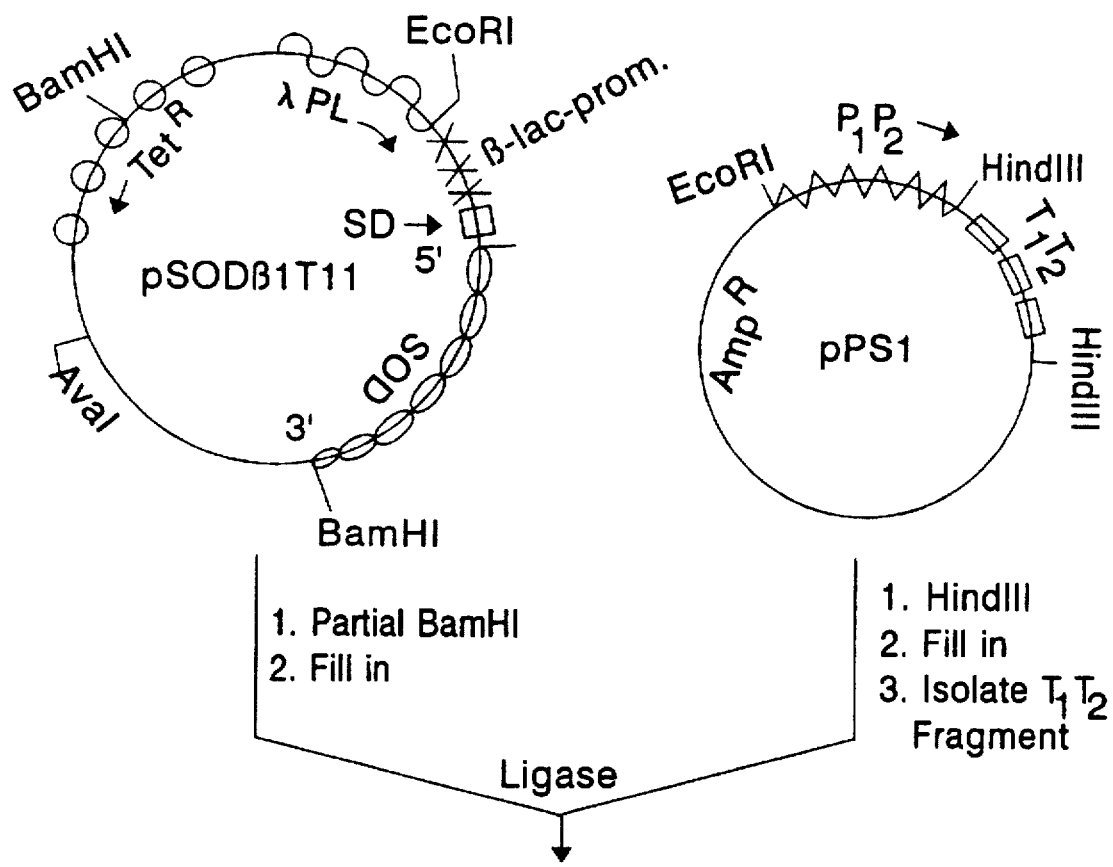
Figure 16:
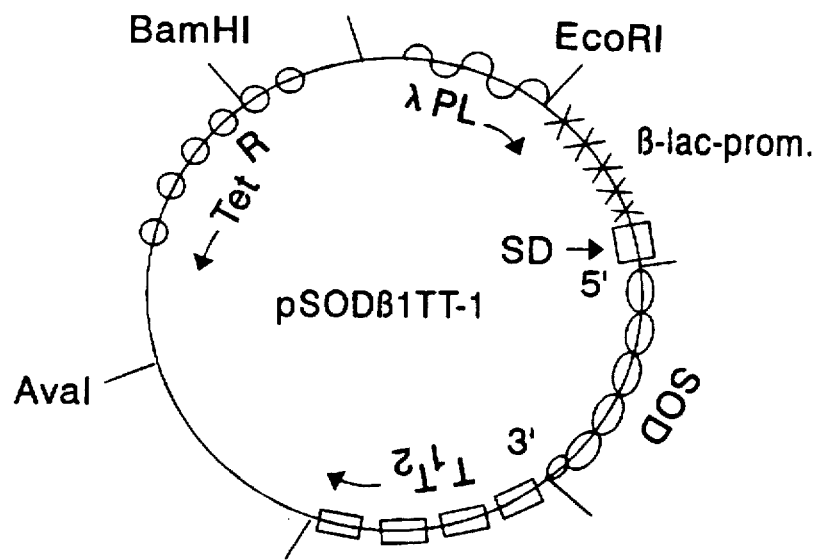

FIG. 16. Construction of pSODβ$_1$TT-1.

The rRNA $T_1T_2$ transcription termination fragment was isolated from plasmid pPS1 (ATCC No. 39807) which had been digested with HindIII and filled in with DNA polymerase I (Klenow). The fragment was ligated to plasmid pSODβ$_1$T$_{11}$ (FIG. 15) which had been partially digested with BamHI and filled in with DNA polymerase I (Klenow).

Figure 17:
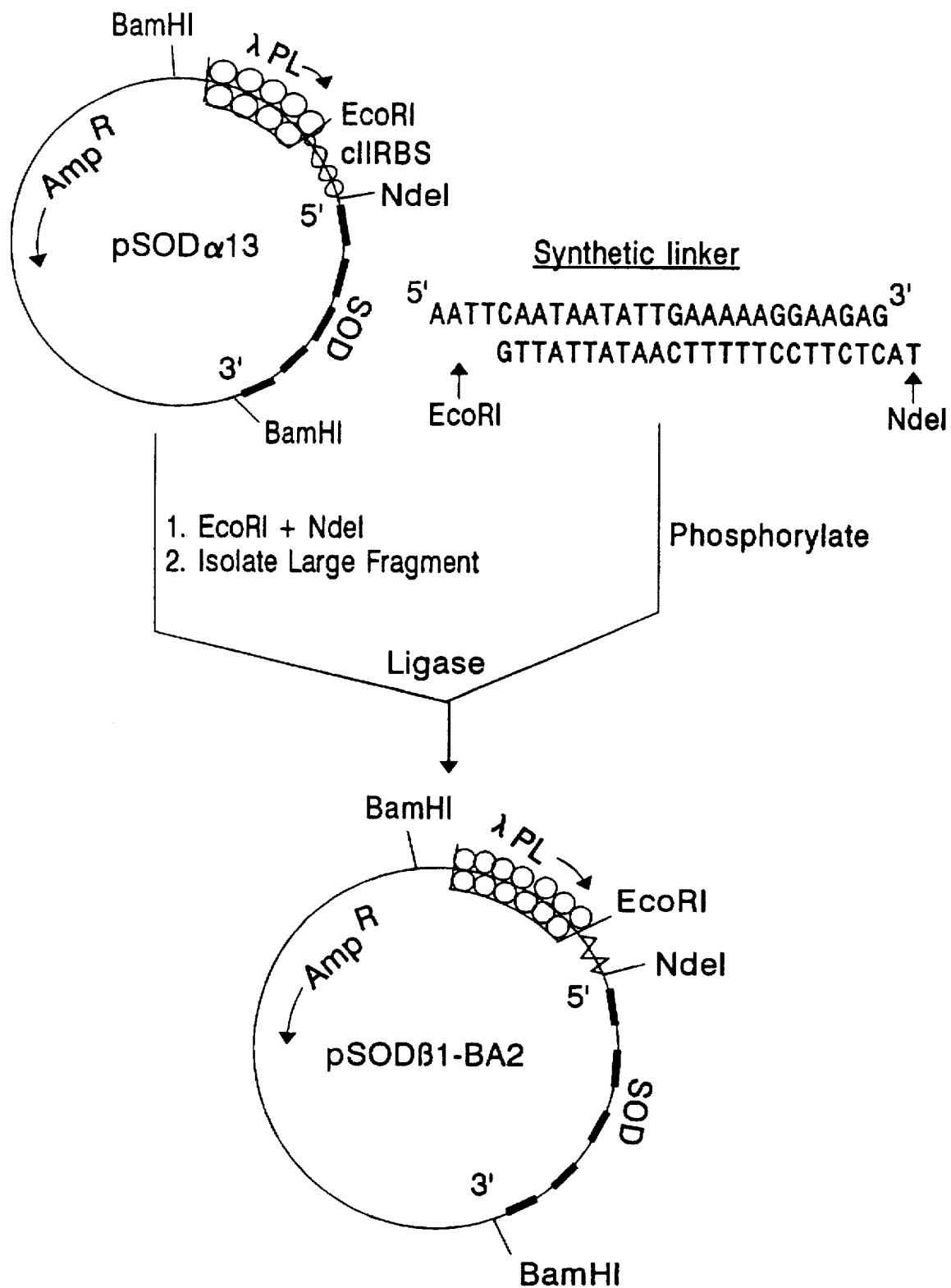

FIG. 17. Construction of pSODβ$_1$-BA2.

A synthetic DNA fragment with the sequence:

5'-AATTCAATAATATTGAAAAAGGAAGAG-3'

GTTATTATAACTTTTTCCTTCTCAT which is similar to the sequence of the natural β-lactamase ribosomal binding site, was phosphorylated and ligated to the large fragment of pSODα13 plasmid (FIG. 14) which had been digested with NdeI and EcoRI.

Figure 18:
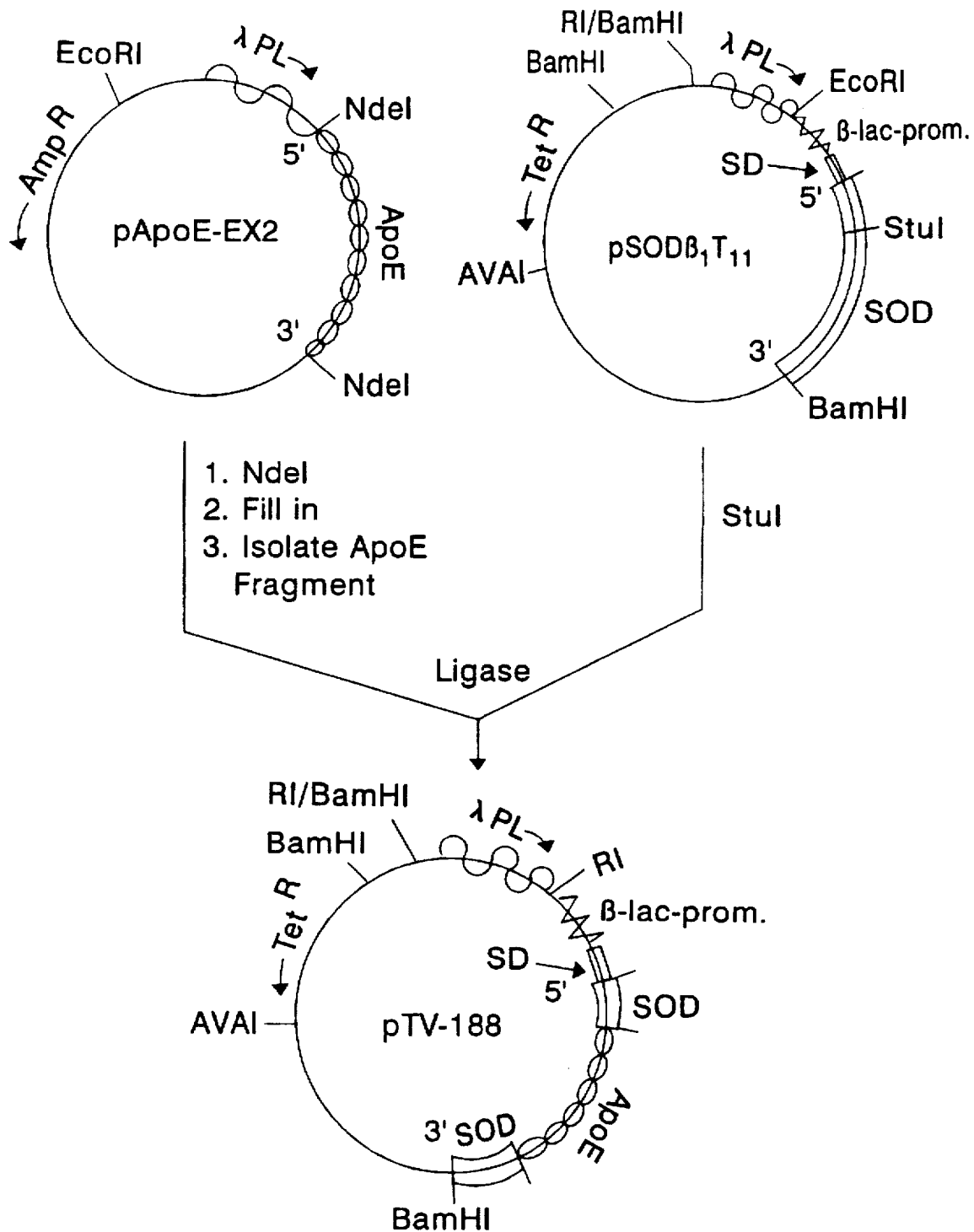

FIG. 18. Construction of pTV-188.

Plasmid pApoE-EX2 (ATCC No. 39787) was digested with NdeI and then fragments filled in with DNA polymerase I (Klenow). The resulting ApoE gene fragment was isolated and inserted into the unique blunt end StuI site of the pSODβ$_1$T$_{11}$ plasmid (FIG. 15). The resulting plasmid pTV-188 expresses an ApoE fused protein.

Figure 19:
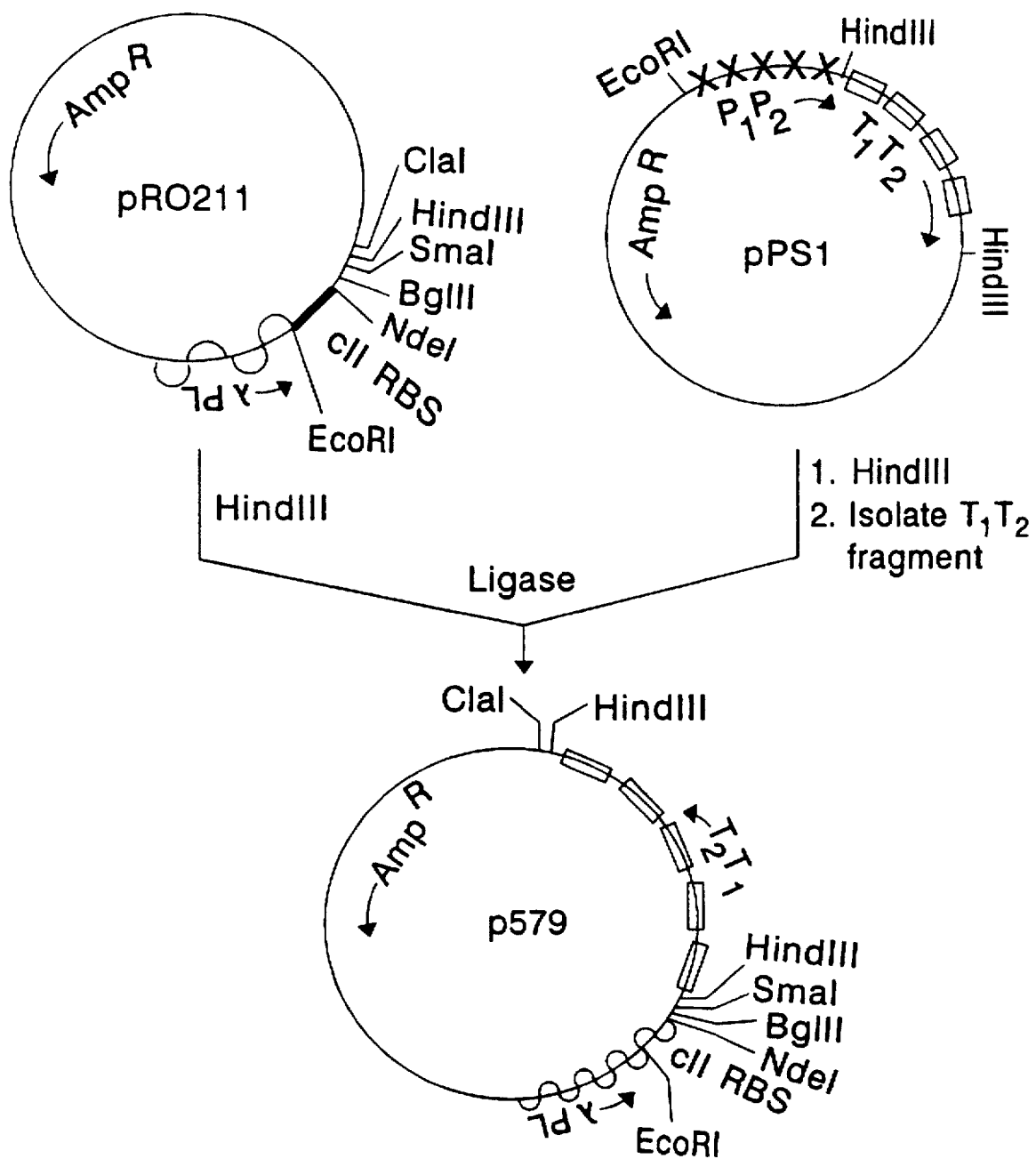

FIG. 19. Construction of p579.

The rRNA operon $T_1T_2$ transcription termination fragment was isolated from plasmid pPS1 (ATCC No. 39807) which had been digested with HindIII. The $T_1T_2$ fragment was inserted into the unique HindIII site of pRO211 (FIG. 2) which had been digested with HindIII. The resulting expression vector, p579, contains the $\lambda P_L$ promoter, the $C_{II}$ ribosomal binding site, followed by the $T_1T_2$ transcription termination signals.

Figure 20:
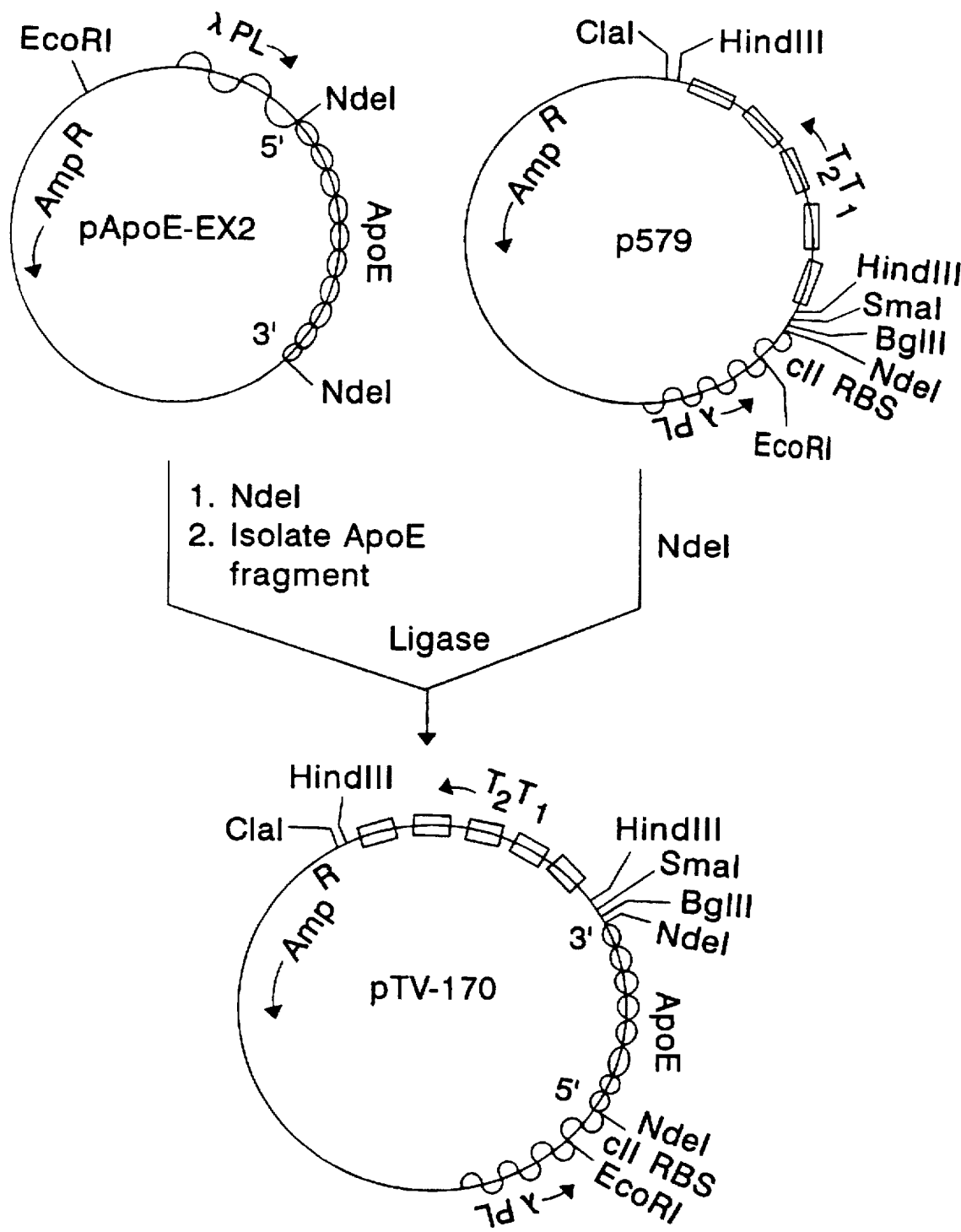

FIG. 20. Construction of pTV-170.

The NdeI-NdeI ApoE fragment was isolated from plasmid pApoE-EX2 (ATCC No. 39787) and inserter into the unique NdeI site of the expression vector p579 (FIG. 19) which had been digested with NdeI. The resulting plasmid pTV-170 expresses an analog of natural human ApoE protein having a methionine residue added at the N-terminus.

Figure 21:
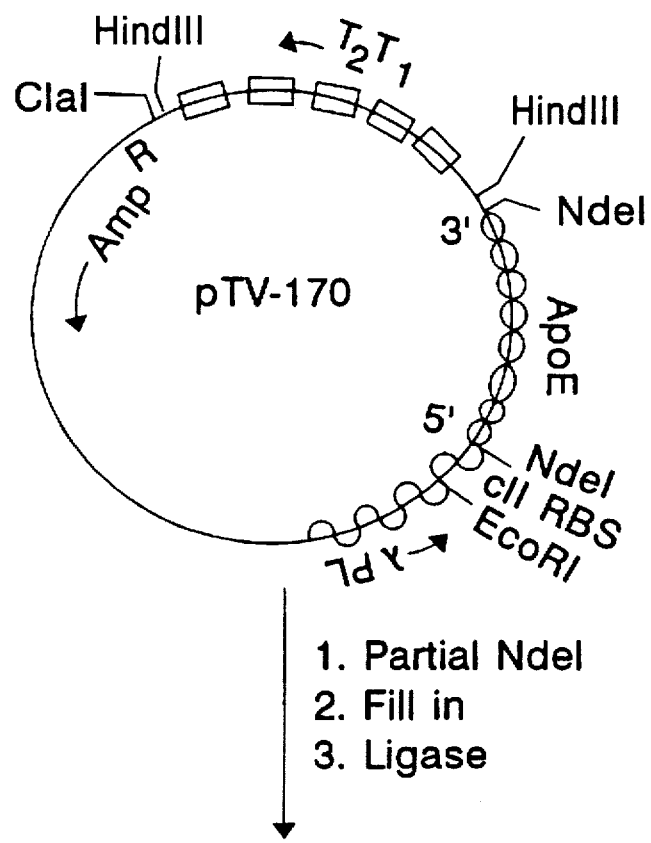
Figure 21:
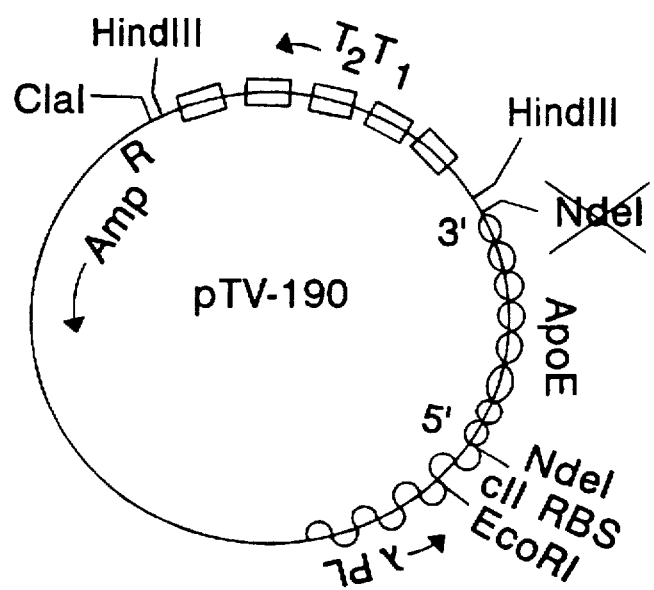

FIG. 21. Construction of pTV-190.

The plasmid pTV-170 (FIG. 20) was partially digested with NdeI and filled in with DNA polymerase I (Klenow). The isolated linear form DNA was religated to yield the plasmid pTV-190 which was analyzed and found to have only one NdeI site at the 5' end of the ApoE gene.

Figure 22:
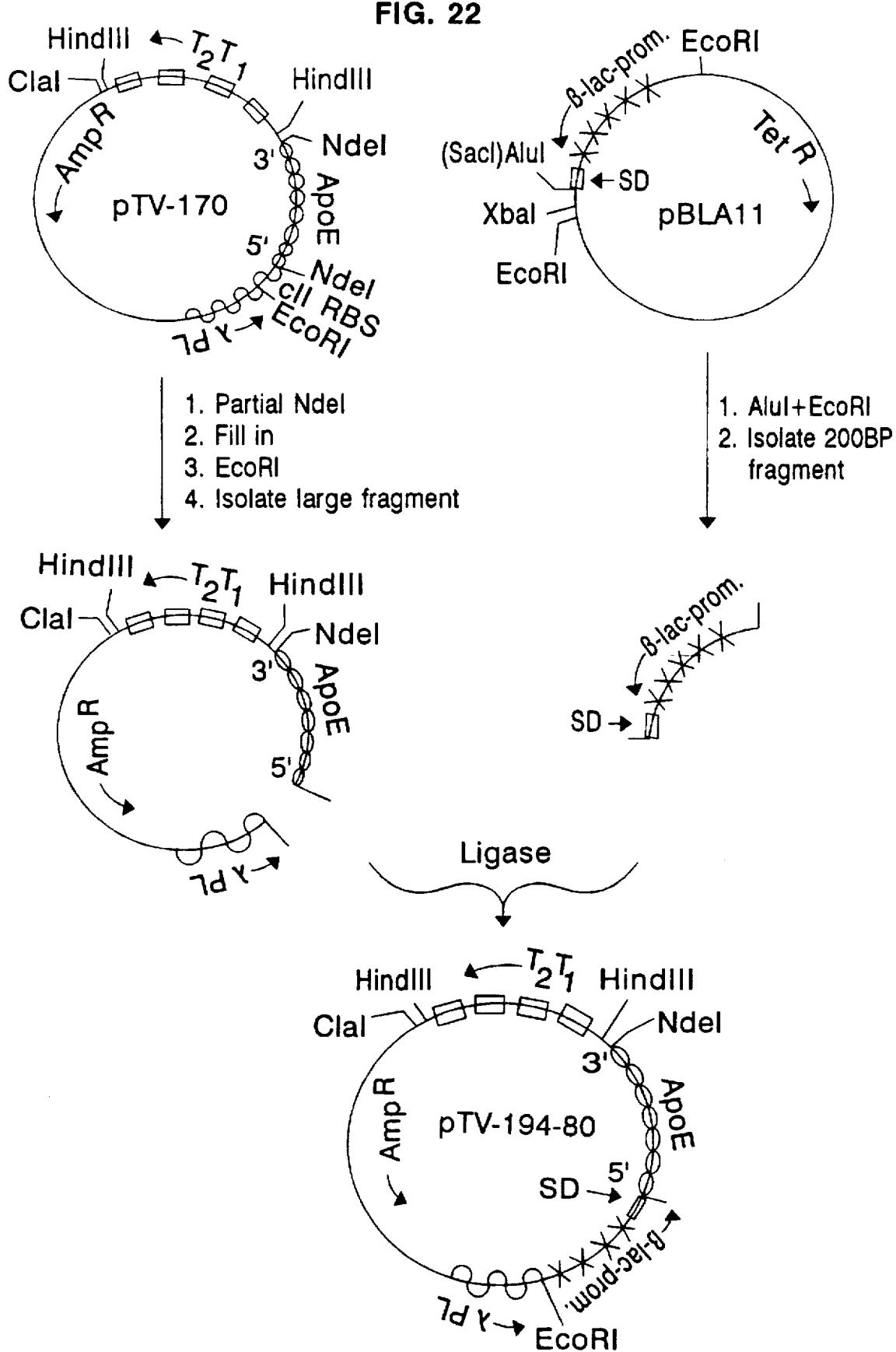

FIG. 22. Construction of pTV-194-80.

The β-lactamase promoter and ribosomal binding site fragment was isolated from plasmid pBLA11 (ATCC No. 39788) after digestion with EcoRI and AluI. This fragment was ligated to the large fragment of pTV-170 (FIG. 20) plasmid which had been digested with NdeI, filled in with DNA polymerase I (Klenow) and then digested with EcoRI.

Figure 23:
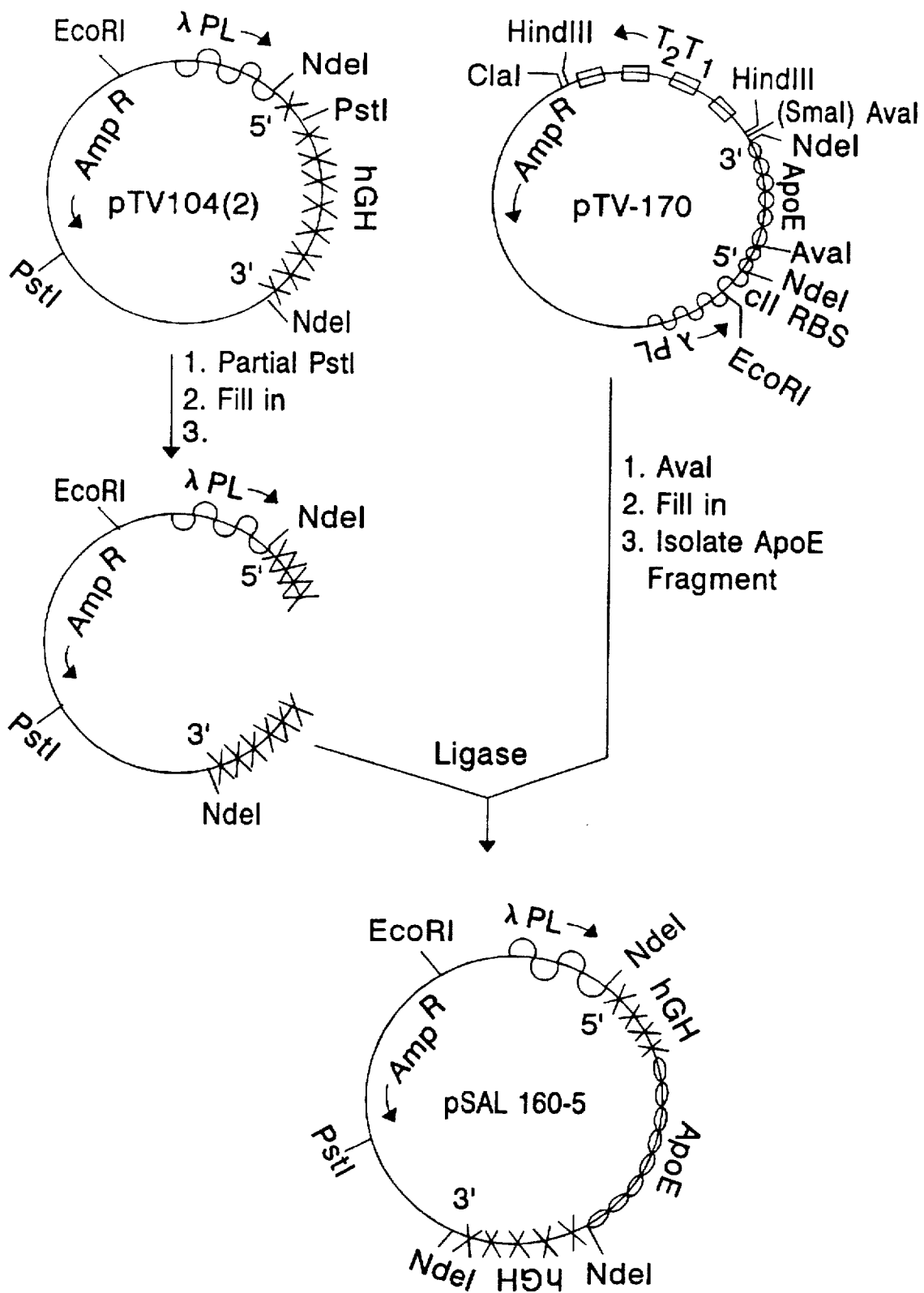

FIG. 23. Construction of pSAL 160-5.

An AvaI-AvaI fragment containing the ApoE DNA sequence was isolated from pTV-170 (FIG. 21) which was digested with AvaI. The fragment was filled in with DNA polymerase I (Klenow) and isolated on agarose gel. The purified ApoE fragment was inserted into the PstI site cf the pTV 104(2) plasmid (ATCC No. 39384) which was partially digested with PstI and filled in with DNA Polymerase I (Klenow). The resulting plasmid is designated pSAL 160-5.

Figure 24:
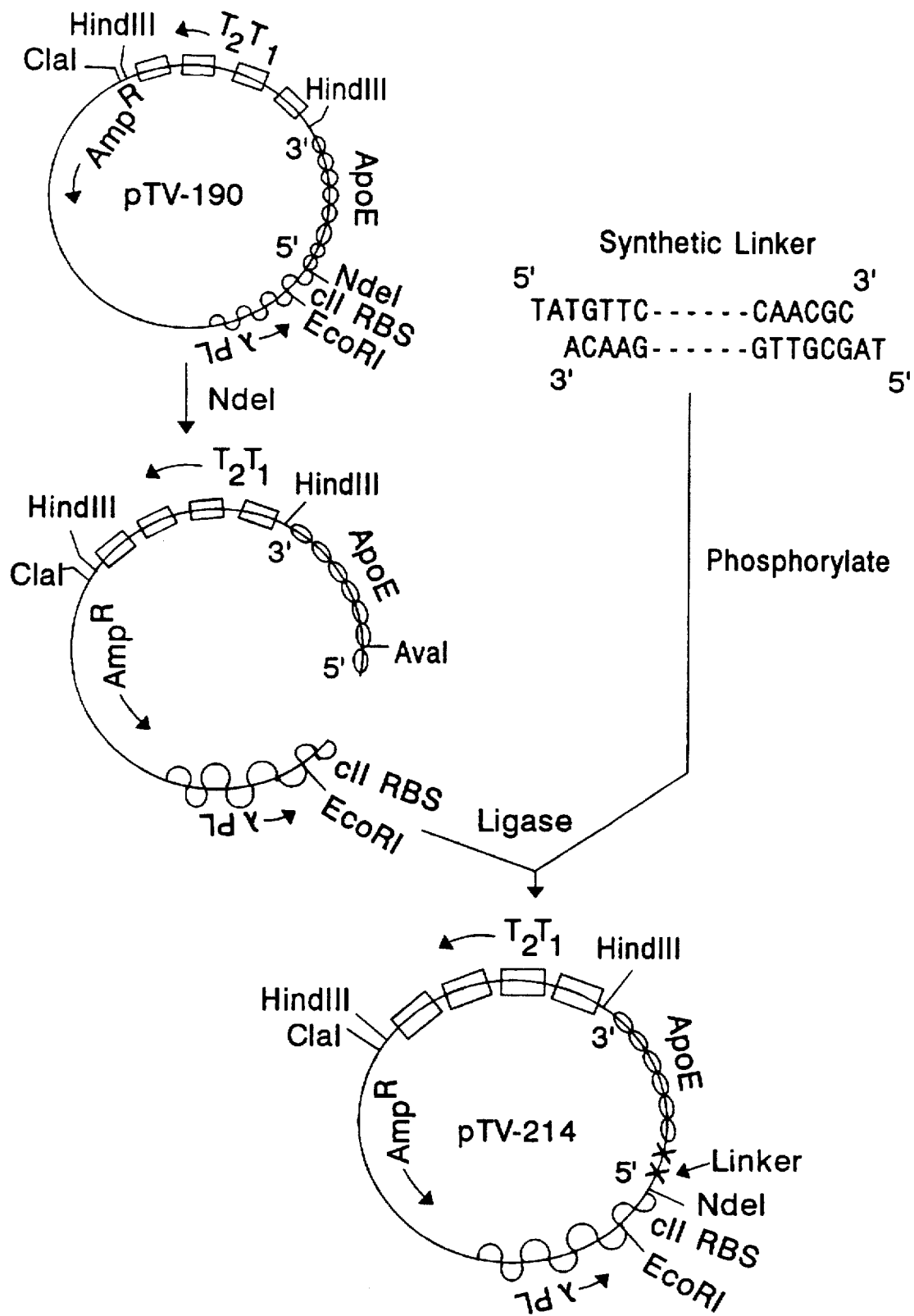

FIG. 24. Construction of pTV-214.

A synthetic fragment containing methionine followed by the first 13 amino acids of human growth hormone with the sequence:

TATGTTCCCAACCATTCCATTATC-
CCGTCTGTTCGACAACGC

ACAAGGGTTGGTAAGGTAATAGGGCAGA-
CAAGCTGTTGCGAT was phosphorylated using $\delta^{-32}$P-ATP and polynucleotide kinase. The phosphorylated linker was inserted into the unique NdeI site of pTV 190 plasmid which had been digested with NdeI.

Figure 25:
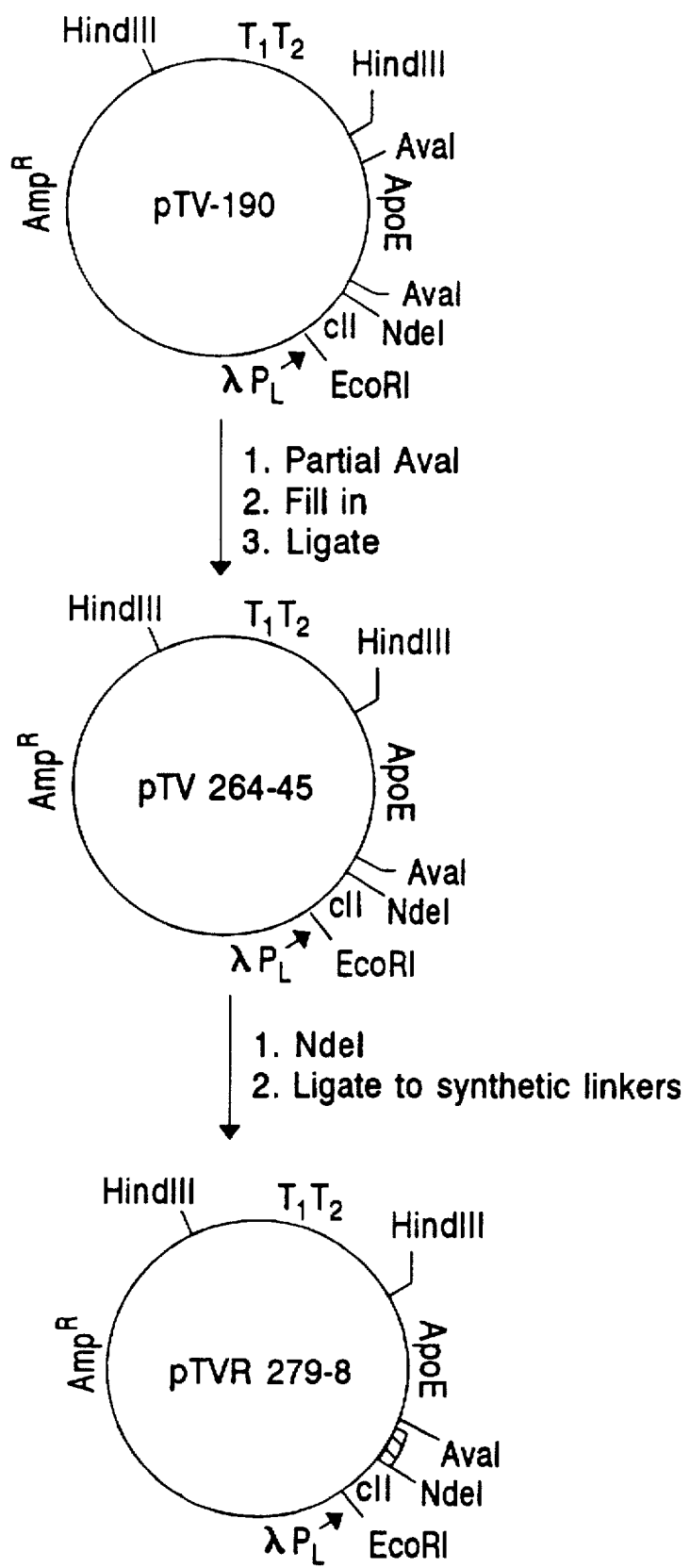

FIG. 25. Construction of pTVR 279-8.

pTVR 279-8 was constructed from pTV 264-45 which was constructed from pTV 190.

Plasmid pTV 190, which directs the expression of Met-ApoE3 analog was partially cleaved with AvaI, "filled in" using the Klenow fragment of DNA polymerase I and religated. The resulting plasmid, designated pTV 264-45 is deleted of the AvaI site at the 3' end of the gene.

Plasmid pTV 264-45 was digested to completion with NdeI and ligated to phosphorylated synthetic linkers of the sequence:

5'-TATGCTGCTGCT

ACGACGACGAAT-5'

The resulting plasmid designated pTVR 279-8 directs the expression of a met-leu-leu-leu-met-ApoE3 analog.

Figure 26:
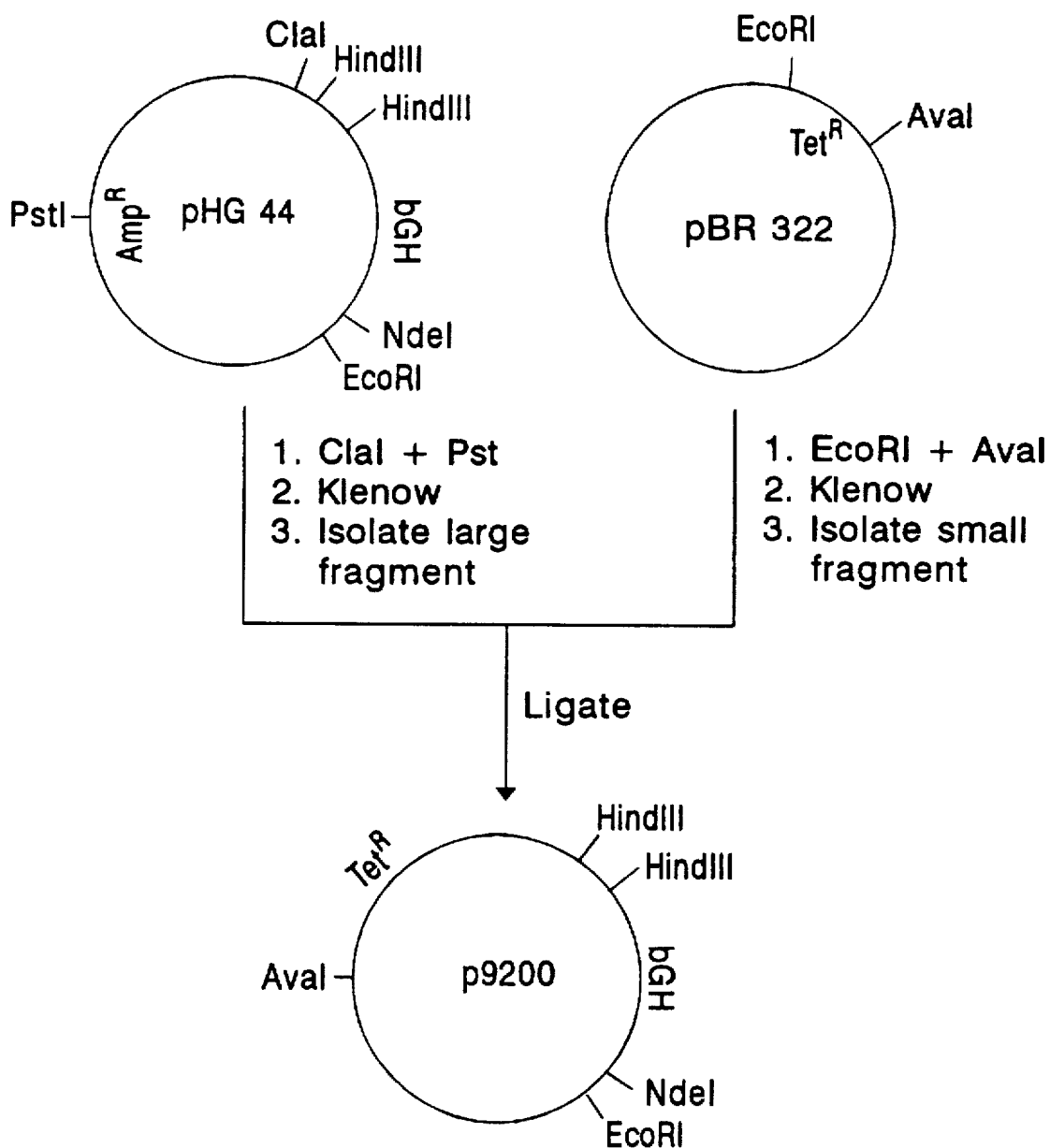

FIG. 26. Construction of p9200.

Plasmid p9200 was constructed by eliminating most of the ampicillin resistance gene from pHG44 and replacing it with the tetracycline resistance gene of pBR322.

pHG44 was cleaved with ClaI and PstI treated with the Klenow fragment of DNA polymerase I, and the large DNA fragment was isolated. This fragment was ligated to the small DNA fragment of pBR322 isolated after cleaving pBR322 with EcoRI and AvaI and treating with the Klenow fragment. The plasmid resulting from the ligation was designated p9200.

Plasmid p9200 directs the expression of met-asp-gln-bGH analog and confers tetracycline resistance to its host cell.

Figure 27:
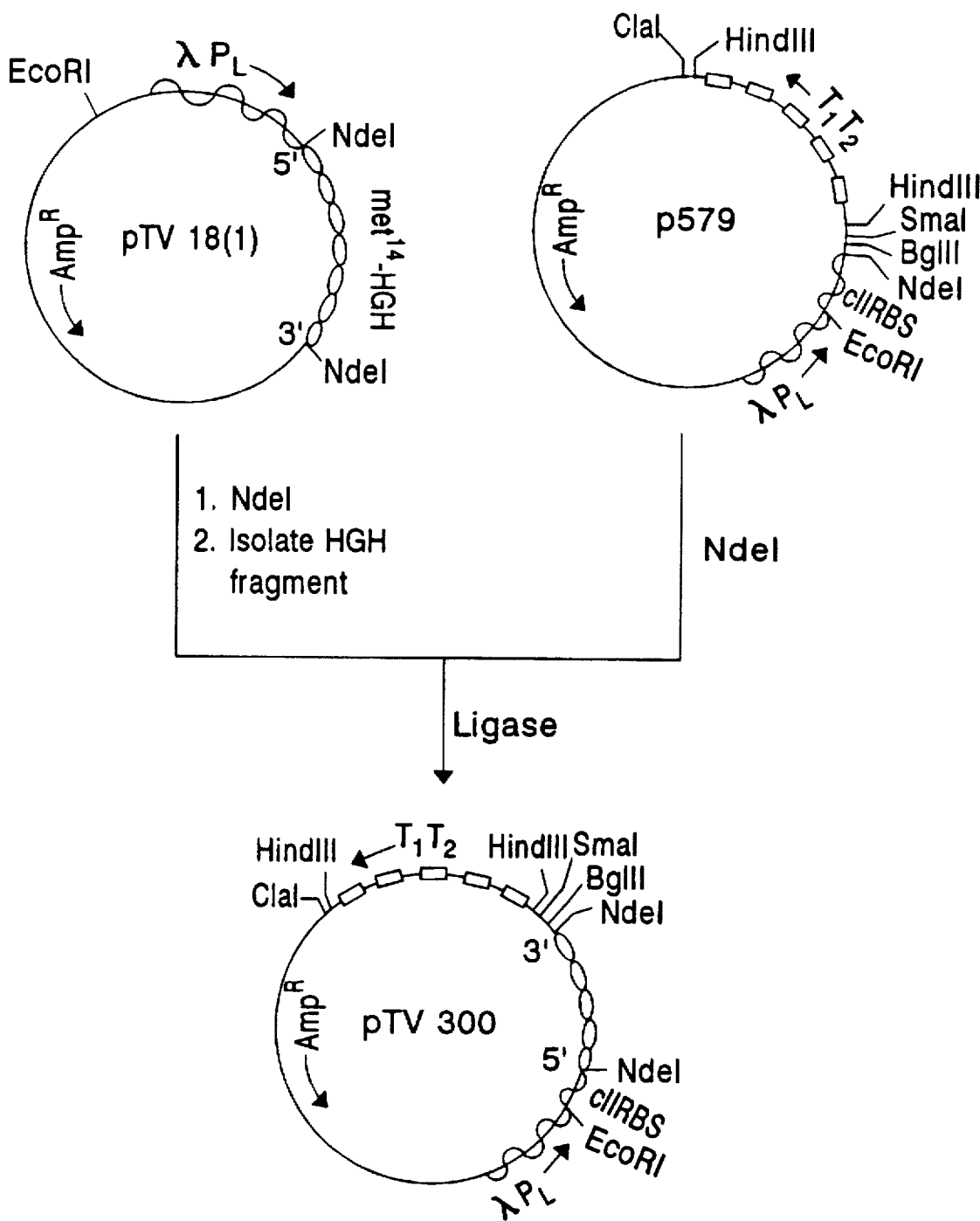

FIG. 27. Construction of pTV 300.

pTV 300 directs the expression of met$^{14}$-hGH analog.

pTV 300 was constructed by cleaving pTV 18(1) with NdeI, isolating the met$^{14}$-hGH DNA and ligating it to p579 (FIG. 19) cleaved with NdeI.

pTV 18(1) may be obtained as described in European Patent Application Publication No. 0 131 843 A1, published Jan. 23, 1985 or as described in corresponding U.S. patent application Ser. No. 514,188, filed Jul. 15, 1983, the latter of which is hereby incorporated by reference.

Figure 28:
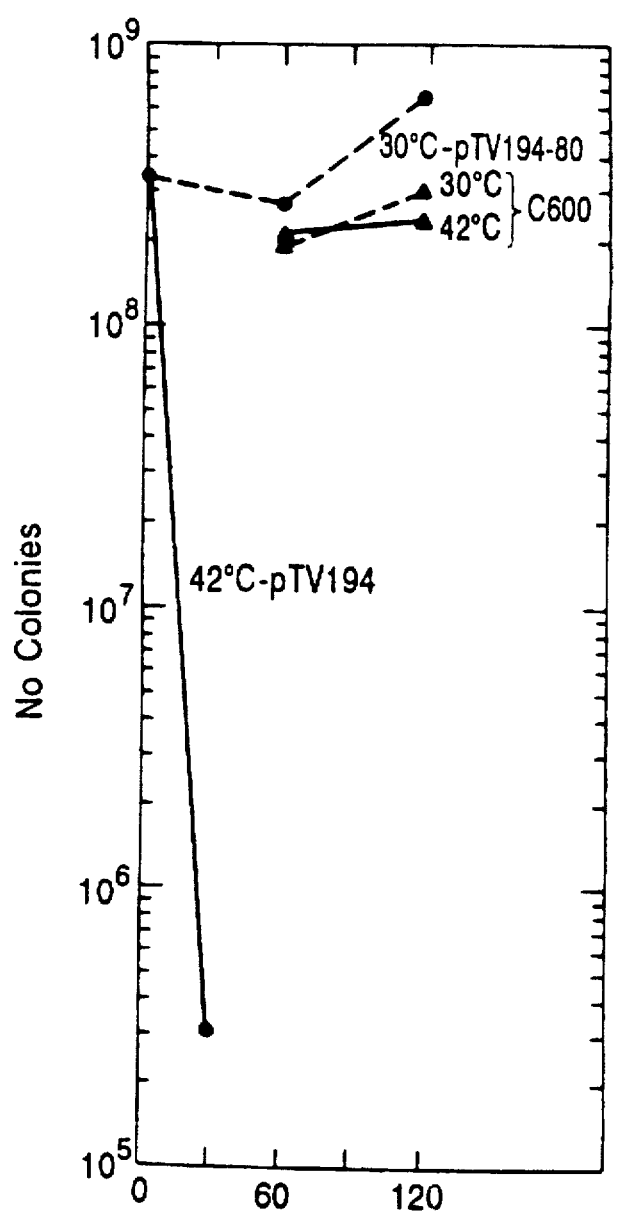

FIG. 28. Cellular Toxicity Associated With Intracellular Accumulation of ApoE Analog.

Cultures of C600 cells (5 ml) containing pTV 194-80 or non-transfected control cells were induced by raising the incubation temperature from 30° to 42° C. At the indicated times a 1 ml aliquot of the culture was removed, rapidly cooled with ice, serially diluted in growth medium, plated on agar in the presence of appropriate antibiotics and incubated overnight at 30° C. The number of colonies was determined from the average of duplicate plates. Parallel cultures of pTV 194-80 transfected and nontransfected C600 cells maintained at 30° served as noninduced controls.

Figure 29B:
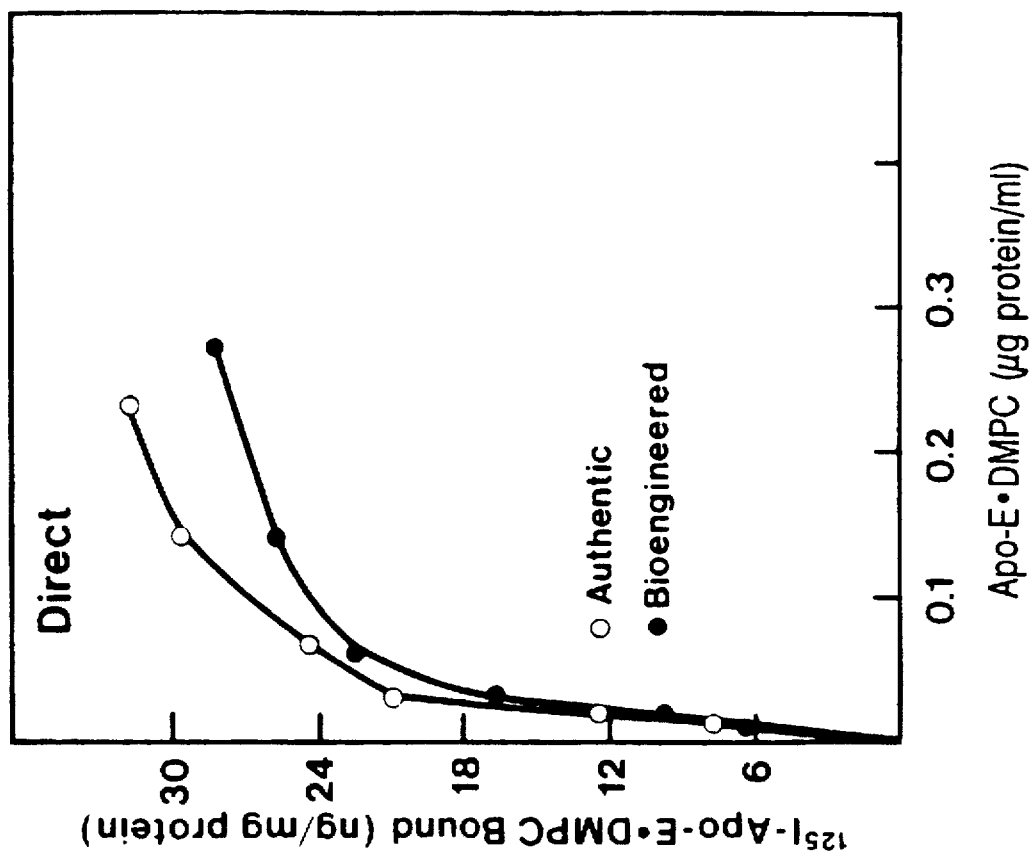
Figure 29A:
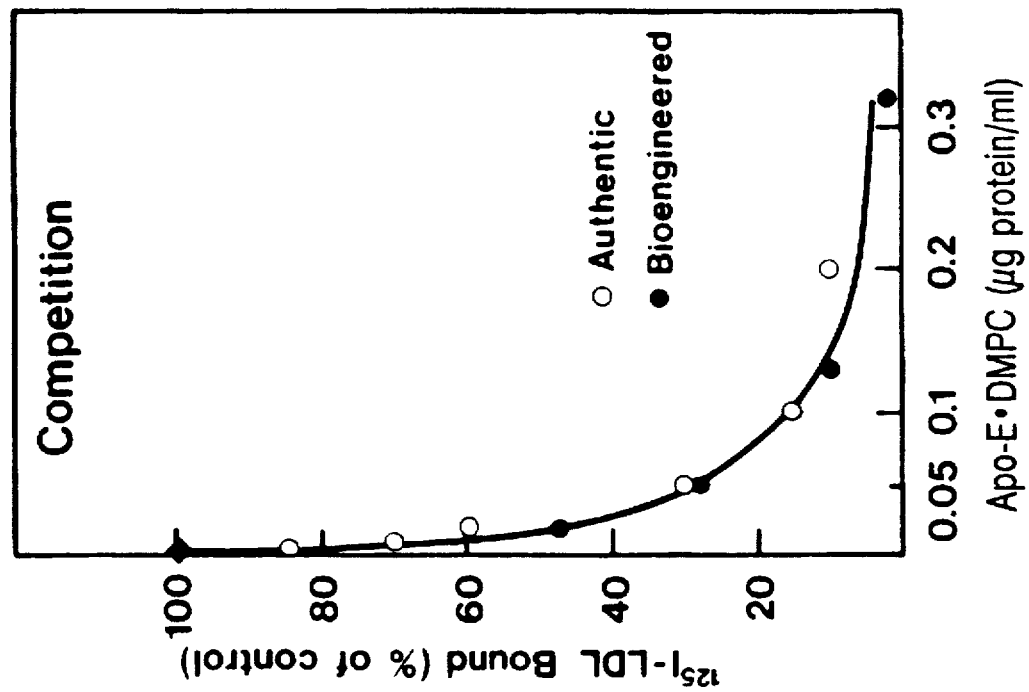

FIG. 29. Binding of ApoE DMPC Complexes to Apo-B, E(LDL) Receptors on Fibroblasts.

Phospholipid complexes of bioengineered (met-ApoE3 analog) and authentic ApoE were prepared by incubation of the proteins and DMPC at 22° C. The complexes were separated from noncomplexed material by density gradient ultracentrifugation as described (30, following Example 15). Left: Ability of bioengineered and authentic ApoE.DMPC complexes to compete with $^{125}$I-labeled human LDL for binding to cultured fibroblast receptors at 4° C. Right: Ability of $^{125}$I-labeled ApoE analog and authentic ApoE DMPC complexes to bind directly to cultured fibroblasts.

Figure 30:
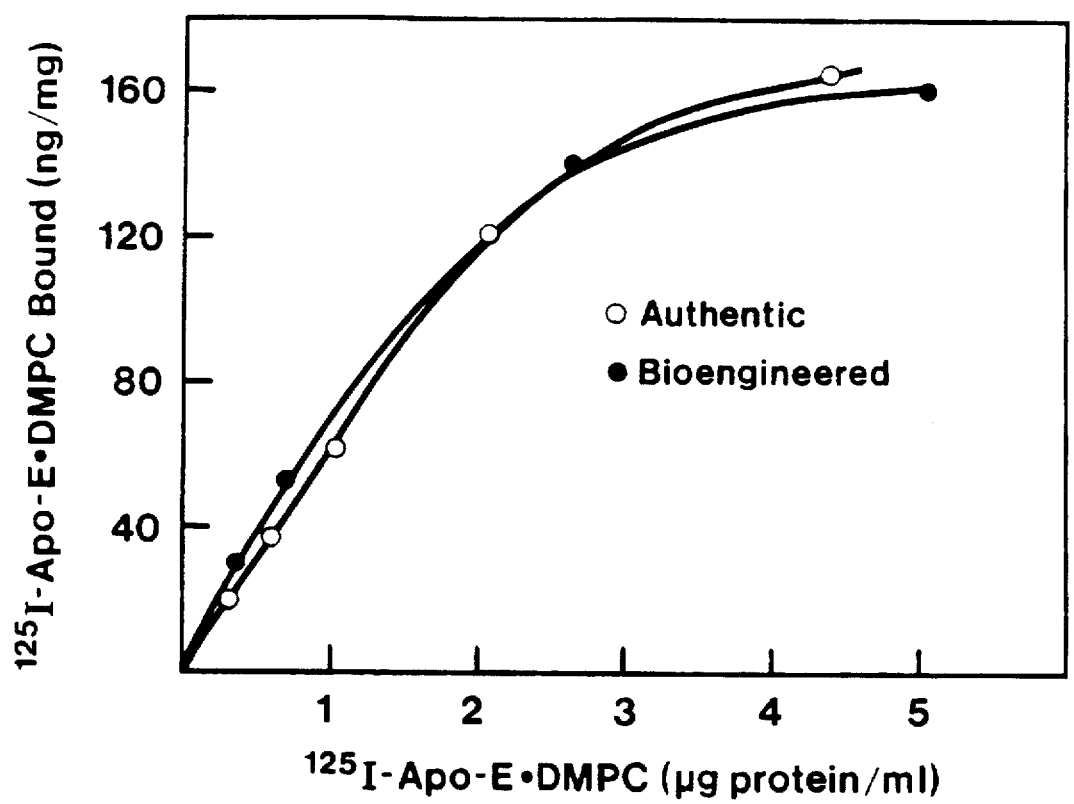

FIG. 30. Binding of $^{125}$I-ApoE DMPC Complexes to ApoE Receptors on Hepatic Membranes.

Phospholipid (DMPC) complexes were prepared as described in FIG. 29. Hepatic membranes from adult cholesterol-fed dogs served as the source for the ApoE receptors and were prepared as described (32, following Example 15). The binding of the $^{125}$I-labeled bioengineered and authentic ApoE DMPC complexes to the membranes was performed at 4° C. as described (32, following Example 15).

Figure 31:
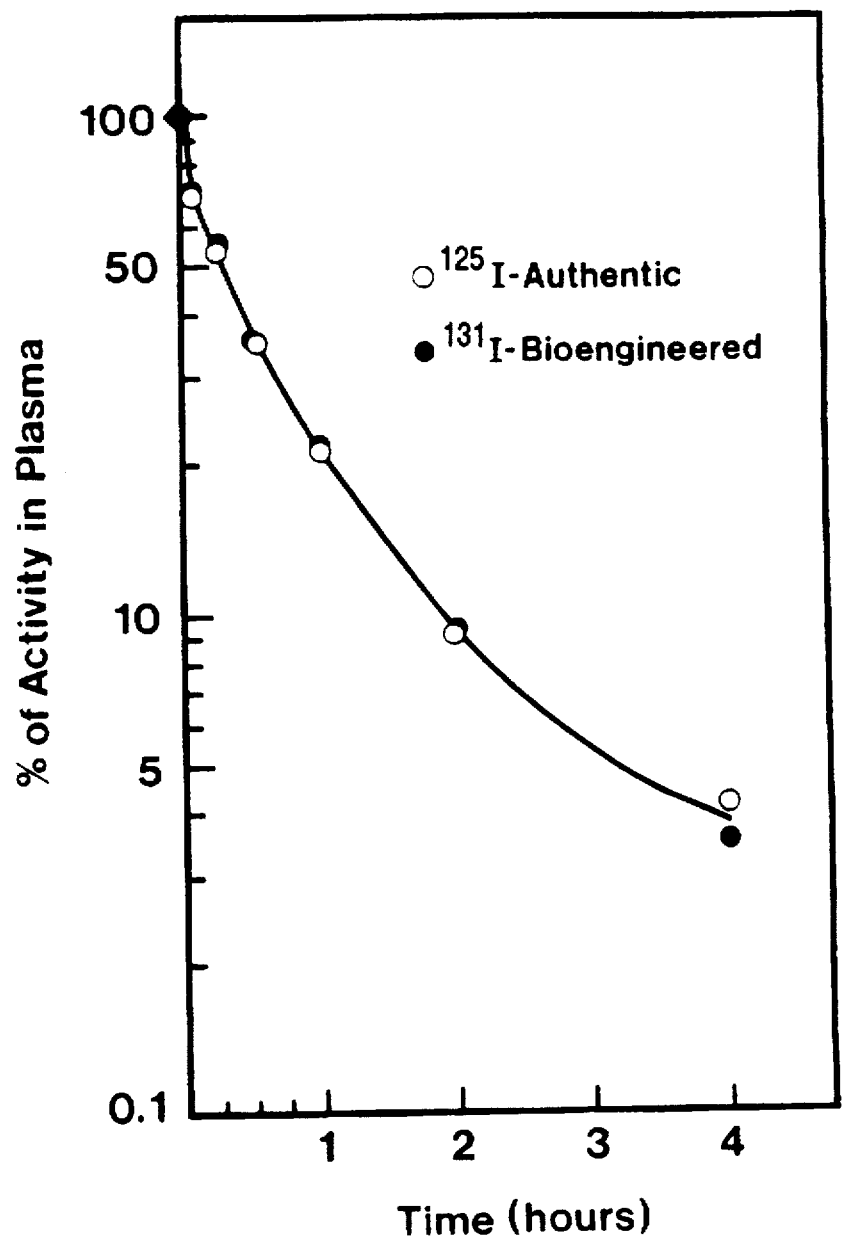

FIG. 31. Clearance of Iodinated ApoE from Rabbit Plasma.

Bioengineered and authentic ApoE were incubated at 37° for 30 minutes with 1 ml of rabbit plasma prior to injection of the mixture into a vein of a rabbit. Approximately 2 ml of blood was removed into a vial, containing EDTA, at the indicated time points and plasma prepared for counting. Counts are corrected for TCA soluble degradation products as described (33, following Example 15).

Figure 32:
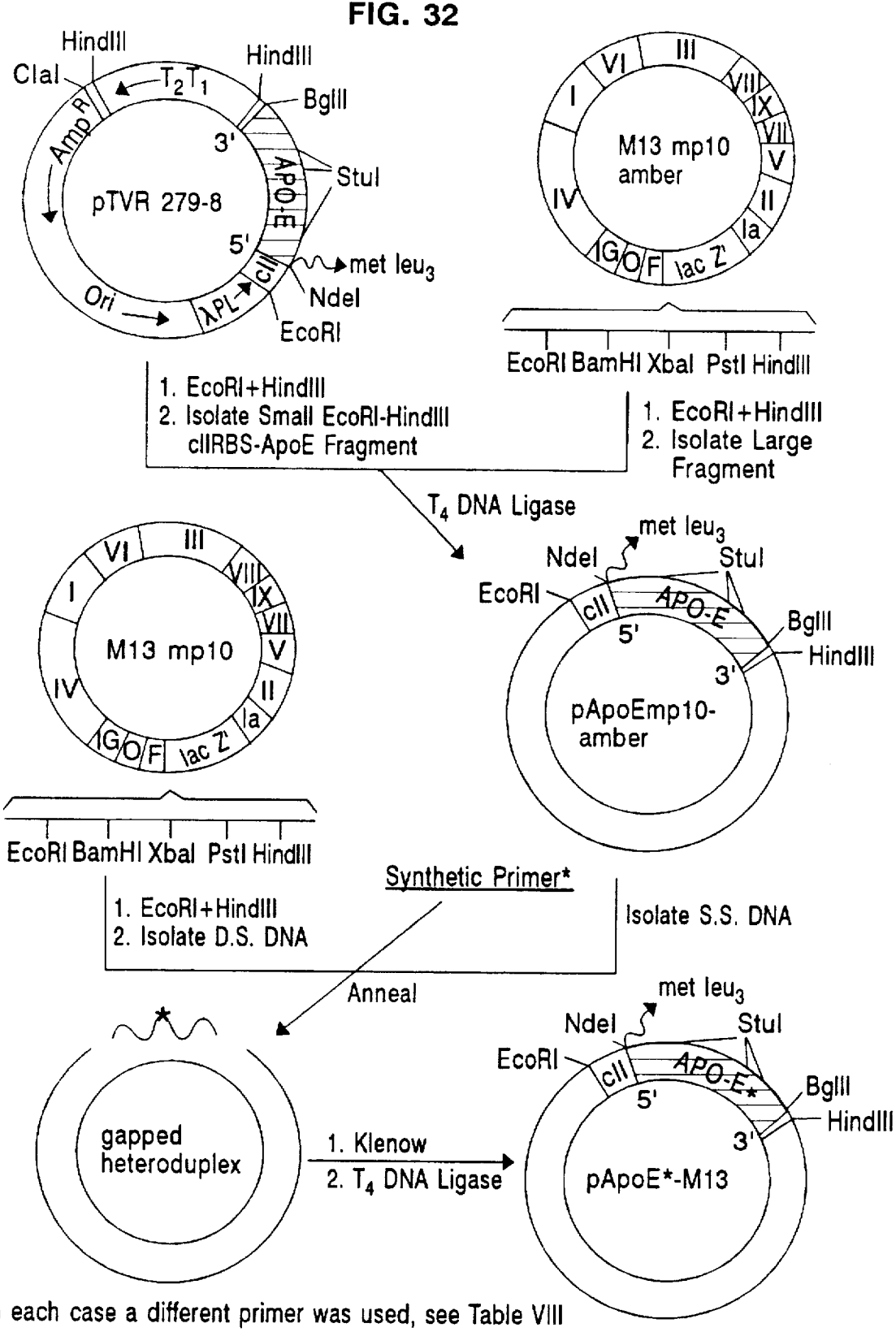

FIG. 32. General Scheme for Site—Directed Mutagenesis

An EcoRI-HindIII fragment which contains the met-leu-leu-leu-met ApoE gene immediately downstream from the cII ribosomal binding site was removed from pTVR 279-8 (ATCC No. 53216). It was then inserted into the large fragment produced by cleaving M13 mp10 amber with EcoRI and HindIII. The resultant pApoE-M13 was used in all the site-directed mutations described. The method of site-directed mutagenesis is as described by Bauer et al. (1985). (See Example 18). In each case a different synthetic oligonucleotide primer is used (Table VIII). Thus in the following figures the plasmids indicated pApoE*-M13 consist of a series of plasmids each with a different mutation in the ApoE sequence. The mutation was produced in each case by the synthetic nucleotide indicated in brackets.

Note that in all cases the first nucleotide of the NH$_2$-terminal lysine codon of mature authentic ApoE codon is taken as position 1 and similarly lysine is amino acid number 1. Thus the N-terminal methionine residue of the recombinant ApoE analog is minus 1.

Figure 33:
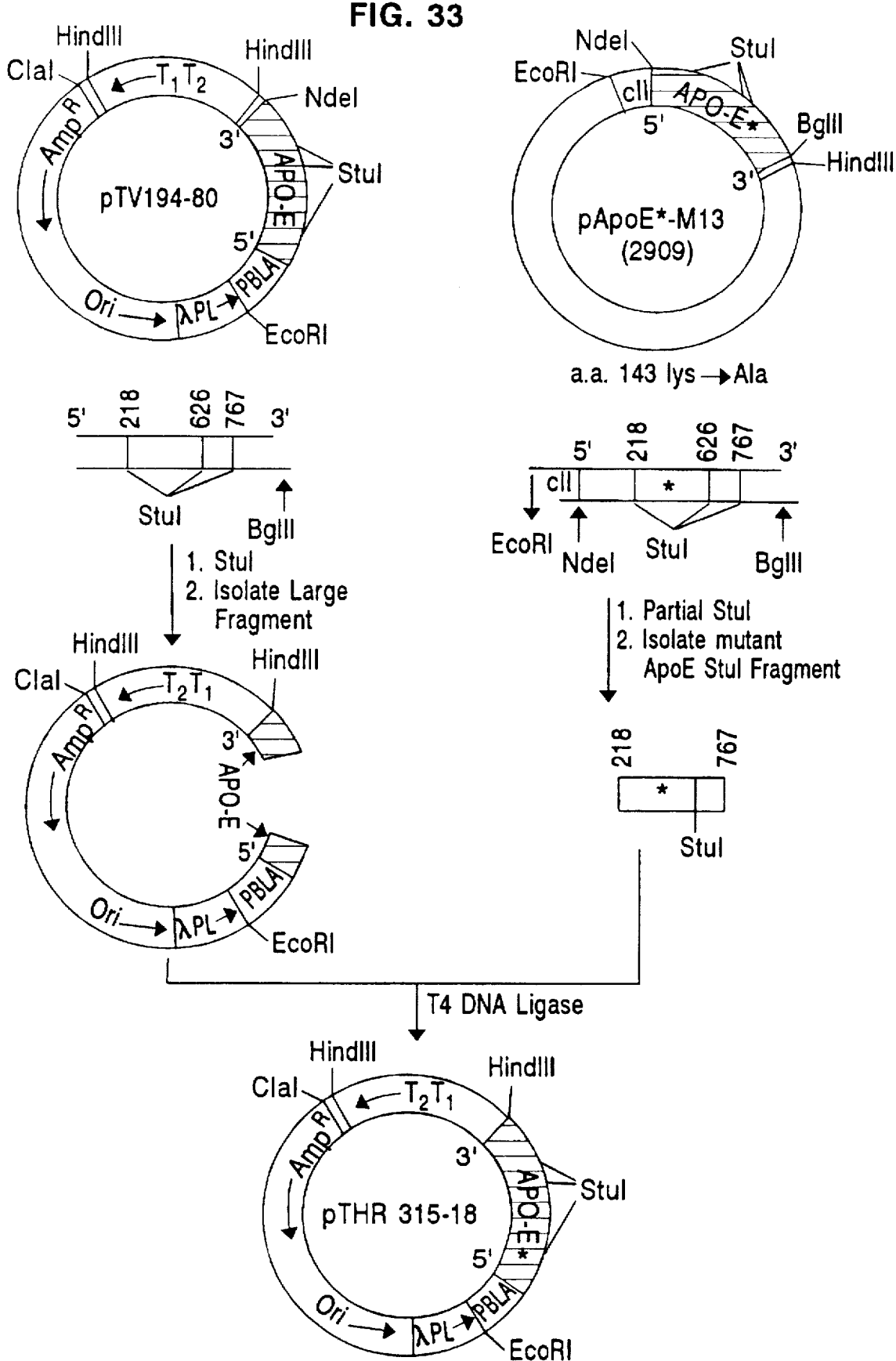

FIG. 33. Construction of pTHR 315-18

A mutation was created in pApoE-M13 by use of oligonucleotide primer number 2909 (Table VIII). This produced a mutation in amino acid 143 of ApoE (Lys→Ala). A partial StuI fragment of the mutated sequence (bp 218 to 766 inclusive, corresponding to amino acids 73 to 255 inclusive) was prepared and ligated into the large fragment produced by StuI digestion of plasmid pTV 194-80 (previously designated pTV 194). This produced a plasmid containing in 5'-3' order the $\lambda P_L$ promoter, the β lactamase promoter-ribosomal binding site and the mutated ApoE sequence. This plasmid was designated pTHR 315-18, and it expressed Met ApoE with a mutation (Lys→Ala) at position 143.

Figure 34:
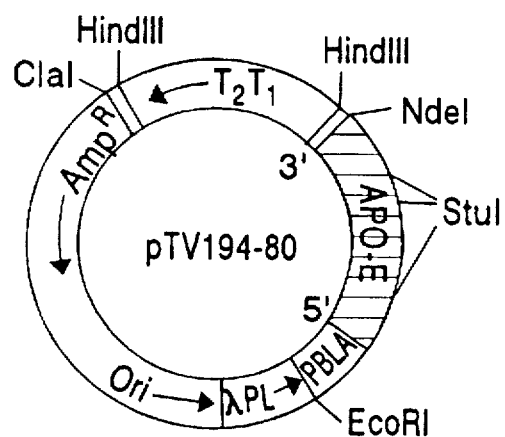
Figure 34:
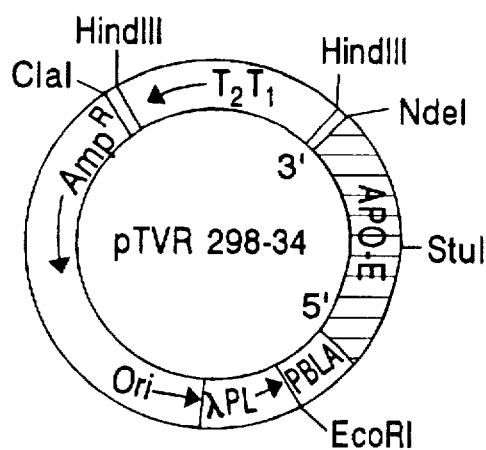

FIG. 34. Construction of pTVR 298-34

The plasmid pTV 194-80 was treated with StuI and the resulting large fragment was self-ligated to produce plasmid pTVR 298-34 which contains the ApoE gene with a deletion from nucleotides 218 to 766 (corresponding to amino acids 73 to 255 inclusive). It expresses a deleted ApoE analog of approximately 14 KD molecular weight.

Figure 35:
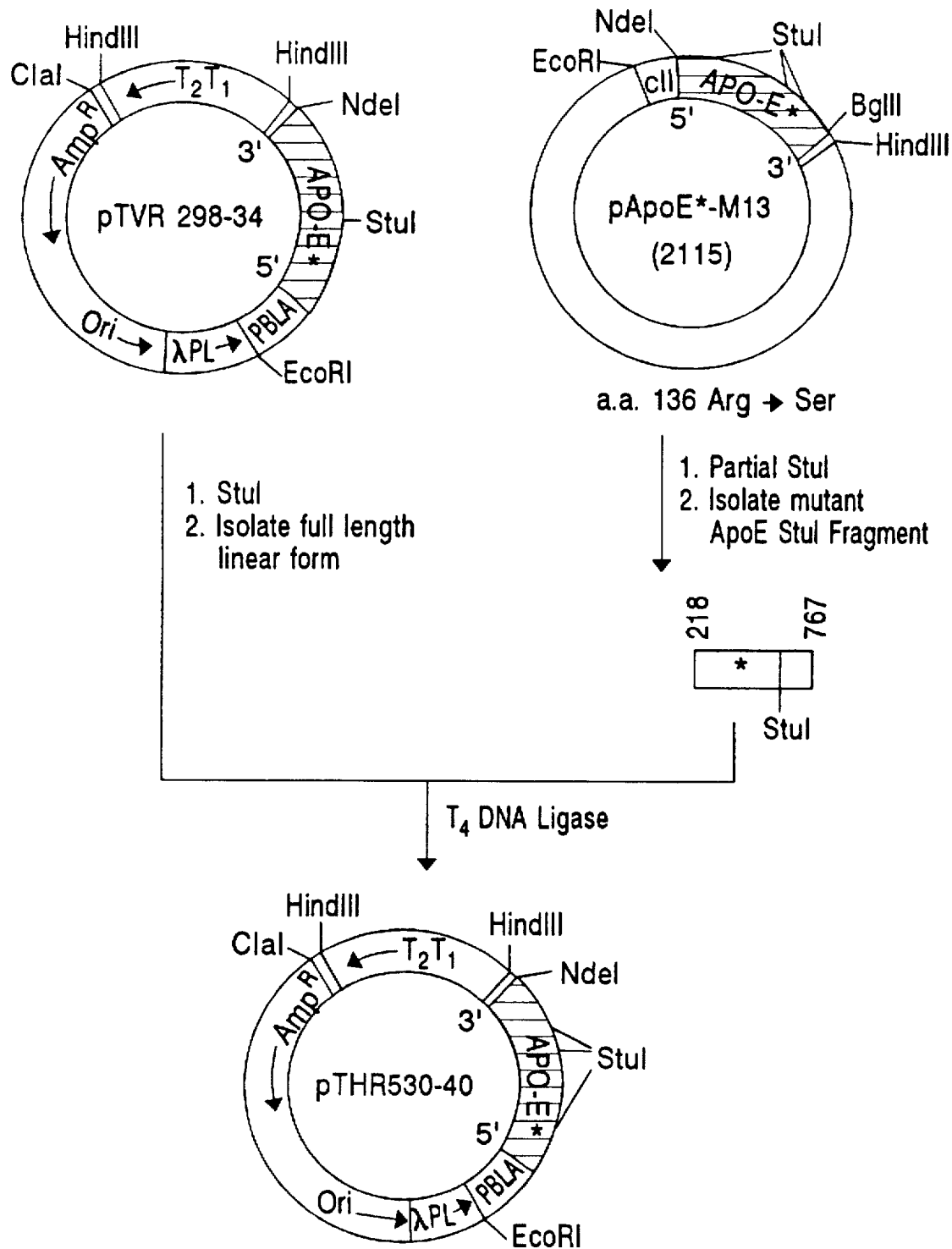

FIG. 35. Construction of pTHR 530-40

A mutation was created in pApoE-M13 by use of oligonucleotide primer number 2115 (Table VIII) which produces a mutation in amino acids number 136 (Arg→Ser). A partial StuI fragment (bp 218-766 inclusive), containing the mutation, was inserted into the full-length linear form of pTVR 298-34 produced by StuI digestion. This produced a plasmid containing the complete mutated ApoE sequence under the control of the $\lambda P_L$ promoter and the β lactamase promoter-ribosomal binding site. This plasmid, designated pTHR 530-40, expresses Met-ApoE with a mutation (Arg→Ser) at position 136.

Figure 36:
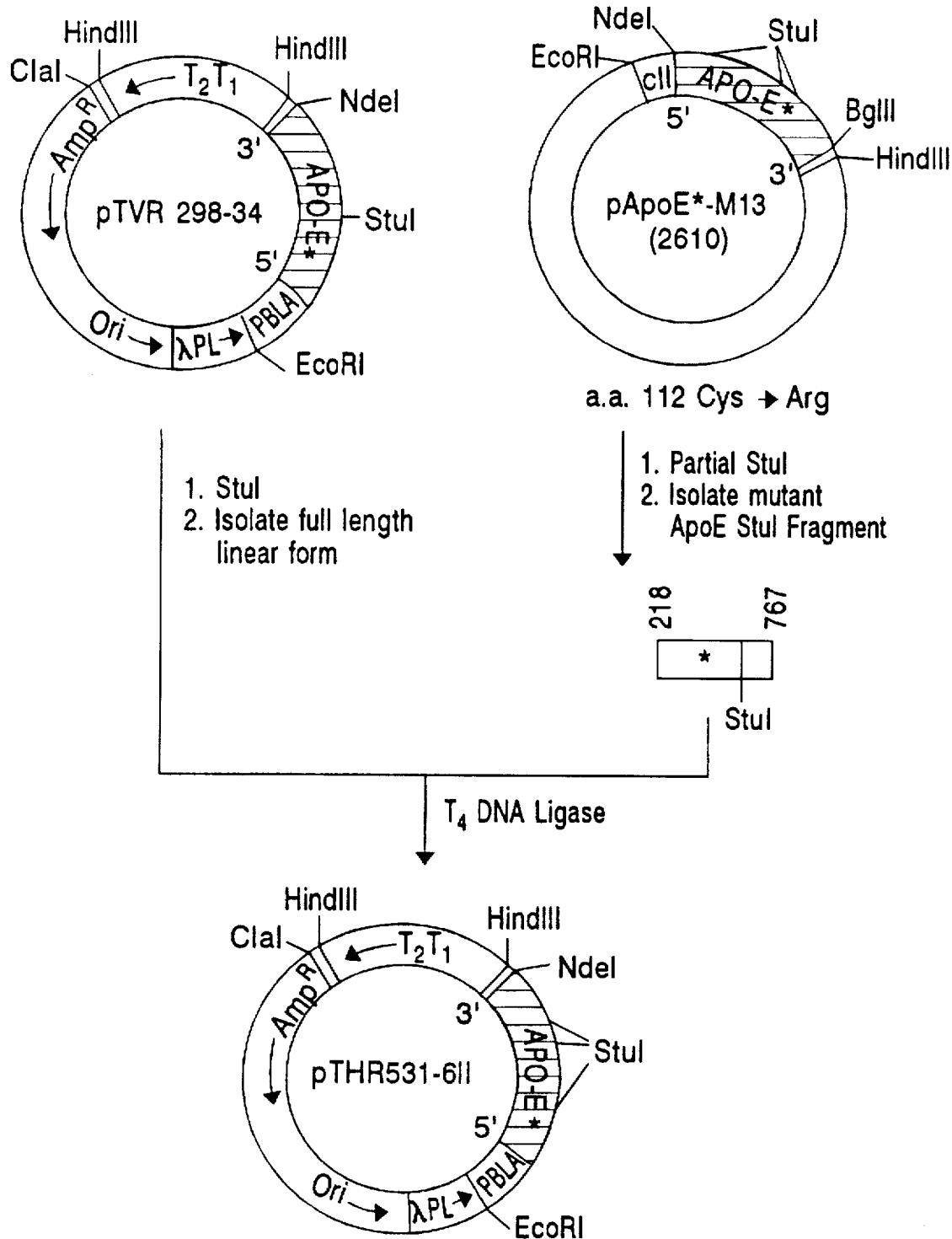

FIG. 36. Construction of pTHR 531-6II

A mutation was created in pApoE-M13 by use of oligonucleotide primer number 2610 (Table VIII) which produces a mutation at amino acid 112 (Cys→Arg). The partial StuI fragment (bp 218-766 inclusive) containing the mutation was ligated into the full-length linear form of pTVR 298-34 produced by StuI digestion. This produced a plasmid with the complete mutated ApoE sequence under the control of the $\lambda P_L$ promoter and the β lactamase promoter-ribosomal binding site. This plasmid, designated pTHR 531-6II expressed Met-ApoE protein with a mutation (Cys→Arg) at position 112).

Figure 37:
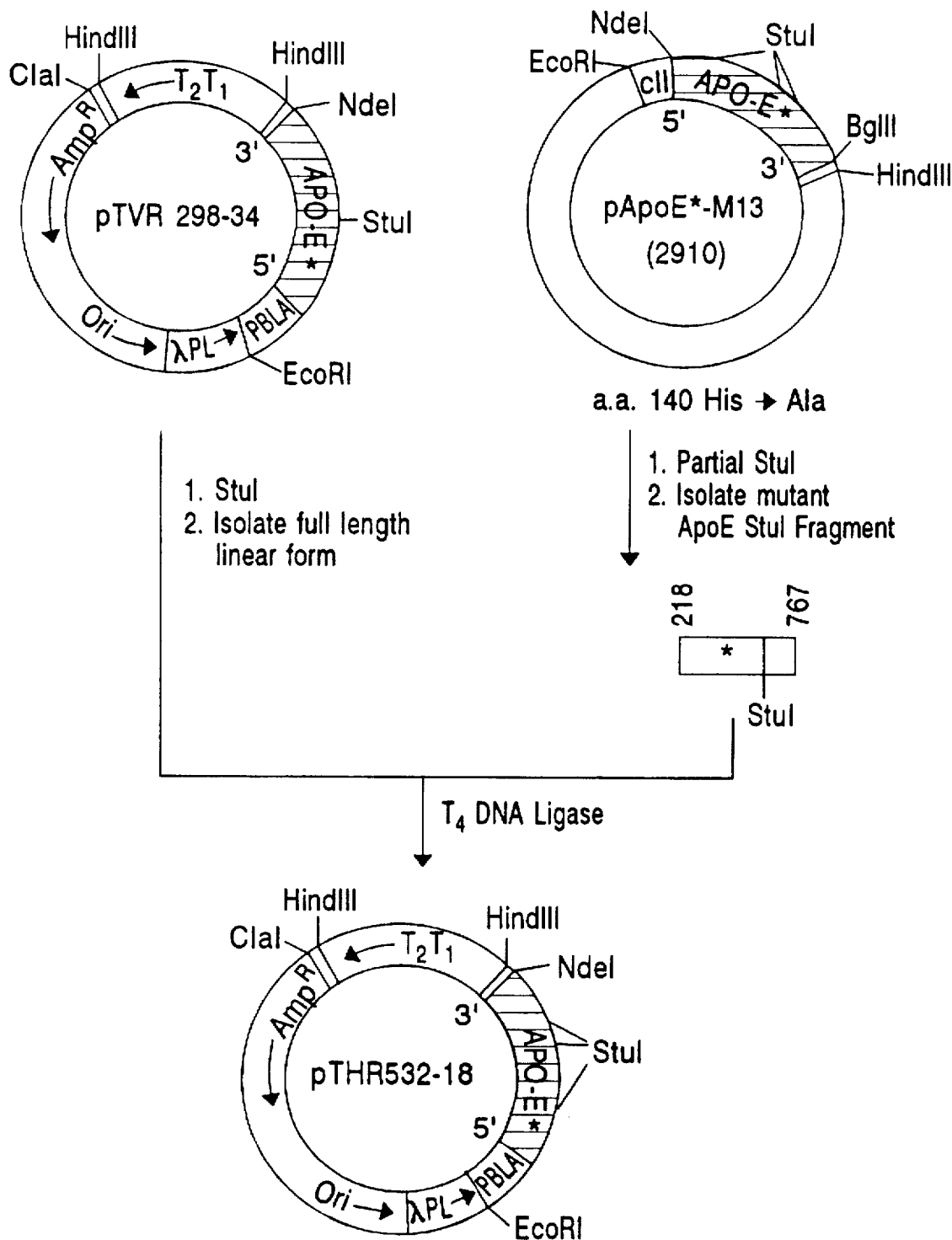

FIG. 37. Construction of pTHR 532-18

A mutation was created in pApoE-M13 by use of oligonucleotide primer number 2910 (Table VIII), which produces a mutation in amino acid 140 (His→Ala). The partial StuI fragment (bp 218-766 inclusive) containing the mutation was ligated into the full-length linear form of pTVR 298-34 produced by StuI digestion. This produced a plasmid with the complete mutated ApoE sequence under the control of the $\lambda P_L$ promoter and the β lactamase promoter-ribosomal binding site. This plasmid, designated pTHR 532-18, expressed Met-ApoE with a mutation (His→Ala) at position 140.

Figure 38:
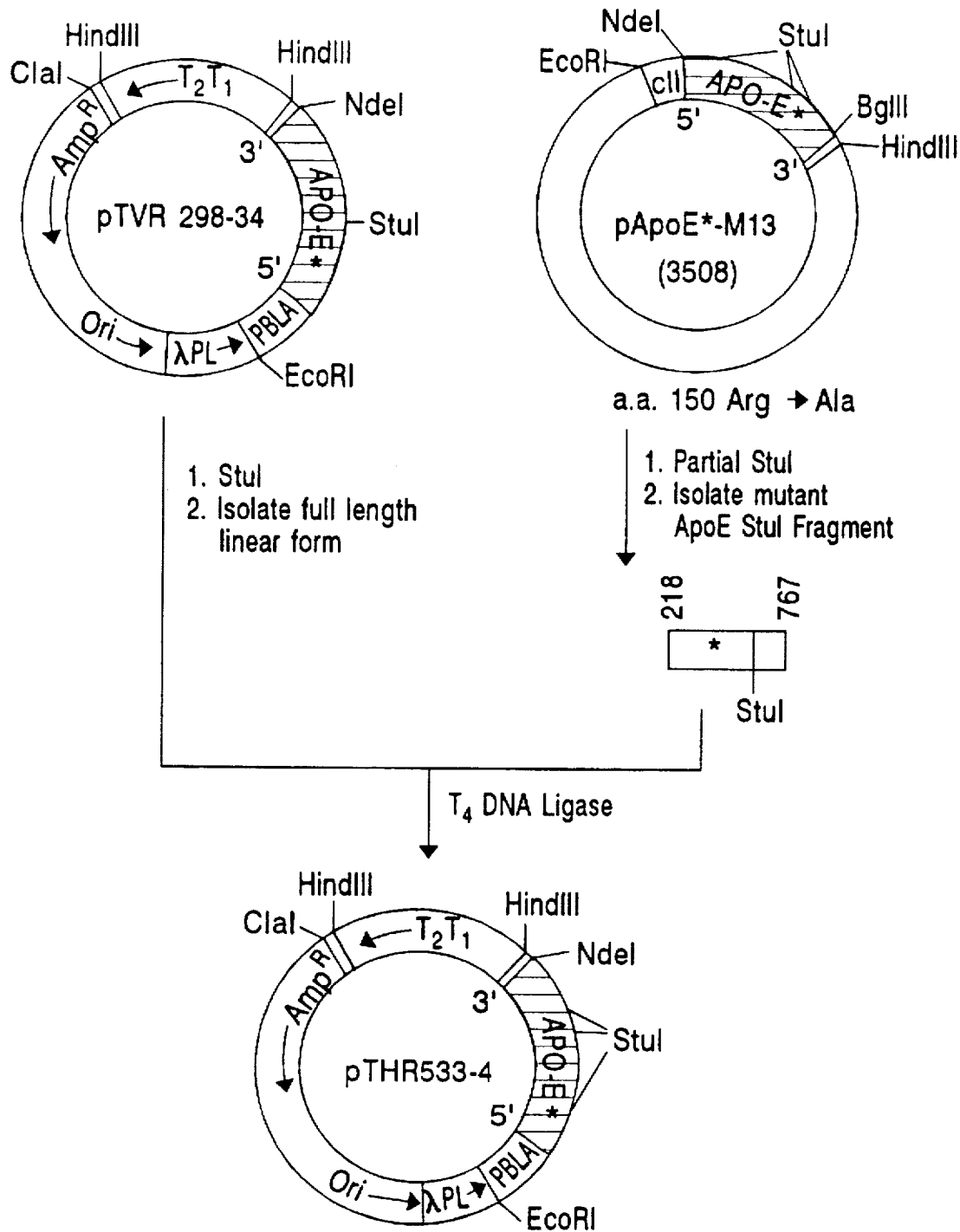

FIG. 38. Construction of pTHR 533-4

A mutation was created in pApoE-M13 by use of oligonucleotide primer number 3508 which produces a mutation in amino acid 150 (Arg→Ala). The partial StuI fragment (bp 218-766 inclusive) containing the mutation was ligated to the full-length linear form of pTVR 298-34 produced by StuI digestion. This produced a plasmid containing the complete mutated ApoE sequence under the control of the $\lambda P_L$ promoter and the β lactamase promoter-ribosomal binding site. This plasmid, designated pTHR 533-4 expressed met-ApoE with a mutation (Arg→Ala) at position 150.

Figure 39:
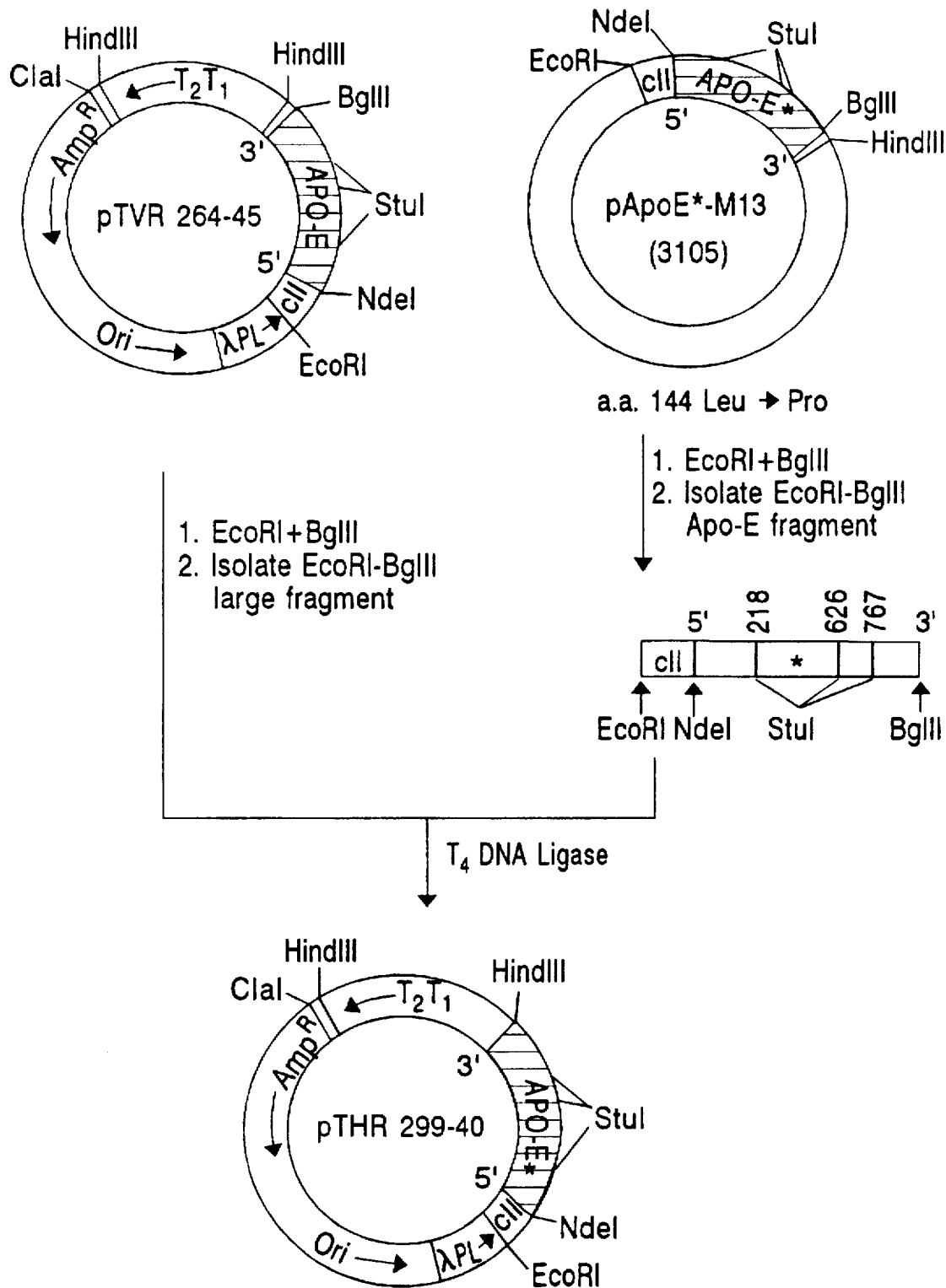

FIG. 39. Construction of pTHR 299-40

A mutation was created in pApoE-M13 by use of oligonucleotide primer number 3105 (Table VIII), which produces a Leu→Pro mutation at amino acid number 140. An EcoRI-BglII fragment of this plasmid, containing the whole mutated met-leu-leu-leu-met-ApoE sequence adjacent to the cII ribosomal binding site, was ligated to the EcoRI-BglII large fragment of pTV 264-45. This produced a plasmid containing, in 5' to 3' order, the $\lambda P_L$ promoter, the cII ribosomal binding site, and a mutated met-leu-leu-leu-met-ApoE sequence. This plasmid, designated pTHR 299-40, expressed met-leu-leu-leu-met-ApoE with a mutation (Leu→Pro) at position 140.

Figure 40:
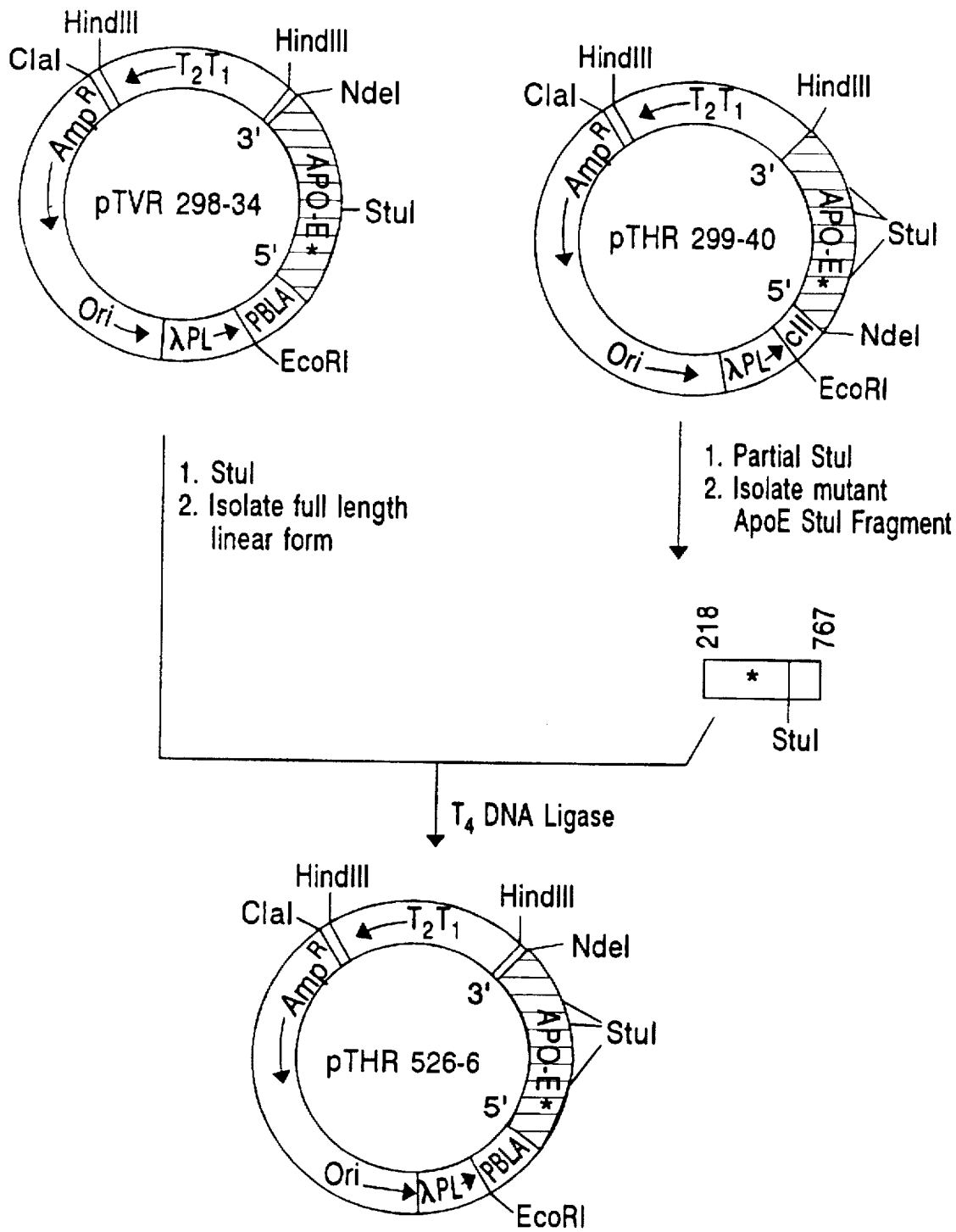

FIG. 40. Construction of pTHR 526-6

The StuI fragment (bp 218-766 inclusive) mutated at amino acid 144 (Leu→Pro) was isolated from pTHR 299-40 and ligated into the full length linear form of pTVR 298-34 obtained after StuI digestion of pTVR 298-34. This produced a plasmid which contained in 5' to 3' order the $\lambda P_L$ promoter, the β lactamase ribosomal binding site and the complete mutated ApoE sequence. This plasmid, designated pTHR 526-6 expresses Met-ApoE protein with a mutation (Leu→Pro) at position 144.

Figure 41:
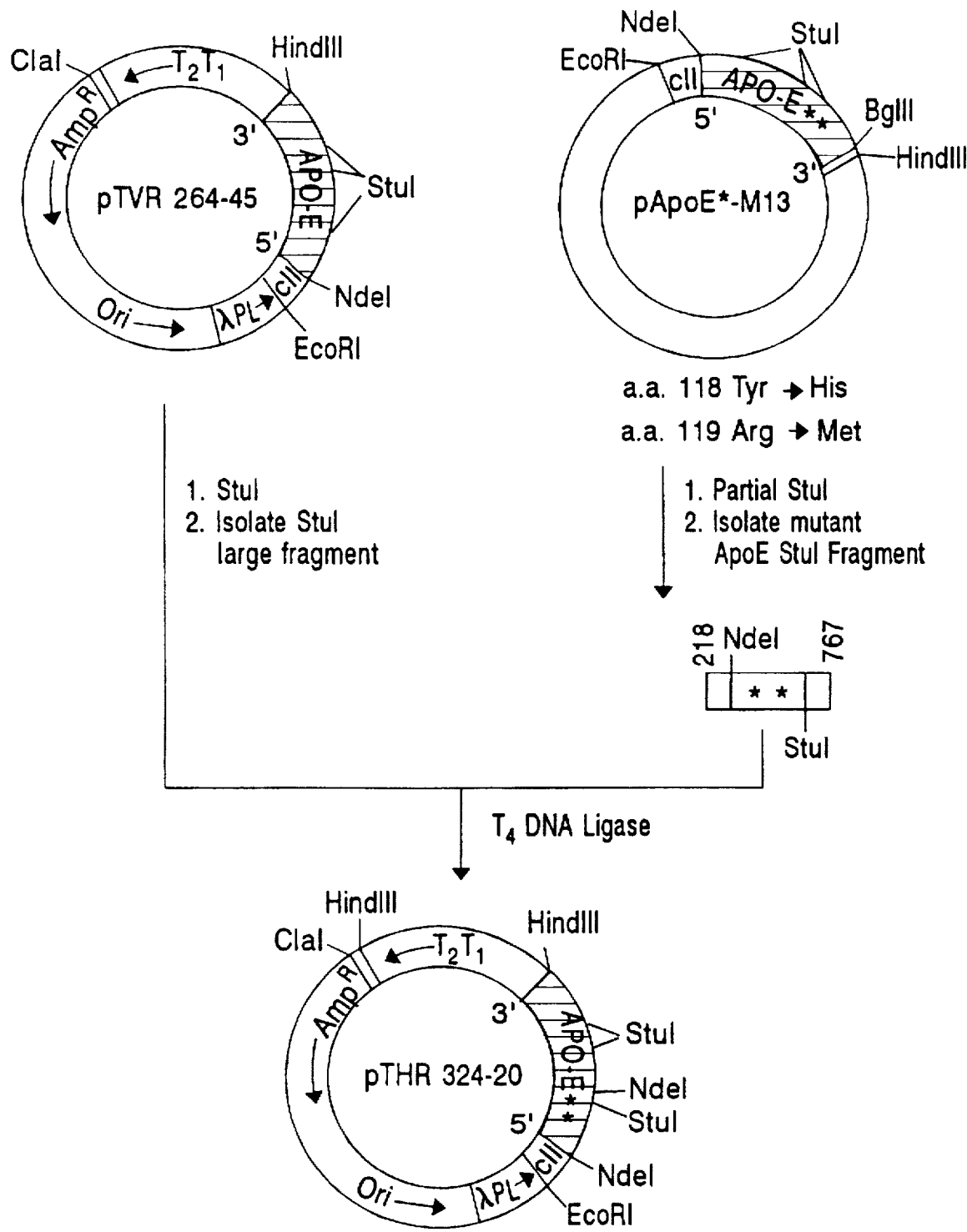

FIG. 41. Construction of pTHR 324-20

A mutation was created in pApoE-M13 by use of oligonucleotide primer number 2427 (Table VIII), which produced a Tyr→His and an Arg→Met mutation at positions 118 and 119 respectively. This created a new NdeI site at this position in addition to the NdeI site immediately adjacent to the 5' end of the ApoE sequence. A partial StuI fragment (bp 218-766 inclusive) containing the mutated sequence was ligated to the large StuI fragment from pTV 264-45, creating a plasmid which contains, in 5' to 3' order, the $\lambda P_L$ promoter, the cII ribosomal binding site and the mutated met-ApoE sequence. This plasmid, designated pTHR 324-20, expresses a mutated met-ApoE protein with mutations at amino acids 118 and 119.

Figure 42:
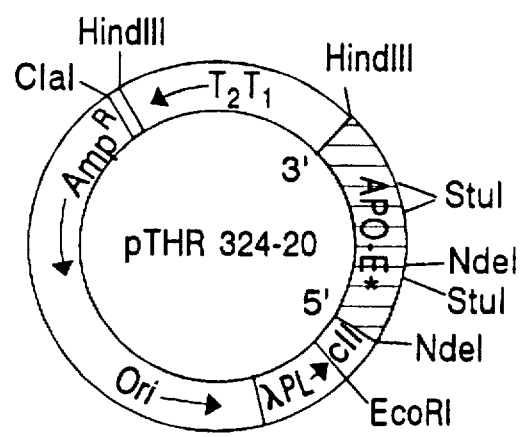
Figure 42:
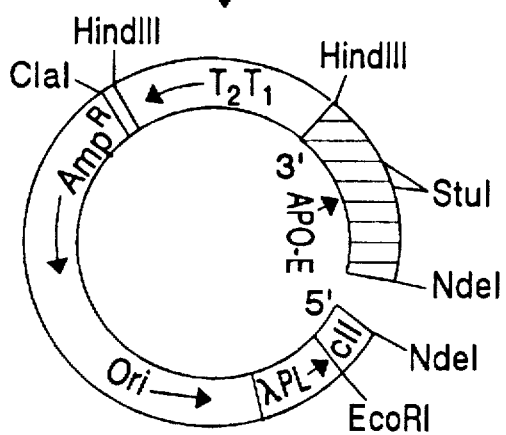
Figure 42:
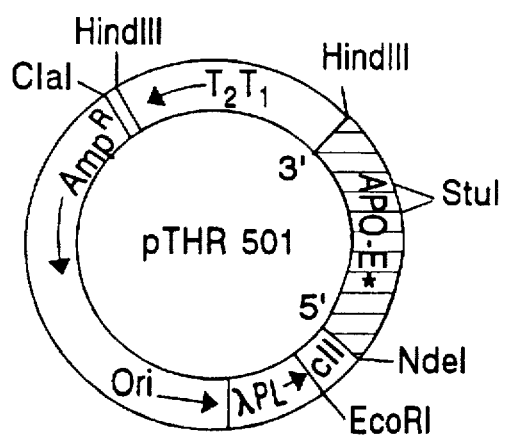

FIG. 42. Construction of pTHR 501

The plasmid pTHR 324-20 was treated with NdeI and the resulting large fragment was self-ligated. Ths resulted in the deletion of the first 119 amino acids at the N-terminal end of the ApoE sequence. The resulting plasmid, containing in 5' to 3' order the $\lambda P_L$ promoter, the cII ribosomal binding site and the deleted met-ApoE sequence was designated pTHR 501, and does not express detectable ApoE-type protein.

Figure 43:
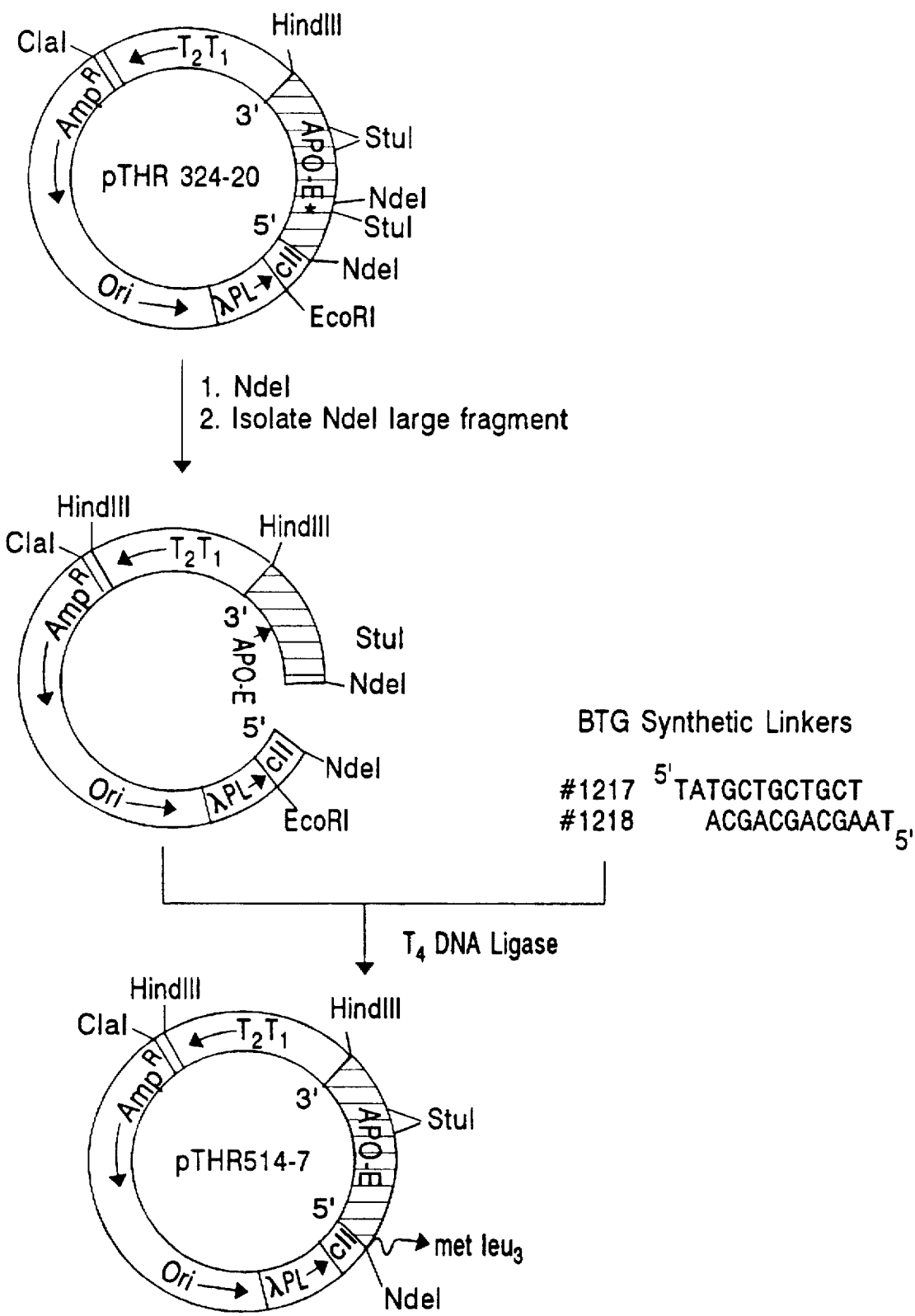

FIG. 43. Construction of pTHR 514-7

Plasmid pTHR 324-20 was treated with NdeI and the resulting large fragment was attached by $T_4$ ligase to synthetic linkers No. 1217 and 1218 (see FIG. 25 and Example 11). This produced plasmid pTHR 514-7 which is another N-terminal deletion mutant but with the addition of the sequence coding for met-leu-leu-leu-met at the N-terminal end. This plasmid, containing the deleted met-leu-leu-leu-met-ApoE sequence under the control of the cII ribosomal binding site, expresses a deleted ApoE-type protein of approximately 20 KD molecular weight.

Figure 44:
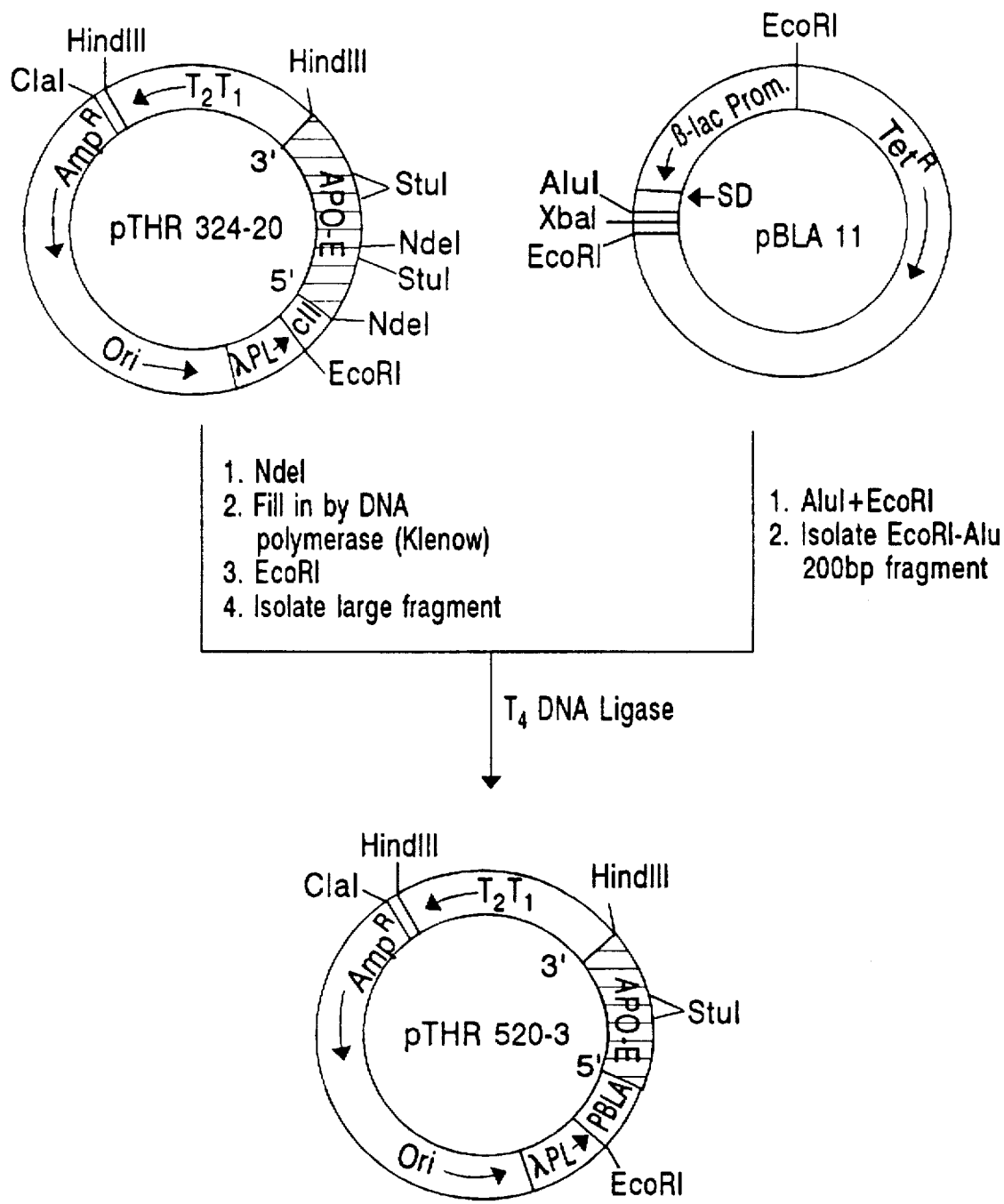

FIG. 44. Construction of pTHR 520-3

Plasmid pTHR 324-20 was NdeI-treated, filled in by the Klenow reaction and EcoRI-treated. The resulting large fragment, deleted for the cII ribosomal binding site and the first 119 amino acids of ApoE, was ligated to the EcoRI-AluI 200 bp fragment from pBLA 11, which contains the β lactamase promoter ribosomal binding site (pBLA). This produces a plasmid designated pTHR 520-3, which contains in 5' to 3' order the A $P_L$ promoter, the β lactamase promoter ribosomal binding site and the deleted ApoE sequence. This expresses deleted ApoE-type protein.

Figure 45:
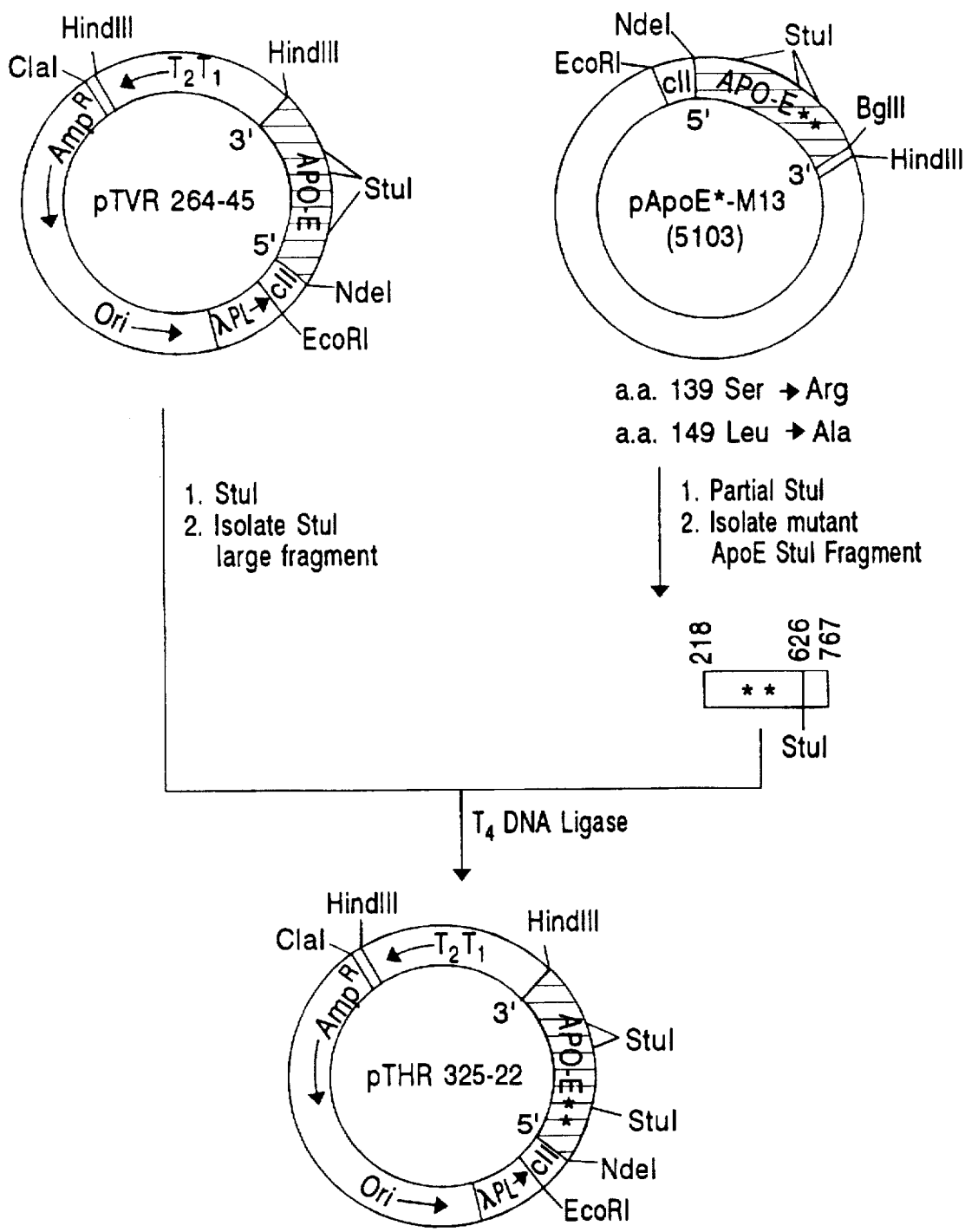

FIG. 45. Construction of pTHR 325-22

A double mutation was created in pApoE-M13 by use of oligonucleotide primer number 5103 (Table VIII), which produced a Ser→Arg mutation and a Leu→Ala mutation at amino acid positions 139 and 149 respectively. A partial StuI fragment (bp 218-766 inclusive) containing the double mutation was ligated to the large StuI fragment of pTV 264-45. The resulting plasmid contains in 5' to 3' order the $\lambda P_L$ promoter, the cII ribosomal binding site and the mutated met-ApoE sequence. This plasmid was designated pTHR 325-22 and it expresses met-ApoE with the double mutation indicated.

Figure 46:
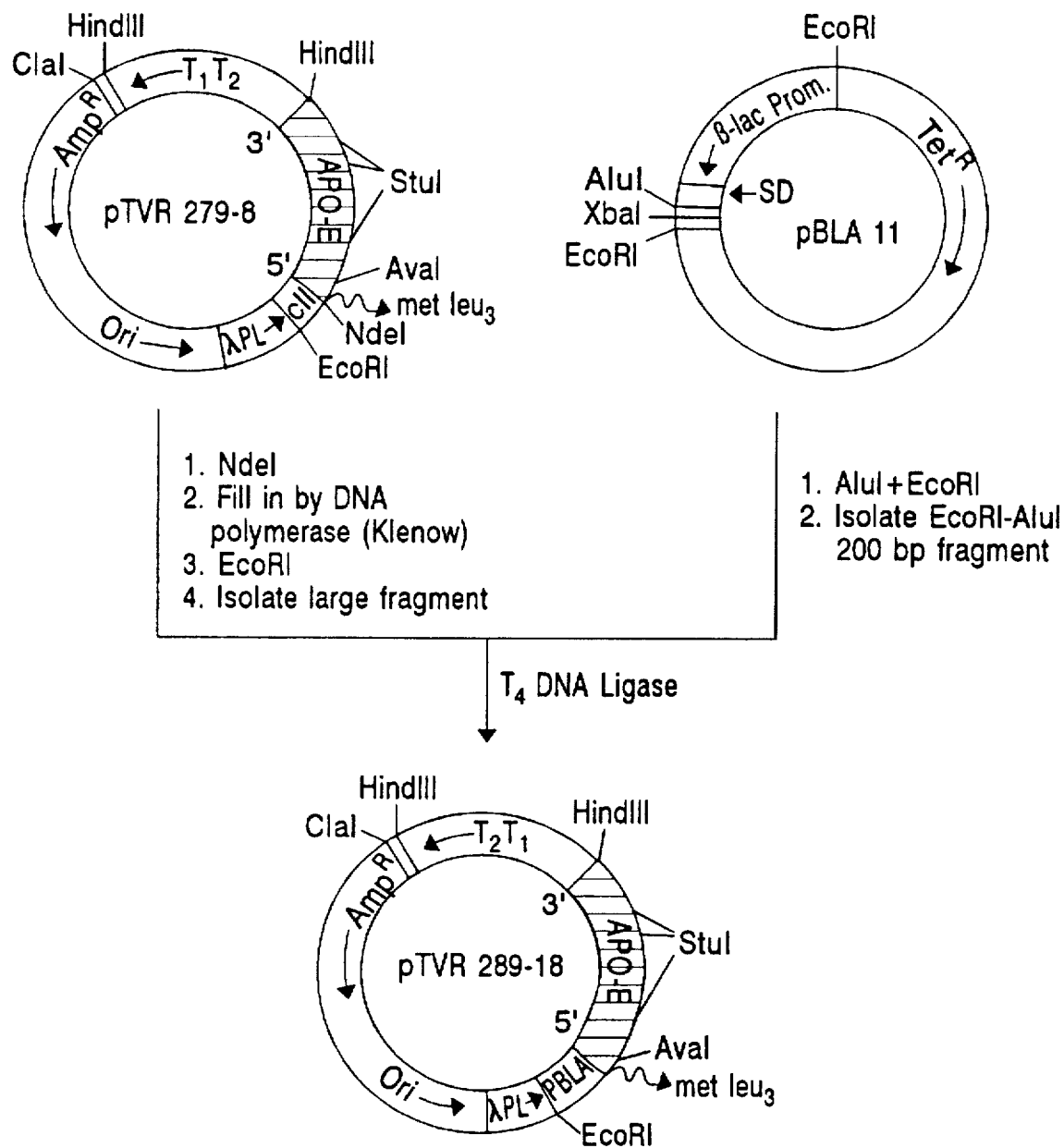

FIG. 46. Construction of pTVR 289-18

The cII ribosomal binding site was removed from pTVR 279-8 by NdeI digestion, Klenow fill-in and EcoRI digestion, and the large fragment produced was isolated. This fragment was ligated to the EcoRI-AluI 200 bp fragment from pBLA11 (ATCC No. 39788) which contains tne promoter and ribosomal binding site of β lactamase (designated pBLA). The resulting plasmid contains in 5' to 3' order the $\lambda P_L$ promoter, the β lactamase promoter-ribosomal binding site and the sequence for met-leu-leu-leu-met-ApoE, with deletion of the NdeI site at the 5' end of the ApoE sequence. This plasmid, designated pTVR 298-18, expresses met-leu-leu-leu-met-ApoE.

Figure 47:
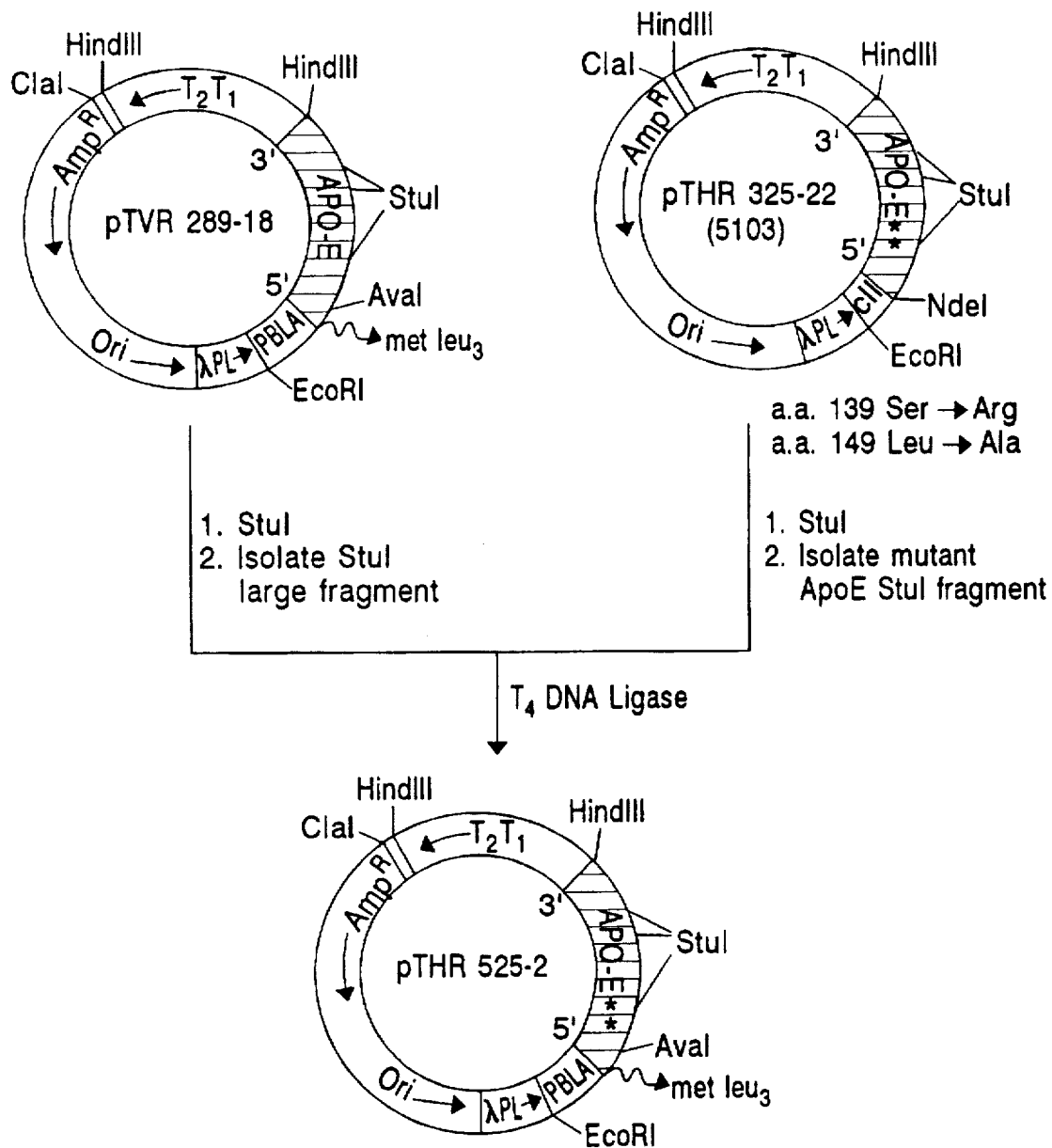

FIG. 47. Construction of pTHR 525-2

The StuI fragment (bp 218-766 inclusive) containing the double mutation from pTHR 325-22 was ligated into the large StuI fragment from pTVR 289-18. This produced a plasmid which contains in 5' to 3' order the A $P_L$ promoter, the β lactamase promoter-ribosomal binding site and the mutated met-leu-leu-leu-met-ApoE sequence. This plasmid, designated pTHR 525-2, directs the expression of met-leu-leu-leu-met-ApoE containing the double mutation of Ser→Arg and Leu→Ala at positions 139 and 149 respectively.

Figure 48:
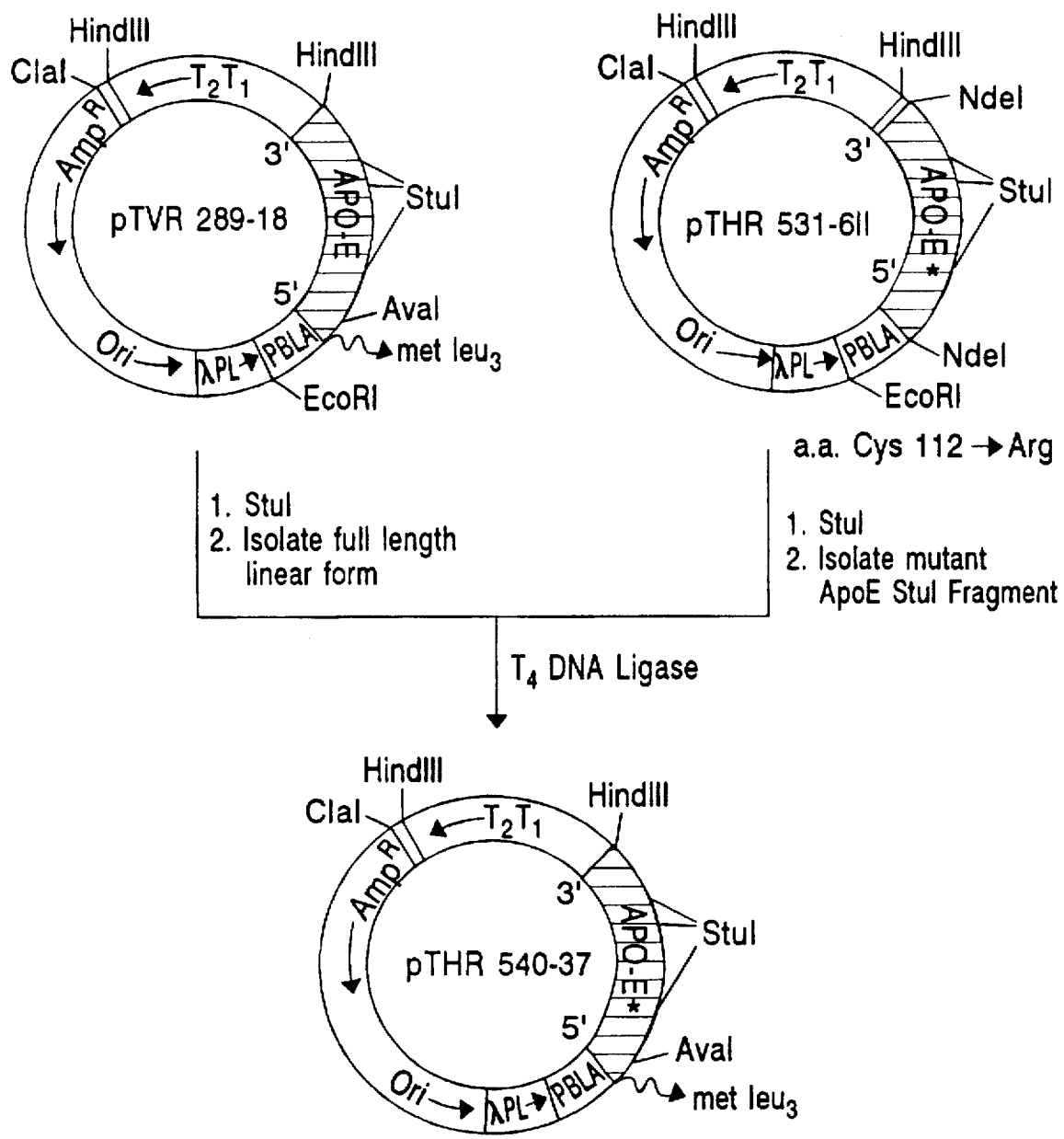

FIG. 48. Construction of pTHR 540-37

The partial StuI fragment (bp 218-766 inclusive) from pTHR 531-6II, containing the mutation Cys→Arg at amino acid 112, was ligated to the large StuI fragment (bp 218-766 inclusive) of pTVR 289-18. This produced a plasmid which contains in 5' to 3' order the $\lambda P_L$ promoter, the β lactamase promoter-ribosomal binding site and the mutated met-leu-leu-leu-met-ApoE sequence. This plasmid, designated pTHR 540-37, directs the expression Of met-leu$_3$-met-ApoE with a mutation (Cys→Arg) at position 112.

Figure 49:
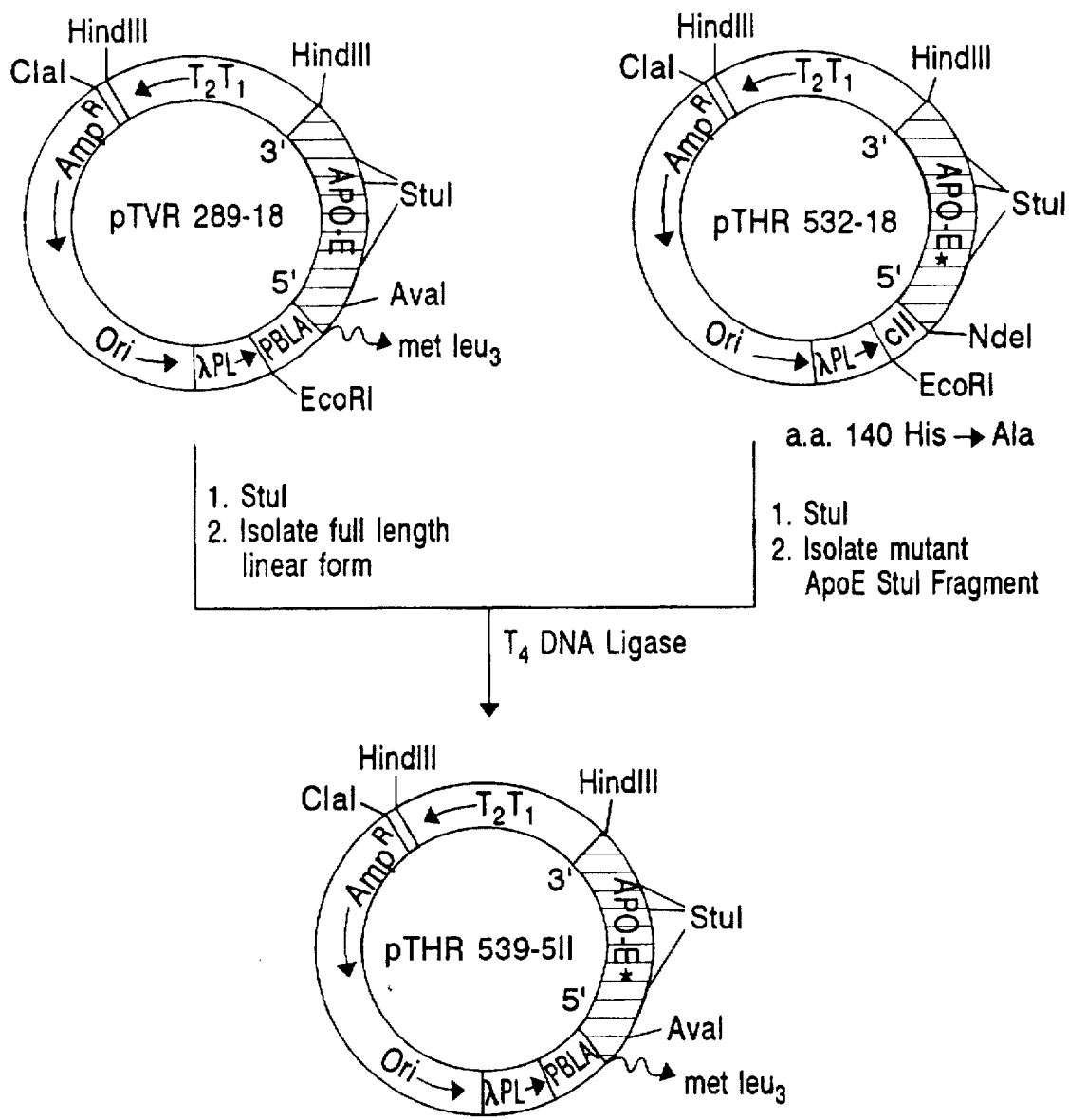

FIG. 49. Construction of pTHR 539-5II The mutated StuI fragment (bp 218-766 inclusive) of pTHR 532-18 (which contains the His→Ala mutation at amino acid 140) was ligated to the large fragment after StuI digestion of pTVR 289-18. This produced a plasmid, designated pTHR 539-5II which contains in 5' to 3' order the $\lambda P_L$ promoter, the β lactamase promoter-ribosomal binding site and the mutated met-leu-leu-leu-met-ApoE sequence. This plasmid expresses met-leu-leu-leu-met-ApoE with a mutation (His→Ala) at position 140.

Figure 50:
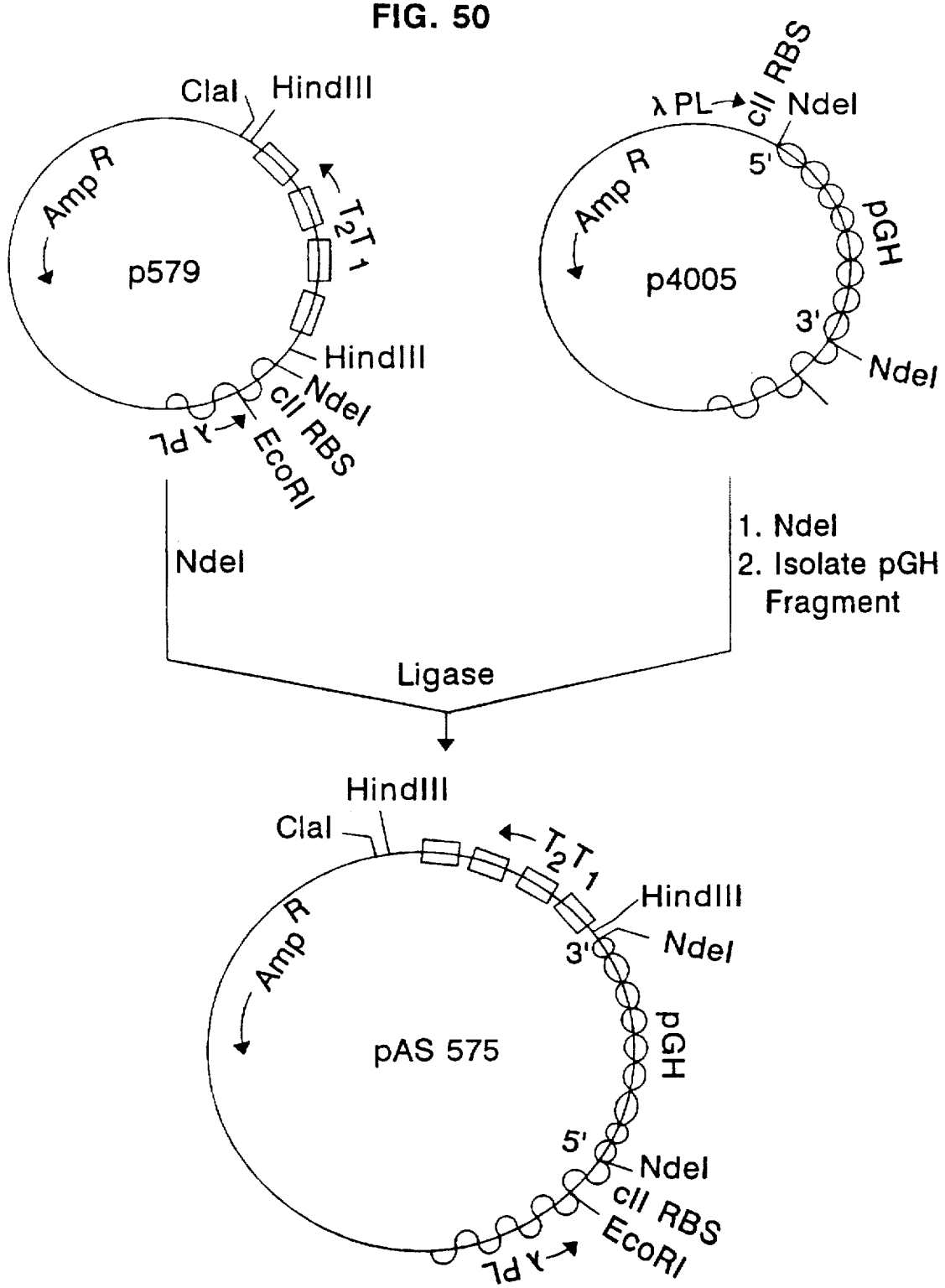

FIG. 50. Construction of pAs 575 p4005 was digested with NdeI. The NdeI-NdeI fragment containing the pGH CDNA was isolated and inserted into the unique NdeI site of the expression vector p579 (FIG. 19) which had been digested with NdeI. The resulting plasmid, pAs 575 expresses an analog of natural porcine growth hormone having a methionine residue at the N-terminus.

Figure 51:
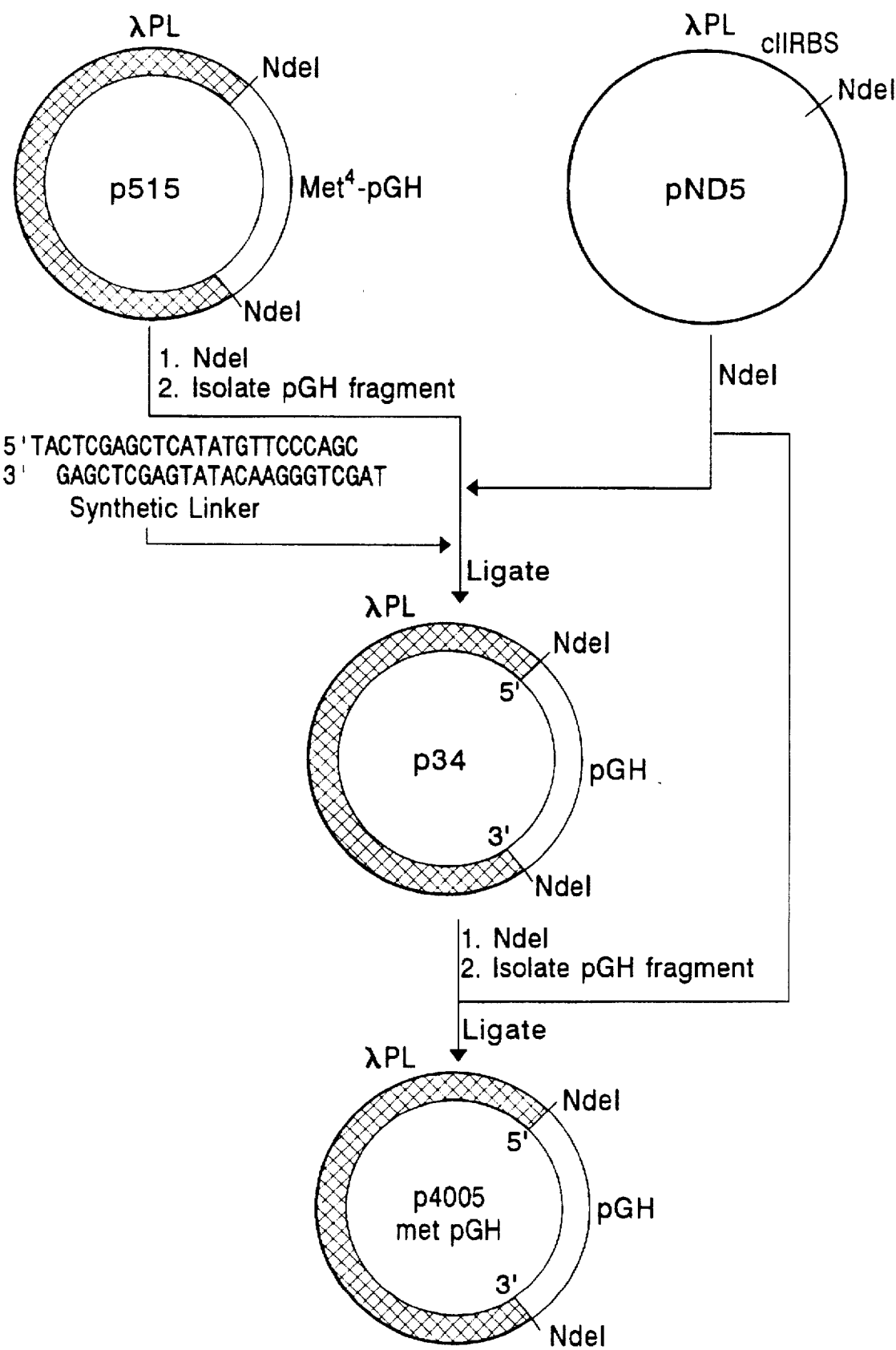

FIG. 51. Construction of p4005 p4005 was constructed from p34 which was constructed from plasmid p515.

Plasmid p515, which directs the expression of Met$^4$-pGH was cleaved with NdeI. The NdeI fragment containing the pGH cDNA was isolated and ligated to a synthetic linker, and to pND5 cleaved with NdeI. The resulting plasmid, p34, contains cDNA encoding met-pGH. However in p34, the ATG initiation codon is not located at the proper distance from the ribosomal binding site.

p34 was cleaved with NdeI, the pGH cDNA fragment was isolated and ligated to pND5 cleaved with NdeI. The resulting plasmid p4005, containing DNA identical in sequence to pGH cDNA, directs the expression of Met-pGH.

DETAILED DESCRIPTION OF THE INVENTION

A vector has been developed which enables the achievement of enhanced levels of gene expression and polypeptide production. The vector is a double-stranded DNA molecule. Upon introduction into a suitable bacterial host cell containing the thermolabile repressor $C_I$ the vector renders the host cell capable, upon increasing the temperature of the host cell to a temperature at which the repressor is inactivated, of effecting expression of a desired gene inserted into the vector and production of polypeptide encoded by the gene.

The vector includes in 5' to 3' order the following:

- a DNA sequence which contains the promoter and operator $P_LO_L$ from lambda bacteriophage;
- the N utilization site for binding antiterminator N protein;
- a first restriction enzyme site permitting replacement of the DNA sequence containing the ribosomal binding site which follows thereafter;
- a DNA sequence which contains a ribosomal binding site for rendering the mRNA of the desired gene capable of binding to ribosomes within the host cell;
- an ATG initiation codon or a DNA sequence which is converted into an ATG initiation codon upon insertion of the desired gene into the vector;
- a second restriction enzyme site for inserting the desired gene into the vector in phase with the ATG initiation codon; and
- a DNA sequence which contains a $T_1T_2$ rRNA transcription termination sequence.

The vector also includes a DNA sequence which contains an origin of replication from a bacterial plasmid capable of autonomous replication in the host cell and a DNA sequence which contains a gene associated with a selectable or identifiable phenotypic trait which is manifested when the vector is present in the host cell. The distance between the 3' end of the $P_LO_L$ promoter and operator sequence and the 5' end of the N utilization site is less than about 80 base pairs and the distance between the 3' end of the N utilization site and the 5' end of the ribosomal binding site is less than about 300 base pairs.

Another component of the vector is a first restriction enzyme site permitting replacement of the DNA sequence containing the ribosomal binding site which follows thereafter. Numerous such sites may be used. Suitable sites include EcoRI.

Yet another component of the vector is a second restriction enzyme site for insertion of desired genes into the vector in phase with the ATG initiation codon. Numerous such sites may be used. Suitable sites include NdeI, ClaI, HindIII, SmaI, BglII, XbaI, SacI and AluI.

Generally it is desirable that the second restriction enzyme site also function as the second restriction site necessary to permit replacement of the DNA sequence containing the ribosomal binding site. If the second restriction site is not also used for this purpose then the vector of this invention must also include a third restriction enzyme site after the ribosomal binding site but prior to the second restriction site.

Preferably the vector contains two unique restriction enzyme sites. The first site permits replacement of the DNA sequence containing the ribosomal binding site. The second site permits insertion of the desired gene into the vector in phase with the ATG initiation codon. In a presently preferred embodiment, EcoRI is the first restriction enzyme site and NdeI is the second restriction enzyme site.

A further component of the vector is a $T_1T_2$ rRNA transcription termination sequence. Preferably, the $T_1T_2$ rRNA transcription termination sequence is less than about 100 base pairs from the 3' end of the second restriction enzyme site. More preferably, the $T_1T_2$ rRNA transcription termination sequence is less than about 20 base pairs from the 3' end of the second restriction enzyme site.

The preferred host for use with the vector is *Escherichia coli*. The presently preferred strains are A1637, A1645, A2602, A2097 and A1563. A2097 is presently the most preferred strain for the expression of the gene which produce:

1) an analog of bGH having the amino acid sequence met-asp-gln added to the amino-terminus of the phenylalanine form of authentic bGH; or
2) an analog of cGH having the amino acid methionine added to the amino-terminus of the phenylalanine form of natural cGH; or
3) ApoE and analogs of ApoE.

A1645 is presently the most preferred strain for expression of other genes. These strains have been deposited with the American Type Culture Collection in Rockville, Md., U.S.A. containing various plasmids as described more full hereinafter. All such deposits were made pursuant to the Budapest Treaty on the International Recognition of the Deposit of Microorganisms except that pBR322 and pBRM are freely available from the American Type Culture Collection as ATCC Nos. 37017 and 37283, respectively, and D4 was deposited under ATCC No. 31826 in connection with the filing of a U.S. patent application.

A1645 was obtained from A1637 by selection for Gal$^+$ (ability to ferment galactose) as well as loss of tetracycline resistance. It still contains the lambda expression system but part of the transposon has been removed by selection. Its phenotype is C600 r$^-$m$^+$ gal$^+$ thr$^-$ leu$^-$ lac$^-$ b1 ($\lambda$cI857 $\Delta$H1 $\Delta$Bam N+).

A2602 and A1563 are derived from SA500. Their phenotypes are SA500 his$^-$ile$^-$ gal$^+$ $\Delta$8($\lambda$cI857 $\Delta$H1 $\Delta$Bam N+) and SA500 his$^-$ ile$^-$ gal$^+$ $\Delta$8 lac ZxA21 ($\lambda$cI857 int2 xisl nutL3 $\Delta$H1), respectively. A2097 is derived from A1645. Its phenotype is A1645 lac $\Delta$XA21 proC:Tn10.

Prototrophic strains of *Escherichia coli* which enable high level polypeptide expression even when grown in a minimal media may also be used as hosts for the vectors of this invention. Preferred prototrophic strains include A4200 and A4255. Strain A4255 containing the plasmid p9200 has been deposited with the ATCC under Accession No. 53215. Even more preferred are biotin independent prototrophic strains such as A4346 containing the plasmid pHG44 which has been deposited with the ATCC under Accession No. 53218.

Lytic strains of *Escherichia coli* may also be used as hosts for the vectors of this invention. Suitable lytic strains include those which produce, at the temperature at which the polypeptide is produced but at a rate slower than that at which the polypeptide is produced, a substance e.g., an enzyme like endolysin which will cause the cell to lyse. This permits the cell to produce relatively large amounts of the desired polypeptide before the amount of the lysing substance produced reaches the level which causes cell lysis. Examples of suitable lytic strains include those containing the PlcI$^{ts}$ plasmid such as strain A4048 containing pHG44 which has been deposited with the ATCC under Accession No. 53217 as *Escherichia coli* strain A3111.

Preferably, the vector is a covalently closed circular double-stranded molecule. However, it is not essential that the vector be covalently closed.

The vector achieves its enhanced expression levels after the host cell is heated to a temperature at which the C$_I$ repressor protein is destroyed. A temperature above about 38° C. is effective for this purpose and since it is desired that unnecessary heat damage to the host cells be avoided to as great an extent as possible, it is generally desirable that the temperature not exceed 42° C. by more than a few degrees.

One important component of the vector is the ribosomal binding site. Suitable sites are C$_{II}$ from lambda bacteriophage having the sequence:

TAAGGAAATACTTACAT ATTCCTTTATGAATGTA;

a mutant of C$_{II}$ from lambda bacteriophage having the sequence:

TAAGGAAGTACTTACAT ATTCCTTCATGAATGTA;

the major head protein gene of bacteriophage lambda having the sequence:

TTTTTTACGGGATTTTTTTATG AAAAAAATGC-CCTAAAAAAATAC;

the natural β-lactamase ribosomal binding site derived from pBR322;

a synthetic oligonucleotide having the sequence:

AATTCGAGCGCAAGGAAACAGGCTCA GCTCGCGTTC-CTTTGTCCGAGTAT;

a synthetic oligonucleotide having the sequence:

AATTCAATAATATTGAAAAAGGAAGAG GTTAT-TATAACTTTTTCCTTCTCAT; and a natural ribosomal binding site derived from *Bacillus thurengensis*.

The vector also includes an origin of replication from a bacterial plasmid capable of autonomous replication in the host cell. Suitable such origins of replication may be obtained from a number of sources, e.g. from pBR322 or pR1.

A DNA sequence which contains a gene associated with a selectable or identifiable phenotypic trait which is manifested when the vector is present in the host cell is also a component of the vector. Suitable genes include those associated with temperature sensitivity or drug resistance, e.g., resistance to ampicillin, chloroamphenical or tetracycline.

Relative to vectors described previously, the vectors of this invention may be used to obtain enhanced expression of a wide variety of genes encoding desirable polypeptide products. Suitable genes include those encoding growth hormones, e.g., bovine, porcine, chicken or human growth hormones; superoxide dismutase; apoliprotein E or analogs of any of the preceding. By analog is meant a polypeptide having the same activity as the naturally occurring polypeptide but having one or more different amino acids added or deleted, or both, at the N-terminus of the polypeptide. However, some SOD analogs described have an amino acid sequence identical to that of mature human SOD.

The vector may be formed by methods well known to those of ordinary skill in the art to which the invention relates. Such methods are described in greater detail in various publications identified herein, the contents of which are hereby incorporated by reference into the present disclosure in order to provide complete information concerning the state of the art.

The vectors of this invention may be engineered to yield plasmids which produce a recombinant bovine growth hormone. One example is the production of an analog of bGH which has the amino acid sequence met-asp-gln added to the amino terminus of the phenylalanine form of authentic bGH. Plasmid pHG44, which produces such a hormone, was constructed according to the scheme in FIG. 6 and was deposited in strain A2097 under ATCC No. 39806.

Another plasmid which produces the met-asp-gln bovine growth hormone is p9200. The plasmid p9200 is similar to pHG44 (FIG. 6) however the plasmid confers tetracycline resistance instead of ampicillin resistance. The construction of p9200 is shown in FIG. 26. pHG44 was cleaved with ClaI and PstI, "filled in" using the Klenow fragment of DNA polymerase I and then the large DNA fragment was isolated. This fragment as ligated to a DNA fragment containing the tetracycline resistance gene of pBR322 which was isolated by cleaving pBR322 with RI and AvaI and then "filling in" using the Klenow fragment of DNA polymerase I. The resulting plasmid p9200 was deposited in the ATCC under Accession No. 53215.

Another example is the production of an analog of bGH having the amino acid methionine added to the amino terminus of the phenylalanine form of natural bGH. Plasmid pSAL 5600-1, which produces such a hormone, was constructed according to the scheme in FIG. 10. Plasmid p7200-22 also produces such a hormone. This plasmid has a restriction map shown in FIG. 7.

One presently preferred vector is p579 which has the restriction map shown in FIG. 19. This vector can be introduced into suitable *Escherichia coli* strain, e.g. A1637, A2602, A1563, A1645 or A2097, using a conventional transformation method known to those of ordinary skill in the art. A gene encoding a desired polypeptide, e.g. porcine growth hormone, chicken growth hormone or human growth hormone may be inserted into p579.

Porcine growth hormone CDNA has been inserted into p579 by digesting the vector with NdeI and ligating the open strand to pGH cDNA obtained from p3008 (ATCC No. 39804). The resulting plasmid is designated p3009. Its restriction map is shown in FIG. 11.

Porcine growth hormone cDNA has also been inserted into p579 by digesting the vector with NdeI and ligating the open strand to pGH cDNA obtained from p4005. The resulting plasmid is designated pAs 575. Its restriction map is shown in FIG. 50. p4005 may be obtained as described in copending co-assigned U.S. patent application Ser. No. 07/821,830, filed Jan. 23, 1986, now abandoned, which is incorporated herein by reference.

Chicken growth hormone CDNA has been inserted into p579 by digesting the vector with NdeI and ligating the open strand to cGH cDNA obtained from p5002. The resulting plasmid is designated p5003 and has a restriction map shown in FIG. 12. p5003 has been deposited in *Escherichia coli* strain A2097 under ATCC No. 39792.

The vectors of this invention may also be engineered to form plasmids capable of producing human growth hormone. An example of such a plasmid is pTV 300 which has the restriction map shown in FIG. 27. pTV 300 was constructed by cleaving pTV 18(1) with NdeI, isolating the met$^{14}$-hGH DNA and ligating it to p579 (FIG. 19) cleaved with NdeI. pTV 18(1) may be obtained as described in European Patent Application Publication No. 0 131 843 A1, published Jan. 23, 1985 or as described in corresponding U.S. patent application Ser. No. 06/514,188, filed Jul. 15, 1983, now abandoned, the latter of which is hereby incorporated by reference.

The gene for the production of human apopliprotein E (ApoE3), presumably with the amino acid methionine added to the amino terminus in the final product, can also be inserted into p579. The construction of the resulting plasmid, designated pTV-170, is shown in FIG. 20. This plasmid contains the $C_{II}$ ribosomal binding site derived from pJH200 (ATCC No. 39783).

Plasmid pTV-170 can be modified by removal of one of the NdeI sites bounding the ApoE gene. The resulting plasmid, designated pTV-190, is shown in FIG. 21.

pTV-170 can also be modified by replacement of the $C_{II}$ ribosomal binding site with the β-lactamase promoter and Shine-Dalagarno ribosomal binding site sequence isolated from pBLA11 (ATCC No. 39788). The resulting plasmid, designated pTV-194-80, has the restriction map shown in FIG. 22.

pTV-190 (FIG. 21) can be modified so that it produces an analog of human ApoE3 which has at its amino terminus the 14 amino acid amino terminus sequence of human growth hormone, followed by methionine, attached to.the sequence of mature human ApoE3. Such a plasmid is designated pTV-214 and has a restriction map shown in FIG. 24.

Another preferred embodiment of a plasmid which contains the ApoE3 gene is pTVR 279-8 which has the restriction map shown in FIG. 25. pTVR 279-8 was constructed from pTV 26465 which was constructed from pTV 190. Plasmid pTV 190, (FIG. 21), was partially cleaved with AvaI, "filled in" using the Klenow fragment of DNA polymerase I and religated. The resulting plasmid, designated pTV 264-45 is deleted of the AvaI site at the 3' end of the gene. Plasmid pTV 264-45 was digested to completion with NdeI and ligated to phosphorylated synthetic linkers of the sequence:

5'-TATGCTGCTGCT ACGACGACGAAT-5'

The resulting plasmid designated pTVR 279-8 has been deposited in the ATCC under Accession No. 53216.

pTV 194-80 (FIG. 22) can also be modified so that it produces an analog of human apolipoprotein E which has the amino acid sequence met-lys added to the N-terminus and alanine instead of lysine at position 143. Such a plasmid is designated pTHR 315-18 and has the restriction map shown in FIG. 33.

pTV 194-80 (FIG. 22) can also be modified so that it produces an analog of human apolipoprotein E in which the amino acids 73-255 inclusive are deleted. Such a plasmid is designated pTVR 298-34 and has the restriction map shown in FIG. 34.

pTVR 298-34 (FIG. 34) can be modified so that it produces an analog of human apolipoprotein E having the amino acid sequence met-lys added at the N-terminus and the amino acid serine instead of arginine at postion 136. Such a plasmid is designated pTHR 530-40 and has the restriction map shown in FIG. 35.

pTVR 298-34 (FIG. 34) can also be modified so that it produces an analog of apolipoprotein E having the amino acid sequence met-lys added to the N-terminus and the amino acid arginine rather than cysteine at position 112. Such a plasmid is designated pTHR 531-6II and has the restriction map shown in FIG. 36.

pTVR 298-34 can also be modified so that it produces an analog of human apolipoprotein E having the amino acid sequence met-lys added to the N-terminus and alanine rather than histidine at position 140. Such a plasmid is designated pTHR 532-18 and has the restriction map shown in FIG. 37.

pTVR 298-34 (FIG. 34) can also be modified to produce an analog of human apolipoprotein E having the amino acid sequence met-lys added to the N-terminus and an alanine rather than an arginine at position 150. Such a plasmid is designated pTHR 533-4 and has the restriction map shown in FIG. 38.

pTVR 264-45 (FIG. 25) can be modified so that it produces an analog of human apolipoprotein E having the amino acid sequence met-leu-leu-leu added to the N-terminus and a proline rather than a leucine at position 140. Such a plasmid is designated pTHR 299-40 and has the restriction map shown in FIG. 39.

pTVR 298-34 (FIG. 34) can be modified to produce an analog of human apolipoprotein E having the amino acid sequence met-lys added to the N-terminus and a proline rather than a leucine at position 144. Such a plasmid is designated pTHR 526-6 and has the restriction map shown in FIG. 40.

pTVR 264-45 (FIG. 25) can also be modified so that it produces an analog of apolipoprotein E which has the amino acid sequence met-lys added to the N-terminus and wherein amino acids 118–119 are histidine-methionine instead of tyrosine-arginine. Such a plasmid is designated pTHR 324-20 and has the restriction map shown in FIG. 41.

pTHR 324-20 (FIG. 41) can be modified so that it produces an analog of human apolipoprotein E wherein the first 119 amino acids are deleted. Such a plasmid is designated pTHR 501 and has the restriction map shown in FIG. 42.

pTHR 324-20 (FIG. 41) may also be modified so that it produces an analog of human apolipoprotein E having the amino acid sequence met-leu-leu-leu added to the N-terminus and wherein the first 119 amino acids of the protein are deleted. Such a plasmid is designated pTHR 514-7 and has the restriction map shown in FIG. 43.

pTHR 324-20 (FIG. 41) may be modified to form another plasmid which produces an analog of natural apolipoprotein E wherein the first 119 amino acids are deleted. The plasmid is designated pTHR 520-3 and has the restriction map shown in FIG. 44.

pTVR 264-45 (FIG. 25) may also be modified so that it produces an analog of natural apolipoprotein E having the amino acid sequence met-lys added to the N-terminus wherein there is an arginine rather than serine at position 139 and alanine rather than leucine at position 149. Such a plasmid is designated pTHR 325-22 and has the restriction map shown in FIG. 45.

pTVR 279-8 (FIG. 25) may be modified so that it produces an analog of natural apolipoprotein E having the amino acid sequence met-leu-leu-leu added to the N-terminus. Such a plasmid is designated pTVR 289-18 and has the restriction map shown in FIG. 46.

pTVR 289-18 (FIG. 46) may be modified so that it produces an analog of human apolipoprotein E having the amino acid sequence met-leu-leu-leu added to the N-terminus and arginine instead of serine at position 139 and an alanine instead of a leucine at position 149. Such a plasmid is designated pTHR 525-2 and has the restriction map shown in FIG. 47.

pTVR 289-18 (FIG. 46) may also be modified so that it produces an analog of human apolipoprotein E having the amino acid sequence met-leu-leu-leu added to the N-terminus and an arginine rather than a cysteine at position 112. Such a plasmid is designated pTHR 540-37 and has the restriction map shown in FIG. 48.

pTVR 289-18 (FIG. 46) can also be modified so that it produces an analog of human apolipoprotein E having the amino acid sequence met-leu-leu-leu added to the N-terminus and an alanine rather than a histidine at position 140. Such a plasmid is designated pTHR 539-5II and has the restriction map shown in FIG. 49.

The vectors of this invention may also be engineered to yield plasmids which produce an analog of human Cu-Zn superoxide dismutase (SOD) which differs from natural human SOD in that the amino terminus is not acetylated. Such a plasmid has been constructed according to FIG. 16 and has been designated pSOD$\beta_1$TT-1.

Using the same approach other plasmids may be prepared by inserting into the second restriction enzyme site of a vector according to the invention a gene encoding a desired polypeptide.

The preceding specific host vector systems involve E. coli A1637, A1645, A2606, A2097 and A1563, A4200, A4255, A4346 and A4048. These host vector systems may be used to produce different polypeptides such as bovine, porcine, chicken and human growth hormones, superoxide dismutase and human apolipoprotein E. To do so, the host vector system is grown under suitable conditions permitting production of polypeptide which is then recovered.

Suitable conditions involve growth of the host vector system for an appropriate period of time at about 42° C. Desirably, the period of growth at 42° C. for all host vector systems except those designed to produce human apolipoprotein E is about 1 to 5 hours. The period of growth for host vector systems designed to produce human apolipoprotein E is desirably about 15 minutes.

By means of the preceding method, a number of bGH, pGH, cGH, hGH, ApoE and SOD analogs have been prepared.

A pGH analog has been prepared in which the amino acid methionine is added to the N-terminus of natural porcine growth hormone.

A hGH analog has been prepared which is deleted of the first 13 amino acids of natural human growth hormone, i.e., met$^{14}$ hGH.

Analogs of hApoE which have been prepared include the following:

(1) An analog of human apolipoprotein E having the amino acid sequence of human apolipoprotein E to the N-terminus of which the methionine followed by the 13 amino acid N-terminal sequence of human growth hormone is attached, followed by methionine;

(2) natural human apolipoprotein E having the amino acid sequence met-leu-leu-leu-met attached to the N-terminus;

(3) an analog of human apolipoprotein E having the amino acid sequence met-lys added to the N-terminus and alanine instead of lysine at position 143;

(4) an analog of human apolipoprotein E having the amino acid sequence met-lys added to the N-terminus and wherein amino acids 73-255 inclusive are deleted;

(5) an analog of human apolipoprotein E having the amino acid sequence met-lys added to the N-terminus and serine instead of arginine at position 136;

(6) an analog of apolipoprotein E having the amino acid sequence met-lys added to the N-terminus and arginine instead of cysteine at position 112;

(7) an analog of human apolipoprotein E having the amino acid sequence met-lys added to the N-terminus and alanine instead of histidine at position 140;

(8) an analog of human apolipoprotein E having the amino acid sequence met-lys added to the N-terminus and alanine instead of arginine at position 150;

(9) an analog of human apolipoprotein E having the amino acid sequence met-leu-leu-leu added to the N-terminus and proline instead of leucine at position 144;

(10) an analog of human apolipoprotein E having the amino acid sequence met-lys added to the N-terminus and proline instead of leucine at position 144;

(11) an analog of human apolipoprotein E having the amino acid sequence met-lys added to the N-terminus and histidine-methionine instead of tyrosine-arginine at positions 118–119;

(12) an analog of human apolipoprotein E wherein the first 119 amino acids are deleted;

(13) an analog of human apolipoprotein E having the amino acid sequence met-leu-leu-leu added to the N-terminus and wherein the first 119 amino acids are deleted;

(14) an analog of human apolipoprotein E having the amino acid sequence met-lys added to the N-terminus and arginine instead of serine at position 139 and alanine instead of leucine at position 149;

(15) an analog of human apolipoprotein E having the amino acid sequence met-leu-leu-leu added to the N-terminus and arginine instead of serine at position 139 and alanine instead of leucine at position 149;

(16) an analog of human apolipoprotein E having the amino acid sequence met-leu-leu-leu added to the N-terminus and arginine instead of cysteine at position 112;

(17) an analog of human apolipoprotein E having the amino acid sequence met-leu-leu-leu added to the N-terminus and alanine instead of histidine at position 140.

Veterinary compositions may be prepared which contain effective amounts of one or more bGH, cGH or pGH analog and a suitable carrier. Such carriers are well known to those of ordinary skill in the art. The analogs may be administered directly or in the form of a composition to a cow in order to increase milk or meat production, to a chicken in order to increase meat production or to a pig in order to increase milk or meat production.

Pharmaceutical compositions may be prepared which contain effective amounts of one or more SOD or ApoE analogs and a suitable carrier. Such carriers are well known to those skilled in the art. The analogs may be administered directly or in the form of a composition to a human subject, e.g., to treat deficiencies in SOD or ApoE production by the subject, or in the case of SOD to treat inflammation or other disorders for which human superoxide dismutase is indicated or in the case of ApoE to treat arterioscelerosis.

EXAMPLES

The examples which follow are set forth to aid in understanding the invention but are not intended to, and should not be construed to, limit its scope in any way. The examples do not include detailed descriptions for conventional methods employed in the construction of vectors, the insertion of genes encoding polypeptides of interest into such vectors or the introduction of the resulting plasmids into bacterial hosts. Such methods are well-known to those of ordinary skill in the art and are described in numerous publications including by way of example the following:

T. Maniatis, E.F. Fritsch and J. Sambrook, *Molecular Cloning; A Laboratory Manual*, Cold Spring Harbor Laboratory, New York (1982).

*Methods in Enzymology*, vol. 65, "Nucleic Acids (Part 1)," edited by Lawrence Grossman and Kivie Moldave, Academic Press, New York (1980).

*Methods in Enzymology*, vol. 68, "Recombinant DNA," edited by Ray Wu, Academic Press, New York (1981).

*Methods in Enzymology*, vol. 100, "Recombinant DNA (Part B)," edited by Ray Wu, Lawrence Grossman and Kivie Moldave, Academic Press, New York (1983).

*Methods in Enzymology*, vol. 101, "Recombinant DNA (Part C)," edited by Ray Wu, Lawrence Grossman and Kivie Moldave, Academic Press, New York (1983).

*Principles of Gene Manipulation, An Introduction to Genetic Engineering*, 2nd Edition, edited by R.W. Old and S.B. Primrose, University of California Press (1981).

H.V. Bernard, et al., Gene (1979) 5, 59.

A.B. Oppenheim, et al., J. Mol. Biol. (1982) 158, 327.

E. Remaut, et al., Gene (1981) 15, 81.

EXAMPLE 1

Expression Vectors

I. p579

The vector p579, shown in FIG. 19 and described in detail under Description of the Figures, is composed of a $\lambda P_L$ promoter, and N utilization site (NutL), the $C_{II}$ ribosomal binding site bounded by unique EcoRI and NdeI restriction sites, an ATG initiation codon and the $T_1T_2$ transcription termination signals derived from the end of the rrnB ribosomal RNA gene operon of *Escherichia coli*. These elements are cloned on pBR322 carrying the ampicillin resistance gene. Other features are shown in FIG. 19.

p579 was prepared by inserting the $T_1T_2$ transcription termination signals contained on the plasmid pPS1 into the HindIII site of the vector pRO211. pRO211 is shown in FIG. 2. pPS1 has been described in Sarmientos, et al., Cell (1983) 32, 1337–1346 and has been deposited with the American Type Culture Collection under ATCC Number 39807. p579 and its derivatives containing eucaryotic genes may be maintained in suitable *Escherichia coli* hosts. The most important feature of the host is that it provides the thermosensitive repressor cI857 and the antitermination N protein. (Gottesman, M. et al., J. Mol. Biol. (1980) 140, 57–75).

p579 has numerous advantages over previously described expression vectors including:

1. extremely high levels of expressions

This vector is capable of directing expression of foreign proteins in *E. coli* at levels as high as 42% of the total cellular protein. This level of expression is higher than that described for other similar $\lambda P_L$ plasmids lacking the $T_1T_2$ transcription termination sequences.

2. transcription termination signals

The vector p579 contains the $T_1T_2$ transcription termination signals placed "downstream" from the $\lambda P_L$ promoter and $C_{II}$ ribosomal binding site. The high levels of expression which are obtained when using this vector are due in part to the presence of the $T_1T_2$ transcription terminators at the end of the inserted gene, as the $T_1T_2$ transcription terminators are capable of terminating transcription of N modified RNA polymerase. Thus the transcription terminators prevent the $\lambda P_L$ controlled transcription of undesired plasmid proteins, thereby enhancing the relative yields of the desired protein.

3. replaceable ribosomal binding sites p579 contains a unique EcoRI site which is located "upstream" of the ribosomal binding site, and a unique NdeI site located at the ATG initiation codon. Thus, the ribosomal binding site is bounded by two unique restriction sites. This enables facile excision of the present ribosomal binding site (the $\lambda C_{II}$ ribosomal binding site) and substitution of virtually any other natural or synthetic ribosomal binding site without altering other features of the plasmid. This greatly facilitates optimal expression of desired polypeptides.

4. thermoinducible regulation of expression

The $\lambda P_L$ promoter is inactive when the $C_I$ repressor is bound to it. The cI857 repressor is thermosensitive, that is, it binds to the promoter at 30° C. but is inactivated at 42° C. Thus, by increasing the temperature of fermentation to 42° C. the host bacteria are induced to produce the desired protein.

The advantages of such a system include the following:
  (a) a foreign protein which is toxic to *Escherichia coli* can be produced late in the fermentation process thus avoiding early cell death.
  (b) overproduction of a protein may stabilize the protein and prevent proteolytic degradation (Cheng, Y.E., et al., Gene (1981) 14, 121). Thus, "instantaneous" overproduction using a tightly regulated promoter such as $\Delta P_L$ may be preferable to continuous low level production.

5. simplified induction protocol

The plasmids derived from p579 are induced at about 42° C. and maintained at 42° C. throughout the period of protein synthesis. The induction protocol for plasmids derived from pMG100 and pND5 described in copending, coassigned U.S. patent application Ser. No. 514,188 requires a temperature shift to 42° C. followed by an extended period of growth at 38° C. The optimal induction protocol for p579 does not require the cooling step to 38° C. and is thus simplified.

6. high copy number

The $\lambda P_L$ promoter in p579 is found on a plasmid with a copy number higher than that of $\lambda$ transducing phage vectors which are used in *Escherichia coli*. This increases expression levels.

7. ribosome binding site and initiation codon

This expression vector contains a strong procaryotic ribosomal binding site (RBS) as well as a translation initiation codon (ATG). Thus, any eucaryotic gene may be cloned without adding an initiation codon. Furthermore, the efficient RBS increases levels of expression. The ribosome binding site is the $XC_{II}$ ribosomal binding site which we previously cloned into the vector pND5. The sequence of the ribosomal binding site is

TAAGGAAGTACTTACAT ATTCCTTCATGAATGTA.

One base pair is different from the ribosomal binding site found in wild type $\lambda$.

8. convenient restriction site

The expression vector has a unique NdeI restriction site which contains within it, the ATG initiation codon. This permits proper positioning of the desired gene. The unique NdeI site is found immediately after the ribosomal binding site.

9. convenient restriction sites for gene insertion

Located 116 base pairs downstream of the NdeI restriction site are unique restriction sites BglII and SmaI, in that order. These unique restriction sites enable facile insertion of desired genes.

10. nut site

N protein, which is provided by the host, binds to the Nut site on the expression vector and thereby prevents termination of transcription at the $t_{RI}$ site or premature transcription termination within the cloned gene.

Strains

Suitable hosts for the described vectors and plasmids are strains of *Escherichia coli* suitable for transformation, including A1637, A2602, A1563, A1645 (c600 r⁻m⁺ gal⁺ thr⁻ leu⁻ lac⁻b1 ($\lambda$cI857 $\Delta$H1 $\Delta$BamHI N⁺) and A2097 (A1645 lac $\Delta$XA21 proC::Tn 10).

EXAMPLE 2

Animal Growth Hormones

I. pHG44

The construction of pHG44 is shown in FIG. 6, described in the Description of the Figures and deposited under ATCC No. 39806. The plasmid was derived from the pRO12 plasmid shown in FIG. 2 by insertion of the $T_1T_2$ transcription termination sequences from the plasmid pPS1 which is shown in FIG. 6, described in Sarmientos, et al., Cell (1983) 32, 337-1346 and deposited under ATCC No. 39807. The presence of the $T_1T_2$ termination sequences prevents long run-on mRNA transcripts, and thus prevents high-level expression of the $\beta$-lactamase gene and possibly other undesired proteins under the control of the $\lambda P_L$ promoter.

The plasmid pHG44 has been introduced into *Escherichia coli* strain A2097 by transformation using methods known to those of ordinary skill in the art. This strain produced upon growth and induction an analog of bovine growth hormone (bGH) having the amino acid sequence met-asp-gln added to the amino-terminus of the phenylalanine form of the authentic bGH. The amount of bGH analog produced by pHG44 was about 37–42% of the total protein produced by the bacteria as calculated by scanning Coomasie-stained SDS polyacrylamide gels.

The methods used to grow the strain, recover the bGH analog produced and purify the bGH analog, are described in Example 5. The level of expression is higher than that obtained from pRO12 (Table I) due to a significant reduction in $\beta$-lactamase expression effected by the introduction of the $T_1T_2$ termination sequences at the 3' terminus of the bGH gene.

II. pSAL 5600-1

The construction of pSAL 5600-1 is shown in FIG. 10 and described in the Description of the Figures. The plasmid pSAL 5600-1 was derived from pSAL 5200-6 (shown in FIG. 3) by insertion of the $T_1T_2$ termination sequences from the plasmid pPS1 (ATCC No. 39807).

The plasmid pSAL 5600-1 was introduced into *Escherichia coli* strain A1645 by transformation using methods known to those of ordinary skill in the art. This strain produced upon growth and induction an analog of bGH having the amino acid methionine added to the amino-terminus of the phenylalanine form of natural bGH. The amount of bGH analog produced by pSAL 5600-1 strains was about 22–28% of the total protein produced by the bacteria as calculated by scanning Coomasie-stained SDS polyacrylamide gels. The methods used to grow the strain, recover the bGH analog produced and purify the bGH analog, are the same as those described for pHG44 in Example 5.

The level of expression was higher than that obtained from pSAL 5200-6 strains due to a significant reduction in β-lactamase expression effected by the introduction of the $T_1T_2$ termination sequences at the 3' terminus of the bGH gene.

III. p3009

The construction of p3009 is shown in FIG. 11 and described in the Description of the Figures. The plasmid p3009 was obtained by insertion of the NdeI-NdeI porcine growth hormone cDNA fragment into the unique NdeI site of the p579 expression vector (FIG. 19). The porcine growth hormone (pGH) fragment was isolated from p3008 (ATCC No.39804) by an NdeI digestion.

The plasmid p3009 was introduced into *Escherichia coli* strain A1645 by transformation using methods known to those of ordinary skill in the art. This strain produced upon growth and induction an analog of pGH having the amino acid methionine added to the amino-terminus of the phenylalanine form of the natural pGH. The amount of pGH analog produced was about 30–35% of the total protein produced by the bacteria as calculated by scanning Coomasie-stained SDS polyacrylamide gels. The methods used to grow the strain, recover the pGH analog produced and purify the pGH analog, are the same as those described for pHG44 in Example 5.

The level of expression of p3009 was higher than that obtained from p3008 strains due to a significant reduction in β-lactamase expression effected by the introduction of the $T_1T_2$ termination sequences at the 3' terminus of the pGH gene.

IV. p5003

The construction of p5003 is shown in FIG. 12 and described in the Description of the Figures. p5003 has been deposited with the American Type Culture Collection under ATCC No. 39792. The plasmid was obtained by insertion of the NdeI-NdeI chicken growth hormone cDNA fragment from p5002 into the unique NdeI site of the p579 expression vector.

The plasmid p5003 was introduced into *Escherichia coli* strain A2097 by transformation using methods known to those of ordinary skill in the art. This strain produced upon growth and induction an analog of chicken growth hormone (cGH) having the amino acid methionine added to the aminoterminus of the phenylalanine form of the natural cGH. The amount of cGH analog produced was about 30–35% of the total protein produced by the bacteria as calculated by scanning Coomasie-stained SDS polyacrylamide gels. The methods used to grow the strain recover the cGH analog produced and purify the cGH analog, are the same as those described for pHG44 in Example 5.

The level of expression of p5003 was higher than that obtained from p5002 strains due to a significant reduction in β-lactamase expression effected by the introduction of the $T_1T_2$ termination sequences at the 3' terminus of the cGH gene.

TABLE I[1]

| Plasmid | % bGH[2] | Remarks |
|---|---|---|
| pRec 2/3 | 23 | Amp[R] |
| pRO11 | 28 | Amp[R] |
| pRO12 | 30–36 | Amp[R] |
| pHG44 | 37–42 | Amp[R], $T_1T_2$ |
| pHG50 | 37–42 | Amp[R], $T_1T_2$; cI[434] |
| pSAL-130/5 | 39–44 | Amp[R]; CHCN; $T_1T_2$ |
| pSAL-170/10 | 40–46 | Tet[R]; CHCN; $T_1T_2$ |

[1] The table summarizes the bGH expression levels of various plasmids derived from pRO211, and also of plasmids pRec 2/3 and pRO11 both of which are described in coassigned U.S. Pat. No. 4,831,120, issued May 16, 1989, continuation of U.S. application Ser. No. 514,188, filed July 15, 1983.
[2] Amount of bGH produced as percentage of total bacterial protein.

ABBREVIATIONS
CHCN = Constitutive high copy number
Amp[R] = Ampicillin resistance
Tet[R] = Tetracycline resistance
$T_1T_2$ = Transcription termination sequences
cI[434] = Plasmid stabilization cI[434] system

EXAMPLE 3

Human Cu-Zn Superoxide Dismutase (SOD)

I. pSODβ$_1$TT-1

The construction of pSODβ$_1$TT-1 is shown in FIG. 16 and described in the Description of the Figures. The plasmid pSODβ$_1$TT-1 was obtained by insertion of the $T_1T_2$ termination sequences at the 3' end of the SOD gene found in pSODβ$_1$T$_{11}$ (FIG. 15).

The plasmid pSODβ$_1$TT-1 was introduced into *Escherichia coli* strain A1645 by transformation using methods known to those of ordinary skill in the art. This strain produced upon growth an SOD analog. The amount of SOD analog produced was about 10–15% of the total protein produced by the bacteria as calculated by scanning Coomasie-stained SDS polyacrylamide gels.

The methods used to grow the strain, recover the SOD analog produced and purify the SOD analog, are described in Example 7.

The level of expression of pSODβ$_1$TT-1 was higher than that obtained from pSODβ$_1$T$_{11}$ (Table II) due to the $T_1T_2$-induced reduction in transcription and translation of non-desired DNA sequences.

The human Cu-Zn SOD analog produced differs from natural human Cu-Zn SOD in that the amino terminus alanine. is not acetylated, as demonstrated by amino acid sequencing stoichiometry. The natural human SOD is acetylated at the amino terminus alanine (Hartz, J.W. and Deutsch, H.F., J. Biol. Chem. (1972) 247, 7043–7050, Jabusch, J.R., et al., Biochemistry (1980) 19, 2316–2316; Barra, et al., FEBS Letters (1980) 120, 53 and Oberley, L.W., Superoxide Dismutase, Vol. I, CRC Press, Florida, (1982), pp. 32–33). The natural human SOD is glycosylated (Huber, W., U.S. Pat. No. 3,579,495, issued May 18, 1971). Bacterial-produced human SOD is almost certainly not glycosylated as *Escherichia coli* does not glycosylate proteins which it produces. The amino acid sequence of the bacterial-produced SOD analog is identical to that of mature human SOD and does not contain a methionine residue at its N-terminus.

TABLE II

| Plasmid | RBS | % SOD[3] | Remarks |
|---|---|---|---|
| pSODα2 | C_II | 0.1–0.3 | Amp^R |
| pSODβ_1 | BLA[1] | 3–8 | Amp^R |
| pSODβ_1T_11 | BLA[1] | 8–13 | Tet^R |
| pSODβ_1TT-1 | BLA[1] | 10–15 | Tet^R; T_1T_2 |
| pSODβ_1-BA2 | BLA[2] | 2–4 | Amp^R |

[1] Promoter and ribomosal binding site of β-lactamase gene.
[2] Synthetic ribosomal binding site corresponding to that of the β-lactamase gene.
[3] Amount of SOD analog produced expressed as percentage of total bacterial protein.

ABBREVIATIONS
Amp^R = Ampicillin resistance
Tet^R = Tetracycline resistance
T_1T_2 = Transcription termination sequences

EXAMPLE 4

Human Apolipoprotein E3 (Apo-E3)

I. pTV-170

The construction of pTV-170 is shown in FIG. 20 and described in the Description of the Figures. The plasmid pTV-170 was obtained by insertion of the NdeI-NdeI Apo-E3 fragment derived from pApoE-EX2 (ATCC No.39787) into the unique NdeI site of the expression vector p579.

pTV-170 was introduced into *Escherichia coli* strain A1645 by transformation using methods known to those of ordinary skill in the art. The clone obtained produced upon growth human ApoE3, presumably having the amino acid methionine added to the amino-terminus of natural human ApoE3. The amount of human ApoE3 analog produced was about 1% of the total protein produced by the bacteria as calculated by scanning of Coomasie-stained SDS polyacrylamide gels. The methods used to grow the strain are described in Example 7.

II. pTV-194-80

The construction of pTV-194-80 is shown in FIG. 22 and is described in the Description of the Figures. pTV-194-80 was derived from pTV-170 (FIG. 20) by replacing the C_II ribosomal binding site with the β-lactamase promoter and ribosomal binding site derived from pBLA11. pBLA11 contains the promoter and ribosomal binding site of the β-lactamase gene found in pBR322 between coordinates 4157 and 4353. An EcoRI linker was added upstream of the promoter and a multi-restriction site linker was added immediately after the initiation codon ATG. Thus the sequence of the coding strand beginning with the initiation codon is ATGAGCTCTAGAATTC. pBLA11 was deposited in the American Type Collection Center as ATCC No. 39788.

pTV-194-80 was introduced into *Escherichia coli* strain A1645 by transformation using methods known to those of ordinary skill in the art. The clone obtained produced upon growth an analog of human ApoE3, presumably having the amino acid methionine added to the amino-terminus of natural human ApoE3. The amount of human Apo-E analog produced was about 3% of the total protein produced by the bacteria as calculated by scanning Coomasie-stained SDS polyacrylamide gels. The methods used to grow the strain are the same as described for pTV-170 in Example 7.

III. pTV-214

The construction of pTV-214 is shown in FIG. 24 and is described in the Description of the Figures. pTV-214 was derived from pTV-190 (shown in FIG. 21 and described in the Description of the Figures) by insertion of a synthetic DNA fragment coding for the 14 amino acid amino-terminal sequence of human growth hormone into the unique NdeI site of pTV-190.

pTV-214 was introduced into *Escherichia coli* strain A1645 by transformation using methods known to those of ordinary skill in the art. The clone obtained produced upon growth and induction an analog of human ApoE3 having at its amino terminus methionine followed by the 13 amino acid amino-terminal sequence of human growth hormone, followed by methionine attached to the sequence of mature human ApoE3. The amount of human ApoE analog produced was about 2% of the total protein produced by the bacteria as calculated by scanning Coomasie-stained SDS polyacrylamide gels. The methods used to grow the strain are the same as those described for pTV-170 in Example 7.

EXAMPLE 5

Growth of pHG44

I. Stock Cultures

Stock cultures of pHG44 were grown on casein medium (see Inoculum), then diluted two-fold with freezing medium and stored at −80° C. Freezing medium contains per 500 ml:

| | |
|---|---|
| K_2HPO_4 | 6.3 g |
| KH_2PO_4 | 1.8 g |
| Na Citrate | 0.45 g |
| MgSO_4 · 7H_2O | 0.09 g |
| (NH_4)_2SO_4 | 0.9 g |
| Glycerol | 44.0 g |

II. Inoculum

The inoculum was propagated in 20 g/l casein hydrolysate, 10 g/l yeast extract and 2 g/l NaCl. Sterile medium in a shake flask was inoculated from stock culture and incubated 15 hours on a shaker at 30° C. and approximately 200 r.p.m. As needed, subsequent stages in inoculum propagation were carried out in stirred aerated fermenters. Sterile medium was inoculated with 2–10% inoculum culture and incubated 15 hours at 30° C., pH 7±0.5 with agitation and aeration to maintain a dissolved oxygen level above 20% air saturation.

III. Production

The production medium contains:

| | |
|---|---|
| Casein hydrolysate | 20 g/l |
| Yeast extract | 10 g/l |
| K_2HPO_4 | 2.5 g/l |
| MgSO_4 · 7H_2O | 1 g/l |
| NaCl | 5 g/l |
| Biotin | 0.1 mg/l |
| Thiamine | 1 mg/l |
| Trace elements solution | 3 ml/l |

The medium also contains 100 mg/liter ampicillin. The ampicillin is optional for production but is always found in the medium used for growing the inoculum.

Biotin, thiamine, and ampicillin in concentrated solutions were filter sterilized separately and added to the sterile production medium before inoculation. Sterile glucose solution was added initially to supply 10 g/l. At the induction step another 10 g/l of glucose was added.

The trace elements solution contains:

| | |
|---|---|
| FeCl$_3$ | 16 g/l |
| ZnCl$_2$ · 4H$_2$O | 2 g/l |
| CoCl$_2$ · 6H$_2$O | 2 g/l |
| Na$_2$MoO$_4$ · 2H$_2$O | 2 g/l |
| CaCl$_2$ · 2H$_2$O | 1 g/l |
| CuCl$_2$ | 1 g/l |
| H$_3$BO$_3$ | 0.5 g/l |
| Conc. HCl | 100 ml/l |

The medium is inoculated with 0.5–10% inoculum culture and incubated at 30° C. Agitation-aeration rates are set to maintain dissolved oxygen level above 20% air saturation. The pH is maintained at 7±0.2 with NH$_3$. Once cell concentration reaches about 3.5 g/l (OD$_{660}$=10) induction is started.

The temperature is raised to 42° C. and maintained at 42° C. for 1–5 hours. The culture is then chilled and cells are recovered by centrifugation for hormone purification.

Recovery of bGH

Thirteen kilograms of bacterial cells (wet cake) are resuspended in 5 volumes of a solution containing 50 mM sodium phosphate buffer (pH 7.4), 50 mM EDTA and 100 mM NaCl, using a Polytron (Kinematica) blender, while controlling the blender's speed to minimize foaming. The homogeneous suspension is continuously passed through a Dynomill cell disruptor KD5 (Willy A. Bachofen, Basel) at a rate of 80 liter per hour and the homogeneous suspension of disrupted cells clarified by centrifugation in a CEPA 101 centrifuge at a flow rate of 45 liter per hour. The precipitate from the centrifugation step was collected and resuspended in 15.5 liters of 50 mM sodium phosphate buffer (pH 7.4) containing 50 mM EDTA. Lysozyme is added to a final concentration of 0.05 mg/ml and the suspension incubated for 16 hours at 37° C. Triton X-100 is added to a final concentration of 1%. The suspension is then incubated for 30 min at room temperature, sonicated in a continuous flow cell sonificator (Heat System) at a rate of 18 liters per hour and centrifuged in a CEPA 101 centrifuge. The precipitate is collected, resuspended in 50 mM sodium phosphate buffer (pH 7.4), sonicated as above, and centrifuged in a CEPA 101 centrifuge. The cells are resuspended in 15.5 liters of 50 mM sodium phosphate buffer (pH 7.4) containing 50 mM EDTA and 100 mM NaCl and twice precipitated and resuspended in 15.5 liters of distilled water. The precipitate is collected by centrifugation and stored at −20° C.

Purification of bGH

The precipitate is resuspended in 30–40 liters distilled water and solubilized by titration with 0.5 N NaOH to pH 11.8. The solution is then continuously sonicated and clarified by centrifugation in CEPA 101 centrifuge if necessary, or filtered through Whatman No. 1 paper.

The clarified protein solution (32.6 liters containing 297,000 OD's at 280 nm) is divided into separate portions (6×5.4 liters) each containing 50,000–60,000 OD's. Each portion is ultrafiltered separately through a Millipore Pellicon ultrafilter equipped with three 100,000 molecular weight cutoff cassettes (type PTHK) of 5 ft$^2$ area each. A 5.4 liter portion is concentrated to 1 liter retentate volume. The ultrafiltrate is collected and saved. The retentate is diluted back to its original volume with fresh 10 mM Borate buffer pH 11.8, and mixed well. The batch is concentrated again to 1 liter retentate volume. The ultrafiltrate is collected and combined with the first ultrafiltrate. When the running total of the OD's in the ultrafiltrates equals 20% of the OD's initially charged to the ultrafilter, the retentate volume on the next concentration step is taken to 0.5 liters instead of 1 liter. The cycle of concentration and dilution with 10 mM Borate buffer is continued until the ultrafiltrate from a retentate volume of 0.5 liters has an absorbance at 280 nm (1-cm cell) of less than 0.1. This normally takes between 9 and 12 cycles of concentration and dilution. The final retentate is discarded.

All ultrafiltrates are combined and adjusted to pH 9.0 with 6N HCl. The other 5.4-liter portions are ultrafiltered in the same fashion, and all pH adjusted ultrafiltrates are combined. A typical run produces a total of 380 liters of ultrafiltrates with an absorbance of 0.26 equivalent to 100,000 OD's and requires 24 to 40 hours to complete.

The combined ultrafiltrates (380 liters containing 100,000 OD's at 280 nm) from the 100K ultrafiltration step are loaded onto a Sepharose CL-6B DEAE ion-exchange column at a linear flow velocity of 23 cm/hr (25 liter/hr). The 37-cm diameter 15-cm high column is washed with two bed volumes (32 L) of 10 mM Borate buffer at pH 9.0. The eluate from the loading and washing steps is discarded. A step change in eluent to 10 mM Borate, 100 mM sodium chloride, pH 9, displaces the bGH off the column. The elution flow velocity is 23 cm/hr. The progress of the run is monitored by following absorbance of the eluate at 280 nm. The bGH peak is collected in 4 to 5 bed volumes (84 liters containing 43,000 OD's at 280 nm) and then concentrated to approximately 10 mg/ml using a Millipore Pellicon ultrafiltration device with a 10,000 molecular weight cutoff cassette. The solution is then lyophilized. The yield is approximately 70 g of pure bGH.

EXAMPLE 6

Activity of bGH Analog Produced by pHG44

1. Radioimmunoassay Comparison of bGH Analog with Natural bGH

A solution containing 100 ng/ml bGH analog was prepared in phosphate buffered saline (including 1% BSA). This solution was diluted serially to concentrations of 50, 25, 12.5, 6.25, 3.12, 1.56 and 0.78 ng/l. Duplicate 0.1 ml aliquots of these solutions were submitted to RIA using a double antibody procedure. The dilution curve was comparable to that obtained with natural bGH.

2. Radioreceptor Binding Assay

A radioreceptor binding assay was performed with rabbit liver membranes as described by Tushima, T. and Freisen, H. G., (Y. Chin., Endocr. Metab. (1973), 37, 3) using $^{125}$I-bGH as the tracer and authentic bGH solutions for the construction of calibration curves. Samples were incubated in triplicate for two hours at room temperature in 0.3 ml of assay buffer (50 mM Tris, 15 mM CaCl$_2$ and 5 mg/ml bovine serum albumin, pH 7.6). The tubes contained $^{125}$I-bGH (20,000 cpm of preparation of 30–60 μci/μg), 150–250 μg liver membrane protein and either natural bGH (1–100 ng) or extracts of bacterial bGH. The result demonstrates that the bGH activity of the bGH analog is comparable to that of natural bGH.

3. Tibia Test

The bioactivity of the pRO12 produced bGH analog recovered from bacterial cells according to Example 5 was evaluated by a tibia test. (Parlow, A. F., et al., Endocrinology (1965) 77, 1126). Rats were hypophysectomized at 28–30 days of age, then kept for 10–14 days without treatment. Bovine growth hormone derived from bone pituitaries or from recombinant *Escherichia coli* was dissolved in 0.15M NaCl with 0.01M borate, pH 10.0. Rats (4–7 per group) received daily subcutaneous injections of bGH solutions (5–125μg/day in 0.2 cc) for 5 days while kept on a normal diet (Purina Rat-Chow and water adlibitum). The animals were sacrificed on the 6th day, their foreleg knee-bones taken out, cut longitudinally, fixed with acetone and stained with 2% AgNO$_3$. The width of the epiphyseal plates was measured by observation through a dissecting binocular (Nikon). Mean values (40 readings per rat) were used for the constructon of long dose-response curves. The results demonstrated that the bGH activity of the pHG44-produced bGH analog is comparable to that of natural bGH.

EXAMPLE 7

Growth of pSODβ$_1$TT-1

1. Stock Cultures

Stock cultures of pSODβ$_1$TT-1 were grown on casein medium (see Inoculum), then diluted two-fold with freezing medium and stored at −80° C. Freezing medium contains per 500 ml:

|  |  |
|---|---|
| K$_2$HPO$_4$ | 6.3 g |
| KH$_2$PO$_4$ | 1.8 g |
| Na Citrate | 0.45 g |
| MgSO$_4$ · 7H$_2$O | 0.09 g |
| (NH$_4$)$_2$SO$_4$ | 0.9 g |
| Glycerol | 44.0 g |

II. Inoculum

The inoculum was propagated in 20 g/l casein hydrolysate, 10 g/l yeast extract and 2 g/l NaCl. Sterile medium in a shake flask was inoculated from stock culture and incubated 15 hours on a shaker at 30° C. and approximately 200 r.p.m. As needed, subsequent stages in inoculum propagation were carried out in stirred aerated fermenters. Sterile medium was inoculated with 2–10% inoculum and incubated 15 hours at 30° C., pH 7±0.5 with agitation and aeration to maintain a dissolved oxygen level above 20% air saturation.

III. Production

The production medium contains:

|  |  |
|---|---|
| Casein hydrolysate | 20 g/l |
| Yeast extract | 10 g/l |
| K$_2$HPO$_4$ | 2.5 g/l |
| MgSo$_4$ · 7H$_2$O | 1 g/l |
| NaCl | 5 g/l |
| Biotin | 0.1 mg/l |
| Thiamine | 1 mg/l |
| Trace elements solution | 3 ml/l |
| CuSO$_4$ | 0.8 g/l |
| ZnSO$_4$ | 10 mg/l |

The medium also contains 12.5 mg/liter tetracycline. The tetracycline is optional for production, but is always found in the medium used for growing the inoculum.

Biotin, thiamine and tetracycline in concentrated solution were filter sterilized separately and added to the sterile production medium before inoculation. Sterile glucose solution was added initially to supply 10 g/l. At the induction step another 10 g/l of glucose was added.

The trace elements solution contains:

|  |  |
|---|---|
| FeCl$_3$ | 16 g/l |
| ZnCl$_2$ · 4H$_2$O | 2 g/l |

| -continued | |
|---|---|
| CoCl$_2$ · 6H$_2$O | 2 g/l |
| Na$_2$MoO$_4$ · 2H$_2$O | 2 g/l |
| CaCl$_2$ · 2H$_2$O | 1 g/l |
| CuCl$_2$ | 1 g/l |
| H$_3$BO$_3$ | 0.5 g/l |
| Conc. HCl | 100 ml/l |

The medium is inoculated with 0.5–10% inoculum culture and incubated at 30° C. Agitation-aeration rates are set to maintain a dissolved oxygen level above 20% air saturation. The pH is maintained at 7±0.2 with NH$_3$. Once cell concentration reaches about 3.5 g/l (OD$_{660}$=10) induction is started.

The temperature is raised to 42° C. and maintained at 42° C. for 1–5 hours. The culture is then chilled and cells are recovered by centrifugation for enzyme purification.

Recovery Of SOD

One and one-half kilograms of bacterial cells (wet cake) are suspended in 12 liters of 50 mM sodium phosphate (pH 7.8), in a Polytron (Kinematica) blender while controlling the speed to minimize foaming. The homogeneous suspension is continuously passed through a Dynomill cell disrupter KD5 (Willy, A. Bachofen, Basel). The homogeneous suspension of disrupted cells is sonicated using a continuous flow cell and centrifuged in a CEPA 101 centrifuge. The supernatant is heated for 2 hours at 65° C., cooled and centrifuged as before. The clear supernatant is concentrated to 1 liter in a Millipore Pellicon ultrafiltration device using 10,000 molecular weight cutoff cassettes (type PTGC). The concentrated protein solution is passed through a DEAE-Sepharose column (2 Kg DEAE Sepharose) equilibrated with 150 mM sodium phosphate buffer (pH 7.8). The flow through solution is collected, concentrated and dialyzed in a Pellicon ultrafiltration device against 20 mM Tris-HCl, pH 7.8, and then applied on to a QAE-Sepharose column equilibrated with 20 mM Tris-HCl buffer. The column is developed with a 20 mM Tris HCl buffer, pH 7.8, and a salt gradient (0–200 mM NaCl). SOD-containing fractions are collected, concentrated using a Pellicon ultrafiltration device, dialzed against distilled water and then brought to 100 mM sodium acetate by adding 1M sodium acetate buffer, pH 4.8. The protein solution is then further separated on a CM-Sepharose column equilibrated with 100 mM sodium acetate buffer, pH 4.7. The column is developed using the same buffer and a salt gradient (100–500 mM NaCl). SOD containing fractions are collected, concentrated using a Pellicon ultrafilter device and lyophilized.

EXAMPLE 8

Activity Of SOD Produced By pSODβ$_1$TT-1

The enzymatic activity of the SOD analog produced by pSODβ$_1$TT-1 prepared in Example 7 was assayed by monitoring the inhibition of reduction of ferricytochrome-c as described by McCord and Fridovich, J. Biol. Chem. (1969), 244, 6049–6055. The results demonstrated that the activity of pSODβ$_1$TT-1-produced SOD analog was comparable to that of natural human SOD and to that of bovine SOD (Orgotein: Grunenthal GMBH).

EXAMPLE 9

Growth of pTV-170

1. Stock Cultures

Stock cultures of pTV-170 were grown on casein medium (see Inoculum), then diluted two-fold with freezing medium and stored at −80° C. Freezing medium contains per 500 ml:

| | |
|---|---|
| $K_2HPO_4$ | 6.3 g |
| $KH_2PO_4$ | 1.8 g |
| Na Citrate | 0.45 g |
| $MgSO_4 \cdot 7H_2O$ | 0.09 g |
| $(NH_4)_2SO_4$ | 0.9 g |
| Glycerol | 44.0 g |

II. Inoculum

The inoculum was propagated in 20 g/l casein hydrolysate, 10 g/l yeast extract and 2 g/l NaCl. Sterile medium in a shake flask was inoculated from stock culture and incubated 15 hours on a shaker at 30° C. and approximately 200 r.p.m. As needed subsequent stages in inoculum propagation were carried out in stirred aerated fermenters. Sterile medium was inoculated with 2–10% innoculum and incubated 15 hours at 30° C., pH 7±0.5 with agitation and aeration to maintain a dissolved oxygen level above 20% air saturation.

III. Production

The production medium contains:

| | |
|---|---|
| Casein hydrolysate | 20 g/l |
| Yeast extract | 10 g/l |
| $K_2HPO_4$ | 2.5 g/l |
| $MgSO_4 \cdot 7H_2O$ | 1 g/l |
| NaCl | 5 g/l |
| Biotin | 0.1 mg/l |
| Thiamine | 1 mg/l |
| Trace elements solution | 3 ml/l |

The medium also contained 100 mg/liter ampicillin. The ampicillin is optional for production but is always found in the medium used for growing the inoculum.

Biotin, thiamine and ampicillin in concentrated solutions were filter sterilized separately and added to the sterile production medium before inoculation. Sterile glucose solution was added initially to supply 10 g/l. At the induction step another 10 g/l of glucose was added.

The trace elements solution contains:

| | |
|---|---|
| $FeCl_3$ | 16 g/l |
| $ZnCl_2 \cdot 4H_2O$ | 2 g/l |
| $CoCl_2 \cdot 6H_2O$ | 2 g/l |
| $Na_2MoO_4 \cdot 2H_2O$ | 2 g/l |
| $CaCl_2 \cdot 2H_2O$ | 1 g/l |
| $CuCl_2$ | 1 g/l |
| $H_3BO_3$ | 0.5 g/l |
| Conc. HCl | 100 ml/l |

The medium is inoculated with 0.5–10% inoculum culture and incubated at 30° C. Agitation-aeration rates are set to maintain dissolved oxygen level above 20% air saturation. The pH is maintained at 7±0.2 with $NH_3$. Once cell concentration reaches about 3.5 g/l ($OD_{660}=10$) induction is started.

The temperature is raised to 42° C. and maintained at 42° C. for 15 minutes. The culture is then chilled and cells are recovered by centrifugation for protein purification.

EXAMPLE 10

Construction of p9200 and Production of bGH Using p9200 in E. coli A1645 and A4255

The construction of p9200 is shown in FIG. 26 and described in the Description of the Figures. pHG44 was cleaved with ClaI and PstI, "filled in" using the Klenow fragment of DNA polymerase I and then the large DNA fragment was isolated. This fragment was ligated to a DNA fragment containing the tetracycline resistance gene of pBR322 which was isolated by cleaving pBR322 with RI and AvaI and then "filling in" using the Klenow fragment of DNA polymerase I. The resulting plasmid p9200 was deposited in the ATCC under Accession Number ATCC 53215.

The plasmid p9200 is similar to pHG44 (FIG. 6) however the plasmid confers tetracycline resistance instead of ampicillin resistance. The plasmid p9200 has been introduced into E. coli strains A1645 and A4255 by transformation using methods known to those of ordinary skill in the art. These strains produced upon growth and induction and analog of bovine growth hormone (bGH) having the amino acid sequence met-asp-gln added to the amino-terminus of the phenylalanine form of the authentic bGH. The amount of bGH analog produced by these strains was roughly equivalent to that produced by pHG44.

The methods used to grow strain A1645/p9200 (host strain A1645 transformed with p9200), recover the bGH analog and purify the bGH analog are identical to that described in Example 5 for pHG44 except that 12.5 mg/l of tetracycline was added instead of 100 mg/l of ampicillin.

The methods used to grow and induce strain A4255/p9200, which has been designated A4320, are described in Example 13. The methods used to purify the bGH analog are identical to those described for pHG44 in Example 5.

The strain A4320 (host strain A4255 transformed with the plasmid p9200) was deposited in the ATCC under Accession Number ATCC 53215.

Replacement of the ampicillin gene with the tetracycline gene is advantageous in that ampicillin can now be eliminated from the production process, thereby eliminating possible contamination of the final product with ampicillin which can cause severe allergic reactions.

EXAMPLE 11

Production of met-leu-leu-leu-met Human ApoE Analog

Plasmid pTVR 279-8 directs expression of a novel apolipoprotein E3 analog. The N-terminal sequence of this analog is met-leu-leu-leu-met followed by the sequence of mature apolipoprotein E3.

Construction of pTVR 279-8

The construction of pTVR 279-8 is shown in FIG. 25 and is described in the Description of the Figures. The plasmid pTVR 279-8 has been deposited in the ATCC under Accession No. 53216.

Plasmid pTV 190 (FIG. 21) was partially digested with AvaI, "filled in" using the klenow fragment of DNA polymerase I, ligated and transformed into E. coli. The resulting plasmid in which the 3' AvaI site had been eliminated, designated pTV 264-45, was digested to completion with NdeI and ligated to the following synthetic oligonucleotides:

```
#1217   5'-TATGCTGCTGCT
#1218       ACGACGACGAAT-5'
```

The resulting plasmid designated pTVR 279-8 was transformed into E. coli A1645 using methods known to those of ordinary skill in the art. Cells containing the plasmid were identified by colony hybridization using $^{32}$P-labelled oligonucleotide No. 1218 as a probe. The identity of the plasmid was confirmed by DNA sequencing. Strain A1645 containing pApoE Ex2 has been deposited in the ATCC under Accession No. 39787.

pTVR 279-8 produces upon growth and induction an analog of human apolipoprotein E3 having the amino acid sequence met-leu-leu-leu-met added to the N-terminus of natural apolipoprotein E3. The methods used to grow the strain are identical to those described for pTV-170 in Example 9 except that the period of induction at 42° C. was 1-5 hours rather than 15 minutes.

pTVR 279-8 produces an ApoE3 analog which is less toxic to the bacteria than the met-ApoE3 analog produced by pTV 170 and pTV 190. The met-leu-leu-leu-met-ApoE3 analog continues to accumulate in the cell even after 60 minutes of induction at 42° C., reaching levels of 400–600 mg/liter culture.

EXAMPLE 12

Production of Human Growth Hormone Analog

Construction of pTV 300

The construction of pTV 300 is shown in FIG. 27 and described in the Description of the Figures. The plasmid was constructed by inserting the hGH gene derived from the plasmid pTV 18(1) into the NdeI site of p579 (FIG. 19). The construction of pTV 18(1) is disclosed in European Patent Publication No. 0 131 843 A1, published Jan. 23, 1985 and also in the corresponding U.S. patent application Ser. No. 514,188, filed Jul. 15, 1983 which is hereby incorporated by reference.

Synthesis of hGH Analog pTV 300 was introduced into *E. coli* strain A1645 by transformation using methods known to those of ordinary skill in the art. This strain produced upon growth and induction an analog of human growth hormone which is deleted of the first 13 amino acids of natural growth hormone. The methods used to grow the strain and purify the hGH analog are identical to those described in Example 5.

EXAMPLE 13

Construction of Prototrophic Strains and Production of bGH Using Prototrophic Hosts Prototrophic strains of *E. coli* have been constructed which enable high level protein expression by many of the previously described plasmids even when grown in a minimal media. The advantages of a bacterial growth protocol using minimal media are:

a) the bacteria can be grown to a higher cell density;

b) it is easier to duplicate growth conditions as the media components are "simpler" and therefore of a higher quality; and c) the media is more economical.

The preferred prototrophic strains of this invention are designated A4200, A4255, and A4346. Strain A4255 containing the plasmid p9200 has been deposited with the ATCC under Accession No. 53215, and is referred to as A4320.

Selection and Construction of the Prototrophic Strains

The following strains were screened for high growth rates on minimal media, and sensitivity to phageλ, λ434 and phage P1:

Strain
1. ATCC 12435
2. ATCC 23716
3. ATCC 27662
4. ATCC 25404
5. ATCC 11775
6. ATCC 25254
7. HfrC=A4134
8. W3350=A2509
9. A1645

Based on results of these studies, we focused the development of a prototrophic strain based on strains ATCC 12435 and ATCC 25404 which were sensitive to the above-listed phage and showed superior growth rates. Using these two strains, we constructed new strains containing the λcI857 repressor by transducing them with P1 containing λcI857 ΔH1 ΔBam H1:Tn10. Tetracycline resistant colonies were purified and cured of P1 if necessary.

The resulting strains and their genotypes are:

A4200=ATCC 12435 (λcI857 ΔH1 ΔBam H1):Tn10

A4206=ATCC 25404 (λcI857 ΔH1 ΔBam H1):Tn10

Both strains were transformed with pHG44 yielding strains A4202 and A4207 respectively.

Growth and Induction

Strains A4202 and A4207 were grown and induced under the following conditions and assayed for production of bovine growth hormone analog.

Media

| Component | Concentration |
|---|---|
| $KH_2PO_4$ | 13.6 gm/liter |
| $(NH_4)_2SO_4$ | 2 gm/liter |
| $MgSO_4 \cdot 7H_2O$ | 0.2 gm/liter |
| $CaCl_2$ | 0.01 gm/liter |
| $FeSO_4 \cdot 7H_2O$ | 0.5 g/liter |
| pH 7.4 | |

| Supplements | |
|---|---|
| Glucose 20% solution | 25 ml/liter |
| Ampicillin 20 mg/ml solution | 1 ml/liter |
| B1 0.3% solution | 1 ml/liter |
| Biotin 0.3% solution | 1 ml/liter |

Both A4202 and A4207 grow well in minimal media; however, only A4202 expresses significant levels of the bGH analog. A4202 expresses the bGH analog at roughly the same level as pHG44 grown in rich media as described in Example 5.

Elimination of Tetracycline Resistance From A4200

In order to utilize the prototrophic strain A4200 with plasmids carrying only a tetracycline resistance marker, we constructed a strain cured of the Tn10 marker. Strain A4200 was streaked on MacConkey galactose plates, gal$^+$ revertants were selected and tested for sensitivity to tetracycline and immunity to lambda phage. This strain was designated A4255.

Construction of Biotin Independent Prototrophic Strains

All of the above prototrophic strains contain the lambda cI857 delta H1 delta Bam H1 defective prophage. The delta H1 deletion extends to the bio uvr B region, removing the biotin biosynthetic operons. Thus the strains require the addition of biotin to the growth media.

To eliminate the biotin requirement of strains derived from A4200 and A4255, we have introduced an F' episome from strain A89 into these strains.

Strain A89 carries an F' gal plasmid. We have demonstrated that this F' plasmid carries all the genes necessary for the endogenous synthesis of biotin. Several properties make this plasmid a convenient source of the bio operons:

1. F' gal is a unit copy plasmid.
2. The plasmid is extremely stable in *E. coli*.
3. F' plasmids are compatible with colE1 plasmid, on which our expression vectors are based.
4. F' gal is a conjugative plasmid. It can, therefore, be easily transferred from cell to cell.
5. One can easily screen for biotin independent strain.

Strain A4202 was conjugated for 30 minutes with A89, and biotin independent colonies were selected. The resulting strain A4346 yields high levels of bovine growth hormone analog following induction in minimal glucose medium in the absence of biotin. No other growth factor is required.

A4346 can be cured of pHG44 using standard methods known to those skilled in the art. The resulting prototrophic host strain can be transformed by all the plasmids described in this application.

Minimal Media

The minimal media standardly used for production purposes with the prototrophic strains was:

|  | For Fermenters | For Shake Flasks |
|---|---|---|
| $K_2HPO_4$ | 6 g/l | 6 g/l |
| $KH_2PO_4$ | 4 g/l | 4 g/l |
| $NH_4Cl$ | 1 g/l | 1 g/l |
| $MgSO_4 \cdot 7H_2O$ | 3 g/l | 0.2 g/l |
| 10% $FeNH_4$ Citrate | 0.3 ml/l | 0.1 ml/l |
| Trace Elements Solution | 3 ml/l | 1 ml/l |
| Antifoam, Silicone Autoclave. | 0.5 ml/l |  |

Ampicillin (100 mg/l) or tetracycline (12.5 mg/l) may be added to the media depending on whether the strain is ampicillin or tetracycline resistant, respectively.

50% glucose was autoclaved separately and added to 20 gm/l. 50% glucose was fed during the fermentation at a rate of approximately 1.08 gm/glucose per O.D. unit for strains without the F' episome, or at a rate of 1.8 gm/glucose per 2.0 unit for strain A4346. The pH was controlled by feeding 25% $NH_4$. Antifoam was added as needed. Biotin was added at 15 mg/l for strains based on A4200, A4255 and A4206.

The trace elements solution contains (Biotechnol. Bioeng. 16:933–941 (1974)):

|  | g/l |
|---|---|
| $H_3BO_3$ | 0.57 |
| $CuCl_2$ ($CuSO_4 \cdot 5H_2O$) | 1.0 (0.04) |
| $CaCl_2 \cdot 2H_2O$ | 1.0 |
| $MnSO_4 \cdot 4H_2O$ | 0.81 |
| $Na_2MoO_4 \cdot 2H_2O$ | 2.0 |
| $CaCl_2 \cdot 6H_2O$ | 2.0 |
| $ZnCl_2 \cdot 4H_2O$ ($ZnSO_4 \cdot 7H_2O$) | 2.0 (2.78) |
| Concentrated HCl | 100 ml |

The compounds in parenthesis are alternate compounds which may be used in place of the compounds preceding them. The parenthesized amounts refer to appropriate amounts of such alternative compounds. Many of the previously described plasmids have been introduced into the prototrophs A4200 and A4255. A partial list of these strains is described in table III below:

TABLE III

| Strain Designation |  | Host Strain/Plasmid |
|---|---|---|
| A4202 | = | A4200/pHG44 |
| A4256 | = | A4255/pHG44 |
| A4320 | = | A4255/p9200 |
| Z1803 | = | A4255/pSODβ₁T11 |
| A4500 | = | A4255/pTV 194 |
| A4346 | = | A4200/pHG44, F'Gal |

EXAMPLE 14

Construction of Lytic Hosts and Production of bGH Using These Lytic Hosts

1. Construction of Strains A4048 and A3111

The strain W3350 has been used extensively for growing phage lambda (see, for example, Oppenheim and Salomon (1970), 41 Virology, 151–159). Strain A2509, a prototrophic derivative of W3350, was transduced by P1cIts grown on A1637, and also transduced with a λcI857 ΔH1ΔBam H1 defective prophage carrying the Tn10 marker. The resulting strain A4048 was selected as a tetracycline resistant clone carrying the defective prophage λcI857Δ H1 ΔBam H1. This strain also carried a P1cIts plasmid. This strain was transformed by pHG44 to yield strain A3111.

Similarly, strain A4085 was also constructed from A2509 by the insertion of λcI857 ΔH1 ΔBam H1, the removal of the Tn10 transposon and the curing of the P1cIts plasmid prior to transformation with pHG44. Strain A4085 carries the defective prophage λcI857 ΔH1 ΔBam H1 and serves as a control for measuring bGH production and the autolysis affected without the presence of the P1 plasmid. Strain A3111 has been deposited in the ATCC under Accession No. 53217.

2. Synthesis of Bovine Growth Hormone (bGH)

Stock Cultures: Stock cultures of strain A3111 (pHG44 in A4048 cells) were grown overnight at 30° C. in LB medium containing 50 µg/ml ampicillin (Amp). The cultures were diluted two-fold with 50% glycerol and stored at −20° C.

Inoculum: The inoculum was obtained from a single colony of A3111 grown on an LB agar plate containing 100µ g/ml Amp. The LB plates, in turn, were spread with material taken from the stock cultures.

Sterile 3 ml LB medium containing 50 µg/ml Amp was inoculated with a single colony of A3111 and grown for 18 hours at 30° C. in a shaker bath.

Production: Production of bGH was carried out in BHI medium (37 µg/l brain heart infustion (Difco)) containing 50

μg/ml Amp. The inoculum was diluted 1:100 into a flask containing fresh BHI+50 μg/ml Amp, and grown in a shaker bath at 30° C. until the cell concentration reached about $4\times10^8$ cells/ml ($OD_{600}$=0.5).

For the induction of bGH production, the flask was transferred to a shaker bath set at 42° C. Cell samples were taken at time 0 and at 90 minutes after the beginning of induction.

Analysis of bGH Production: bGH production was analyzed on a 10–26% gradient acrylamide gel. The cell samples were spun in a microfuge, the supernatant was removed, and the pellets were dissolved in sample buffers (2% SDS, 50 mM Tris pH 7.0, 3% sucrose, 5% β-Mercaptoethanol) and loaded on the gel. After electrophoresis at 200 volts for 2½ hours, the gels were stained with Coomassie blue and the amount of bGH was determined by scanning with a gel scanner.

After 90 minutes of induction at 42° C., bGH comprises about 20% of the total protein of A3111.

3. Autolysis

Strain A3111 carries pHG44, the defective prophage λcI857 ΔH1 ΔBam H1, and a stable P1cIts plasmid. After prolonged induction at 42° C., the cells will start to lyse due to the production of endolysin directed by P1. Complete lysis of the culture was achieved after 2.5–3 hrs.

Test of Controlled Autolysis: 5 ml of A3111 culture were taken before and after induction at 42° C. (90 min.) and spun down in a Sorvall centrifuge at 7000 rpm for 7 minutes. The supernatants were removed and the pellets were frozen at −20° C. overnight. The pellets were then resuspended in 0.5 ml of T.E. buffer (10 mM Tris pH 8.0, 1 mM EDTA) and 0.1 ml was diluted 1:10 with T.E. and the $OD_{600}$ determined.

As a control for this experiment we used strain A4085 which, similarly to A3111, contains pHG44 and the defective prophage λcI857 ΔH1 ΔBam H1 but does not carry the P1cIts plasmid.

The results of such an experiment appear in Table V which shows that cells containing the P1cIts plasmid (A3111) lyse immediately upon thawing. Inspection of the thawed mixture revealed that over 95% of the cells were lysed following this treatment.

TABLE IV

| Strain | P1cIts | $OD_{600}$ Before Freezing | After Thawing | % Loss |
|---|---|---|---|---|
| A4085 | − | 0.980 | 0.851 | 14 |
| A3111 | + | 0.543 | 0.08 | 86 |

The lysis procedure simplifies the extraction of bGH from the induced cells without affecting bGH production.

EXAMPLE 15

Biological Activity of the Met-ApoE3 Analog

Bacteria pTV 194-80 were grown as described in Example 9.

The numbers in parenthesis refer to the references found at the end of this example.

Analysis of Bacterial Extracts

Bacterial cells were harvested by centrifugation and suspended in 50 mM potassium phosphate buffer, pH 7.5, containing 5 mM EDTA and 2 mM phenylmethyl sulfonyl fluoride. Aliquots were lysed in 1.5×sample buffer (15% glycerol, 4.5% NaDodSO, 1 mM B-mercaptoethanol, 93.5 mM Tris.HCl, 0.25% Bromophenol blue, pH 6.8), heated at 100° C. for 10 minutes and proteins analyzed on 10% NaDodSO4 polyacrylamide gels (26). Proteins separated on polyacrylamide gels were either stained with Coomassie brilliant blue or were electrophoretically transferred to nitrocellulose sheets (27) and reacted with $^{125}$I-labeled anti-human ApoE monoclonal or polyclonal IgG. The immunoblots were washed, air dried and exposed to X-ray film.

Isolation of ApoE

Authentic ApoE was isolated from the d<1.02 plasma lipoproteins of a hypertriglyceridemic subject (E3/3 phenotype) by Sephacryl S-300 column chromatography as previously described (14). The E3 isoform was obtained by preparative Immobiline isoelectric focusing (LKB Instruments, Bromma, Sweden, pH range 4.9 to 5.9) (28).

The ApoE analog was isolated from 33 g of lyophilized cells, which represented the cell mass from a five liter fermentation. The cells were ground to a fine powder with the aid of 22 g of alumina (Buehler Ltd., Evanston, Ill.) in a chilled (4°) mortar and pestle. The ground cells were extracted with 300 ml 6M urea (freshly deionized), containing 0.1 M $NH_4HCO_3$, 2 mM PMSF, 0.1% Trasylol (Mobay Chemical Corp., New York, N.Y.) (pH 7.8). The insoluble cellular residue was sedimented by ultracentrifugation at 4° in a Beckman SW28 rotor (25,000 rpm for 50 minutes) and reextracted with 200 ml of 6M urea buffer. The combined supernatant fractions were dialyzed against three changes of 2M urea, containing 25 mM $NH_4HCO_3$, 2 mM PMSF, 2 mM EDTA, 0.1% Trasylol, 0.1% β-mercaptoethanol (pH 7.4). Following dialysis, the extract supernatant was added to ~200 ml heparin-Sepharose, which was prepared as described (29) and equilibrated with the 2M urea buffer. The gel-supernatant mixture was incubated overnight at 4° on a rotating platform and then packed into a glass column (4.0×3.5 cm, Kontes Glass, Vineland, N.J.). The material not bound to the heparin-Sepharose was washed from the column by pumping ~300 ml of 2M urea buffer at a rate of 25 ml/h through the column. The bound material was then eluted from the column with 50 ml of 1.0M $NH_4HCO_3$ in 2M urea and then dialyzed against 5 mM $NH_4HCO_3$ and lyophilized. This semi-purified ApoE was solubilized in 15 ml 6M guanidine, containing 0.1M Tris.HCl, 1 mM EDTA, 1.0% β-mercaptoethanol (pH 7.4) and applied to a Sephacryl S-300 (Pharmacia Fine Chemicals, Uppsala, Sweden) column (2.5×300 cm), equilibrated with 4M guanidine, 0.1M Tris.HCl, 1 mM EDTA, 0.1% β-mercaptoethanol (pH 7.4). The fractions containing ApoE were pooled, exhaustively dialyzed against 5 mM $NH_4HCO_3$ and lyophilized. Final purification was accomplished by preparative isoelectric focusing on an immobiline gel (28).

Structural Characterization of the ApoE Analog

Protein or peptide samples for amino acid analysis were hydrolyzed in 6N HCl for 20 h at 110° C. in sealed, evacuated tubes. Analyses were performed on a Beckman 121 MB Analyzer equipped with a model 126 Data System.

Peptides for amino acid and sequence analyses were generated by digesting 3 mg of Sephacryl S-300 column-purified ApoE with 90 mg CNBr in 600 μl 70% HCOOH for 30 h at room temperature. Resultant peptides were separated on a Sephadex G-50 column as previously described for authentic ApoE (4).

Sequence analyses were performed on an updated Beckman 890C Sequencer using a standard 0.1M Quadrol program. The intact protein was degraded in the presence of 3 mg polybrene and 0.5% NaDodSO$_4$; peptides were degraded in the presence of polybrene only. Phenylthiohydantoin amino acids were identified and quantified by high performance liquid chromatography as previously described (14).

Analytical isoelectric focusing and NaDodSO$_4$ polyacrylamide gel electrophoresis were performed (14). Charge modification with cysteamine (β-mercaptoethanolamine) was done (14).

Biological Characterization of the ApoE Analog

Phospholipid complexes of ApoE analog and dimyristoylphosphatidylcholine (DMPC) were prepared and isolated as previously described (30). Lipoprotein receptor binding assays were performed as described for fibroblasts (31) and hepatic membranes (32). Iodinations of ApoE were performed in 0.10M NH$_4$HCO$_3$ with Iodo-Beads (Pierce) according to manufacturer's directions.

For rabbit and rat in vivo studies, iodinated authentic and ApoE analog (90 μg each) were incubated for 30 minutes at room temperature with 1 ml of rabbit or rat plasma prior to injection into male New Zealand white rabbits. Plasma radioactivity is reported as TCA-precipitable protein using the precipitation method previously described (33). Calculation of the percentage of the injected dose remaining in plasma at the various time intervals was based on a plasma volume estimate of 4.5% of the body mass.

Results and Discussion

Expression of Human ApoE

Following induction of cells transfected with pTV 194-80, a protein with an apparent molecular weight identical to that of ApoE was specifically induced. This induced protein reacted with anti-human ApoE antibodies (not shown).

With induction periods of 30 minutes or longer, lysis of the cells was observed (FIG. 28). This cell lysis was associated with the intracellular accumulation of ApoE. Noninduced cells maintained at 30° C. were stable (FIG. 28). This cellular toxicity lysis was not a general feature of this expression vector as this same expression system containing a human growth hormone cDNA did not show this effect. ApoE was destroyed by proteolysis following cell lysis. The problem of toxicity caused by ApoE accumulation was overcome by inducing the cells for short periods of time (~20 minutes) and then cooling the cells by addition of ice to the fermenter.

As determined by solid-phase radioimmunoassay, the ApoE levels in cells induced for short periods of time were approximately 1% of soluble cellular protein. The ApoE was isolated and purified from cell extracts by heparin-Sepharose and Sephacryl S-300 chromatography. This two-step process resulted in an ApoE preparation that was greater than 90% pure, with a yield representing approximately 20% of the ApoE present in the cell extract. Final purification for characterization was accomplished by the preparative immobiline isoelectric focusing. The purification scheme used in these studies was not optimized for total recovery but, rather, was designed to obtain pure material for characterization.

Structural Characterization of the ApoE Analog

The Immobiline-purified ApoE analog migrated as a single band on SDS gels with an apparent M$_r$ identical to that of authentic ApoE. On isoelectric focusing gels the bioengineered ApoE focused as one major band with a pI identical to that of Immobiline-purified ApoE3. Consistent with the presence of one residue of cysteine, the ApoE analog was shifted one charge unit toward the anode after cysteamine modification. Amino acid analysis of the Immobiline-purified product was compared to authentic human ApoE3 purified by the same method. As shown in Table VI, the analyses of the ApoE analog and authentic ApoE were nearly identical to each other and to the theoretical composition derived from previous sequence analysis of human ApoE. The analyses suggested, however, that the ApoE analog product contained an additional residue of methionine compared to the authentic ApoE. In addition, the presence of one cysteine residue, suggested by cysteamine treatment, was confirmed.

Sequence analysis of the intact ApoE analog (ca. 6 nmole) demonstrated that the extra methionine residue was at the NH$_2$-terminus of the protein and yielded a single sequence of Met-Lys-Val-Glu-Gln-Ala-Val-Glu-Thr-Glu-Pro-Glu-Pro-Glu-Leu-Arg-Gln-Gln-. The sequence following the methionine corresponds to residues 1–17 of human ApoE. These results established that the synthetic oligonucleotide used to reconstruct the NH$_2$-terminal coding portion of ApoE was correctly translated and that the extra methionine (whose codon was added for bacterial translation initiation) was not removed by any processing mechanism. The initial yield in the sequence analysis was unexpectedly low (ca. 20%), but this was probably not due to a portion of the NH$_2$-terminal methionine being formylated, because the formylated protein would have a pI distinctly different from the non-formylated polypeptide (and from authentic ApoE) and this was not observed.

Several of the CNBr peptides were characterized as to their amino acid compositions and were found to be no different from those of authentic ApoE (not shown). In addition, sequence analysis of CB4 (residues 109–125 in authentic ApoE) and partial sequence analysis of CB5 (through the residue corresponding to position 164 in ApoE) established that the sequence of the ApoE analog was identical to authentic ApoE3 in the crucial receptor binding domain. All these data indicated that, except for the additional methionine at the NH$_2$-terminus, the ApoE analog was identical in structure to authentic ApoE3.

In Vitro and In Vivo Metabolic Characterication of the ApoE Analog

Comparison of the receptor binding of ApoE.DMPC complexes demonstrated that the ApoE analog possessed binding properties essentially identical to those of authentic ApoE. In competition studies using $^{125}$I-LDL bound to ApoB, E (LDL) receptors on cultured fibroblasts, the 50% displacement concentration for the ApoE analog was 0.019 μg/ml compared to 0.024 μg/ml for authentic ApoE (FIG. 29). In direct binding studies to fibroblasts both ApoE preparation bound in a similar manner (FIG. 29). Scatchard analysis of the direct binding data revealed that the Kds and maximum amount bound for bioengineered and authentic ApoE were 0.93 and 0.96×10$^{-10}$M and 29.4 and 34.2 μg/mg of cell protein, respectively. In addition, both ApoE preparations also bound similarly and effectively to ApoE receptors on canine hepatic membranes (FIG. 30).

Comparison of the in vivo metabolic properties of the ApoE analog and authentic ApoE also demonstrated that both preparations behaved in an identical manner. When $^{131}$I-ApoE analog and $^{125}$I-authentic ApoE were mixed and incubated with normal rabbit plasma and then the mixture injected into a normal rabbit, both labels were removed from circulation with identical kinetics (FIG. 31). Clearance of 50% of the injected dose of both labels occurred at approximately 20 minutes after the injection. Identical results were obtained with reciprocally labeled proteins and also when turnover studies were done in rats (not shown). Thus, in both in vitro and in vivo studies, the bioengineered and authentic ApoE exhibited similar properties and behaved in essentially identical manners.

In summary, structural characterization of the isolated ApoE analog demonstrated that with the exception of an additional methionine residue at the amino terminus the structure of the ApoE analog was identical to authentic ApoE. In addition, both the in vitro and in vivo metabolic properties of the ApoE analog and authentic ApoE were identical.

TABLE V

Amino Acid Composition of the ApoE Analog and Authentic ApoE3[1]

|  | ApoE3 Analog | Authentic ApoE3 | ApoE3 Sequence |
|---|---|---|---|
| Lys | 12.1 | 12.0 | 12 |
| His | 2.0 | 2.0 | 2 |
| Arg | 33.3 | 33.3 | 34 |
| Cys | 0.8 | 0.8 | 1 |
| Asp | 12.3 | 12.4 | 12 |
| Thr | 10.5 | 10.5 | 11 |
| Ser | 12.7 | 12.6 | 14 |
| Glu | 72.0 | 71.9 | 71 |
| Pro | 8.5 | 8.4 | 8 |
| Gly | 17.3 | 17.3 | 17 |
| Ala | 35.6 | 35.5 | 35 |
| Val | 21.9 | 22.3 | 22 |
| Met | 7.7 | 6.5 | 7 |
| Ile | 1.9 | 1.9 | 2 |
| Leu | 37.0 | 37.3 | 37 |
| Tyr | 3.8 | 3.9 | 4 |
| Phe | 3.2 | 3.2 | 3 |
| Trp | n. d. | n. d. | 7 |

[1]Results are from duplicate determinations and are expressed as residues per mole. Cysteine was determined separately after performic acid oxidation. Threonine and serine values were not corrected for hydrolytic loss. Tryptophan was not determined. ApoE3 sequence is from reference 4.

BIBLIOGRAPHY

1. Mahley R. W. (1978) in *Disturbances in Lipid and Lipoprotein Metabolism*, eds. Dietschy J. M., Gotto A. M. Jr. and Ontko J. A. (American Physiological Society, Bethesda, Md.), pp. 181–197.
2. Mahley R. W., Innerarity T. L., Rall S. C. Jr. & Weisgraber K. H. (1984) *J. Lipid Res*. 25, 1277–1294.
3. Mahley R. W. & Innerarity T. L. (1983) *Biochim. Biophys. Acta* 737, 197–222.
4. Rall S. C., Jr., Weisgraber K. H. and Mahley R. W. (1982) *J. Biol. Chem*. 257, 4171–4178.
5. McLean J. W., Elshourbagy N. A., Chang D. J., Mahley R. W. and Taylor J. M. (1984) *J. Biol. Chem*. 259, 6498–6504.
6. Olaisen B., Teisberg P. and Gedde-Dahl T. Jr. (1982) *Hum. Genet*. 62, 233–236.
7. Paik Y. K., Chang D. J., Reardon C. A., Davies G. E., Mahley R. W. and Taylor J. M. *Proc. Natl. Acad. Sci. USA*, in press.
8. Utermann G., Langenbeck U., Beisiegel U. and Weber W. (1980) *Am. J. Hum. Genet*. 32, 339–347.
9. Zannis V. I. and Breslow J. L. (1981) *Biochemistry* 20, 1033–1041.
10. Zannis V. I., Breslow J. L., Utermann G., Manley R. W., Weisgraber K. H., Havel R. J., Goldstein J. L., Brown M. S., Schonfeld G., Hazzard W. R., Blum C. (1982) *J. Lipid Res*. 23, 911–914.
11. Utermann G., Steinmetz A. and Weber W. (1982) *Hum. Genet*. 60, 344–351.
12. Havel R. J. (1982) *Med. Clin. North Am*. 66, 441–454.
13. Menzel H. J., Kladetzky R. G. and Assmann G. (1983) *J. Biol. Chem*. 256, 9077–d9083.
14. Weisgraber K. H., et al., (1981) *J. Biol. Chem*. 256, 9077–9083.
15. Rall S. C. Jr., Weisgraber K. H., Innerarity T. L. and Mahley R. W. (1982) *Proc. Natl. Acad. Sci. USA* 79, 4696–4700.
16. Rall S. C. Jr., Weisgraber K. H., Innerarity T. L., Mahley R. W. and Assmann G. (1983) *J. Clin. Invest*. 71, 1023–1031.
17. Weisgraber K. H., Rall S. C. Jr., Innerarity T. L., Mahley R. W., Kuusi T. and Ehnholm C. (1984) *J. Clin. Invest*. 73, 1024–1033.
19. Mahley R. W., Innerarity T. L., Rall S. C. Jr. and Weisgraber K. H. *Ann. NY Acad. Sci.*, in press.
20. Innerarity T. L., Friedlander E. J., Rall S. C. Jr., Weisgraber K. H. and Mahley R. W. (1983) *J. Biol. Chem*. 258, 12341–12347.
20a. Innerarity T. L., Weisgraber K. H., Arnold K. S., Rall S. C. Jr. and Mahley R. W. (1984) *J. Biol. Chem*. 259, 7261–7267.
21. Weisgraber K. H., Innerarity T. L., Harder K. J., Mahley R. W., Milne R. W., Marcel Y. L. and Sparrow J. T. (1983) *J. Biol. Chem*. 258, 12348–12354.
26. Laemmli U. K. (1970). *Nature* (London) 227:680–685.
27. Towbin H., Staehelin T. and Gordon J. (1979). *Proc. Natl. Acad. Sci. USA* 148:107–127.
28. Manzel. H. J., et al., (1984) *J. Biol. Chem*. 254: 3070–3076 (1984).
29. Weisgraber K. H. and Mahley R. W. (1980) *J. Lipid Res*. 21, 316–325.
30. Innerarity T. L., Pitas R. E. and Mahley R. W. (1979) *J. Biol. Chem*. 254, 4186–4190.
31. Innerarity T. L. and Mahley R. W. (1978) *Biochemistry* 17, 1440–1447.
32. Hui D. Y., Innerarity T. L. and Mahley R. W. (1981) *J. Biol. Chem*. 256, 5646–5655.
33. Mahley R. W., Innerarity T. L., Weisgraber K. H. and Oh S. Y. (1979) *J. Clin. Invest*. 64, 743–750.

EXAMPLE 16

Biological Activity of the met-asp-gln-bGH Analog

A recent study (P. J. Eppard and D. E. Bauman, Proceedings of 1984 Cornell Nutrition Conference for Feed Manufacturers, pp. 5–12) indicated that continued administration of methionyl-bovine growth hormone over a 12-week period increased milk yields from 10 to 40% as compared with controls. Similar results have been obtained using the met-asp-gln-bGH analog encoded by the pHG44 plasmid upon growth, recovery and purification as described in Example 5.

EXAMPLE 17

Biological Activity of the met-pGH Analog

A recent study (C. A. Spence et al., Abstract entitled "Effect of Exogenous Growth Hormone On Fetal Energy Storage and Lactation Performance in Sows," from The Annual Meeting of The American Society of Animal Science, Univ. of Missouri, Aug. 7–10, 1984) indicate that administration of pituitary-derived porcine growth hormone increases sow lactation and piglet litter survival. In a study of lactation performance, administration of the met-pGH analog to pregnant sows improved sow lactation and piglet litter survival.

EXAMPLE 18

Production of Mutant Forms of the ApoE Gene

The complete ApoE gene which directs the expression of met-leu-leu-leu-met-ApoE together with the cII ribosomal binding site was ligated into an M13mp10 amber vector as shown in FIG. 32. A series of oligodeoxynucleotide-directed mutations was obtained by using the method of Bauer et al., Gene 37: 73–81 (1985). Essentially, the procedure consists of using an M13 vector that contains the cloned target DNA and amber (am) mutations within the phage genes I and II. This vector cannot replicate in a suppressor-free ($sup^o$) strain. A gapped heteroduplex is formed by annealing the complementary (−) strand, digested with EcoRI and BalII, which contains wild-type copies of genes I and II, to the amber mutant containing template (+) strand. The oligonucleotide is annealed to the single-stranded (ss) region and the remaining gaps and nicks are repaired enzymatically to form a closed circular heteroduplex structure (FIG. 32). By transfecting the DNA into a $sup^o$ host the propagation of heteroduplexes with the oligonucleotide-containing (−) strand is promoted, since only this contains the wild-type copies of genes I and II. This procedure eliminates the need for any physical separation of the covalently closed circular DNA containing the mutated DNA from the wild type template. The oligonucleotides used are listed in Table VII.

The mutated pApoE - M13 was then treated in one of two ways. In most cases a partial StuI fragment of the mutated ApoE sequence (containing bp 218 to 766 inclusive corresponding to amino acids 73 to 255 inclusive) was ligated to the large StuI fragment of pTV 194-80 (FIG. 33), or pTV 264-45 (FIG. 41, FIG. 45) or to the (StuI) full-length linear form of PTVR 298-34 (FIGS. 35, 36, 37, 38). (The orientation of the StuI insertion was confirmed by a restriction enzyme digestion.)

In one mutant construction (FIG. 39) the whole mutated ApoE sequence (ECoRI-BglII fragment) was ligated into the large fragment produced by an EcoRI-BglII digestion of pTV 264-45.

These procedures produced plasmids containing mutated forms of ApoE under the control of either the cII or the β lactamase promoter-ribosomal binding site and coding for either met-ApoE or met-leu-leu-leu-met-ApoE, as described in the description of the above figures, and listed in Table VI.

Further mutations were made by transferring ApoE fragments of partial StuI digestions from a plasmid containing a mutated form of ApoE to the large StuI fragment derived from PTVR 289-18. This produces mutated forms of the met-leu-leu-leu-met-ApoE gene under the control of the $\lambda P_L$ promoter and the β lactamase promoter-ribosomal binding site. This is shown in FIGS. 47, 48 and 49.

The rationale for these last constructions is to produce met-leu-leu-leu-met-ApoE mutations (since met-leu-leu-leu-met-ApoE is less toxic to the bacteria than met-ApoE—see Example 11 and Vogel et al., PNAS 82: 8696–8700 (1985) and to have the mutated form of met-leu-leu-leu-met-ApoE under the control of the β lactamase promoter-ribosomal binding site (which directs higher ApoE expression levels than does the cII ribosomal binding site—see Example 4).

One additional mutation (pTHR 526-6) was made by transferring a partial StuI fragment (bp 218–766 inclusive) from a plasmid containing a mutated form of ApoE to the full-length linear form of pTVR 298-34 produced by StuI digestion (FIG. 40). This effectively transferred the mutation from a met-leu-leu-leu-met-ApoE under the control of the cII ribosomal binding site to a met-ApoE under the control of the β lactamase binding site.

An internal deletion mutant was made by removing the internal StuI fragment (bp 218–766 inclusive) of pTV 194-80, and re-ligating (FIG. 34). A deletion mutant (of the N-terminal sequence) was made by constructing through site-directed mutagenesis, an NdeI site at bp 352–357 inclusive, corresponding to amino acids 118 and 119 (FIG. 41). This mutant designated PTHR 324-20 directs expression of an ApoE analog containing histidine and methionine at positions 118 and 119 respectively. Subsequently, NdeI digestion and religation was performed to delete the first 119 amino acids at the N-terminal end of the ApoE sequence, producing the deletion mutant PTHR 501 under the control of the cII ribosomal binding site (FIG. 42). pTHR 501 gave no detectable expression of ApoE analog and so other deletion mutants were constructed which contained met-leu-leu-leu-met at the N-terminus (FIG. 43), or put the deleted ApoE sequence under the control of the beta-lactamase promoter ribosomal binding site (FIG. 44). Both these deletion mutants (pTHR 514-7 and pTHR 520-3 respectively) produced low amounts of ApoE analog protein (Table VI).

The nucleotide sequence at the site of the mutation was confirmed by using Sanger's sequencing method (Sanger, F., Nicklen, S. and Coulson, A. H., PNAS 74: 5463–5467 (1977).) The mutated ApoE fragment was subcloned into M13 vectors (M13 mp 10 and M13 mp 11), and extension of the complementary strand was carried out using either the M13 universal primer or BTG Primer number 2426 specifically designed for sequencing the ApoE mutants. Primer number 2426 is homologous to nucleotides 493–516 inclusive, and its sequence is as follows:

3' - CCC CGG GCG CTC CCG CGG CTC GCG - 5'

TABLE VI

| # | Plasmids Clone # | Mutation Site | Host | Apo-E Aminoterminus and ribosomal binding site met—lys cII | met—lys PBLA | met—leu— leu—leu cII | met—leu— leu—leu PBLA | fused proteins cII | fused proteins PBLA | Primer # | Method of construction | Expressibility | Receptor binding assay (authentic serum Apo-E = 100%) |
|---|---|---|---|---|---|---|---|---|---|---|---|---|---|
| 1 | pApo-E-Ex2 | None | aux | x | | | | | | — | ATCC # 39787 | low | |
| 2 | pYB 288 | 42 aa SOD Apo-E | aux | | | | | | x | — | FIG. 18 | + | |
| 3 | pTV 170 | None | aux | x | | | | | | — | FIG. 20 | + | |
| 4 | pSAL 160-5 | hGH fused Apo-E | aux | | | | | x | | — | FIG. 23 | + | |
| 5 | pTV 190 | None | " | x | | | | | | — | FIG. 21 | + | |
| 6 | pTV 214 | hGH fused Apo-E | " | | | | | x | | — | FIG. 24 | + | |
| 7 | pTV 194-80 | None | " | | x | | | | | — | FIG. 22 | + | 100% |
| 8 | pTVR 264-45 | None | " | x | | | | | | — | FIG. 25 | + | |
| 9 | pTVR 279-8 | None | | | | x | | | | — | FIG. 25 | + | |
| 10 | pTHR315-18 | aa 143 | aux | | x | | | | | 2909 | FIG. 33 | + | |
| | pTHR315-18-26 | lys—>ala | pro | | x | | | | | | | + | 8% |
| 11 | pTVR 298-34 | deletion of aa 73-255 (inc.) | aux | | x | | | | | — | FIG. 34 | + | |
| 12 | pTHR 530-40 | aa 136 arg—>ser | aux | | x | | | | | 2115 | FIG. 35 | + | |
| 13 | pTHR 531-6II | aa 112 cys—>arg | aux | | x | | | | | 2610 | FIG. 36 | + | |
| 14 | pTHR 532-18 | aa 140 his—>ala | aux | | x | | | | | 2910 | FIG. 37 | + | |
| 15 | pTHR 533-4 | aa 150 arg—>ala | | | x | | | | | 3508 | FIG. 38 | + | |
| 16 | pTHR 299-40 | aa 140 | aux | | | x | | | | 3105 | FIG. 39 | + | |
| | pTHR 299-40-16 | leu—>pro | pro | | | x | | | | | | + | 2% |
| 17 | pTHR 526-6 | aa 144 leu—>pro | aux | | x | | | | | — | FIG. 40 | + | |
| 18 | pTHR 324 | aa 118 tyr—>his aa 119 arg—>met | aux | x | | | | | | 2427 | FIG. 41 | | |
| 19 | pTHR 501 | first 119 aa deleted | aux | | x | | | | | — | FIG. 42 | not detectable | |
| 20 | pTHR 514-7 | first 119 aa deleted | aux | | | x | | | | — | FIG. 43 | low | |
| 21 | pTHR 520-3 | first 119 aa deleted | aux | | x | | | | | | FIG. 44 | low | |
| 22 | pTHR 325-22 | aa 139 ser— arg aa 149 leu—>ala | aux | x | | | | | | 5103 | FIG. 45 | + | |
| 23 | pTHR 289-18 | None | aux | | | | x | | | — | FIG. 46 | + | 100% |
| 24 | pTHR 525-2 | aa 139 ser—>arg | aux | | | | x | | | — | FIG. 47 | + | |
| | pTHR 525-2-31 | aa 149 leu—>ala | pro | | | | x | | | | | + | 100% |
| 25 | pTHR 540-37 | aa 112 cys—>arg | aux | | | | x | | | — | FIG. 48 | + | |
| 26 | pTHR 539-5II | aa 140 His—>Ala | aux | | | | x | | | — | FIG. 49 | + | |

Mutated StuI fragment (bp 218–766 inclusive) or whole gene came from mutated plasmid in Figure

TABLE VII

Synthetic Oligonucleotide Primers for Sequencing, Complementary to the Nucleotides Indicated.*

| Primer No. | Residue No. | Amino Acid Change | Synthetic Oligonucleotide Primer |
|---|---|---|---|
| 2115 | 136 | Arg → Ser | 3' CTC GAT GCG CAC AGG GAG CGG - 5'<br>                                    136 |
| 2427 | 118 | Tyr → His<br>**Arg → Met | 3' CAC GTC GTA TAC CCG CTC CAC GTC - 5'<br>                     118 119 |
| 2610 | 112 | Cys → Arg | 3' -C CTC CTG CAC GCG CCG GCG GAC CAC G - 5'<br>                              112 |
| 2909 | 143 | Lys → Ala | 3' -G AGG GTG GAC GCT CGA GAC GCA TTC GCC G - 5'<br>                                143 |
| 2910 | 140 | His → Ala | 3' - CAC GCG GAG CGC TCA CGG GAC GCG TTC GA - 5'<br>                                     140 |
| 3105 | 144 | Leu → Pro | 3' -G GTC GAC GCG TTC GGA TCC TTC GCC GAG GAG - 5'<br>                                  144 |
| 3508 | 150 | Arg → Ala | 3' -C GCC GAG GAG CGG CTA CGG CTA CTA GAC GTC TTC G - 5'<br>                                    150 |
| 5103 | 139 | Ser → Arg<br>Leu → Ala | 3' - GCG GAG CGG GCG GTG GAC GCG TTC GAA GCA TTC GCC GAG CGG GCG CTA CGG - 5'<br>                              139                                              149 |

The first methionine of recombinant Apo-E is counted as minus 1; amino acid number 1 is lysine.
*This creates an NdeI site.

EXAMPLE 19

Expression of the Mutant ApoE Analogs

The mutant ApoE plasmids described in Examnple 42 (Table VI) were introduced in the first instance into *E. coli* strain A1645 by transformation using methods known to those of ordinary skill in the art. The clones obtained were grown as described for pTV-170 (Example 9), except that the bacteria producing met-leu-leu-leu-met-ApoE analogs were induced for 40–60 mins. while the bacteria producing met-ApoE analogs were induced for only 15–20 mins. This is because met-leu-leu-leu-met-ApoE analogs are less toxic to the bacteria than the met-ApoE analogs (see Example 11).

Expression of the ApoE-analog protein was measured as described in Example 12. Cell proteins which had been separated on polyacrylamide gels were either stained with Coomassie brilliant blue or were electrophoretically transferred to nitrocellulose sheets ("Western blots") and reacted with $^{125}$I-labeled anti-human ApoE monoclonal antibodies or polyclonal antibodies. The immunoblots were washed, air dried and exposed to X-ray film. The results of the immunoblots are indicated in Table VI under the heading "Expressibility".

As indicated in Table VI, three of the plasmids (pTHR 315-18, PTHR 299-40, and pTHR 525-2) were transformed into the *E. coli* prototroph A4255, using methods known to those of ordinary skill in the art; the growth conditions and medium used were as described in Example 9. The protrophic bacteria containing the plasmids are identified by an additional number in Table VII (viz pTHR 315-18-26, pTHR 299-40-16 and pTHR 525-2-31. Preliminary results indicate that plasmids pTHR 299-40-16 and pTHR 525-2-31 express a higher level of ApoE analog when in the prototroph than in the auxotroph, whereas the reverse seems to be the case with pTHR 315-18-26.

EXAMPLE 20

Biological Activity of the Mutant Analogs of ApoE

Mutant analogs of ApoE were isolated and purified to homogeneity from bacterial extracts, and lipoprotein receptor binding assays were performed on them as described in Example 15. The results are shown in the final column of Table VI.

These various ApoE mutants will undergo in vitro and in vivo metabolic characterization similar to that described in Example 15 and by Vogel et al., PNAS 82: 8696–8700 (1985), for the characterization of recombinant met-ApoE. The in vitro tests include comparison of the receptor binding properties of ApoE-dimyristoyl phosphatidylcholine (Apo-E.DMPC) complexes to apolipoprotein B, E (LDL) receptors on fibroblasts and to apolipoprotein E receptors on hepatic membranes (competition studies and direct binding studies). The in vivo tests include clearance of iodinated ApoE analogs from rabbit and rat plasma (turnover studies). These analogs may then be used for clinical trials to treat patients with hyperlipoproteinemia, or patients with other disorders related to lipid metabolism.

EXAMPLE 21

Treatment of Alopecia in Adult Dogs with Bovine Growth Hormone Analogs

The numbers in parentheses refer to the references found at the end of this example.

The met-asp-gln-bGH analog was used to treat adult onset growth hormone responsive alopecia in adult dogs. Although adult onset growth hormone responsive alopecia (AOGHRA) (hyposomatotropism) is a relatively rare endocrine skin disease of dogs, insufficient amounts of growth hormone can cause even mature dogs to sustain skin and hair changes similar to those seen in dwarfs. Administration of growth hormone, however, reverses these changes.

The endocrinopathy is characterized by bilaterally symmetric hair loss from the trunk, neck, and proximal tail. Hair on the head and extremities is spared. Neither inflammation nor puritus is present. The skin in alopecic areas is markedly hyperpigmented, thin, and hypotonic. Dry scales are sometimes present. This disease seems similar to hyperadrenocorticism and once was called pseudo-Cushing's syndrome because the hair loss resembles the pattern seen in animals affected by Cushing's disease (1). But none of the systemic signs of illness seen with Cushing's disease are seen with AOGHRA. Most significant is that baseline values and results of stimulation tests of both the adrenal and the thyroid glands of AOGHRA-affected animals are normal.

AOGHRA is refractory to all currently known methods of treatment except injections of growth hormone. To date, bovine (2), porcine (2), and bovine (3) growth hormones have been used.

The met-asp-gln-bGH analog prepared as described in Example 5 was used to treat dogs suffering from AOGHRA.

When treating dogs with this product, five or 10 units are given subcutaneously, every other day, for 10 doses. Smaller dogs, such as Pomeranians and Minature Poodles, receive five units, and larger dogs, such as Chow Chows and Keeshonds, receive 10 units. Because growth hormone can induce diabetes mellitus, blood glucose concentrations should be monitored.

Hair will begin to grow back about three weeks after the final injection, and the coat will return to normal in two months. One series of injections seems to be adequate at this time, and further treatment does not seem necessary after hair regrows.

The following paragraphs describe for example the treatment of one animal with this bGH analog. This example is illustrative of the many experiments performed.

Curing a Dog's AOGHRA with Genetically Engineered Bovine Growth Hormone

A two-year old spayed black chow chow was presented for examination of skin lesions of four month's duration. Bilaterally symmetric alopecia with hyperpigmentation was present on the trunk, neck, rump, tail, and proximal thighs. The remaining hair, having the soft texture of a puppy's coat, epilated easily. A superficial rash characterized by puritus, papules, and pustules was present on the dog's rump; an antibiotic containing trimethoprim and sulfamethoxazole had been prescribed by the referring veterinarian. Only the pustular area over the dog's rump was pruritic. The dog also had fleas. The dog's dam had no dermatologic problems, but, according to the owner, a littermate had "lost some hair." Specific details were not available.

Laboratory examinations results from laboratory tests included: skin scrapings—negative; wood's light—negative; fungal culture—negative; CBC—mild eosinophilia; urinalysis—normal; fecal exam—hookworms; baseline resting $T_3$ and $T_4$—normal.

The tentative diagnosis was an endocrine dermatosis and mild flea-allergy dermatitis with secondary bacterial pyoderma.

The dog was treated with oxacillin sodium capsules at a dose of 10 mg/lb t.i.d. Flea-control procedures were discussed with the client, and flea shampoo, spray, dip and a premise spray were dispensed. A biopsy was scheduled.

Several 6 mm punch biopsy specimens were sent to a veterinary dermatopathologist for evaluation. Histopathologic diagnoses were:

1. Allergic type-one hypersensitivity dermatitis diagnosed from a biopsy specimen taken from the rump of the dog. This suggested flea-allergy dermatitis.
2. Acquired noninflammatory hormonal alopecia, suggestive of hypothyroidism or growth hormone responsive disease.

When biopsy specimens were stained with a special stain for dermal elastin, a moderate decrease in dermal elastin was discovered.

Based on the results of histopathology, a normal thyroid protile, and historical and clinical evidence, a diagnosis of adult onset growth hormone responsive alopecia was established. Ten units of met-asp-gln-bGH were administered subcutaneously every other day for 10 doses. No marked changes occurred in the dog's blood glucose concentrations either before or during the treatment period.

Two months after the first injection of bovine growth hormone, the dog's hair was starting to regrow. Three months after the start of treatment, a full coat had regrown, and at four months, the dog had a luxurious coat typical of its breed. Except for some pruritus associated with fleas (12 months after treatment), the dog is clinically normal with a normal coat.

REFERENCE

1. E. T. Siegel, "Hypofunction of the Anterior Pituitary Gland", *Endocrine Diseases of the Dog* (E. T. Siegel, ed.) Lea & Febiger, Philadelphia, Pa., pp. 23–32 (1977).
2. W. M. Parker, D. W. Scott, "Growth Hormone Responsive Alopecia in the Mature Dog" A Discussion of 13 Cases, JAAHA 16: 824–828 (1980).
3. J. E. Eigenmann, D. F. Patterson, "Growth Hormone Deficiency in the Mature Dog", JAAHA 20: 741–746 (1984).

EXAMPLE 22

Construction of pAs 575

The plasmid pAs 575, shown in FIG. 50 and described in detail under Description of the Figures is composed of $\lambda P_L$ promoter, the N utilization site ($Nut_L$) a cII ribosomal binding site bounded by unique EcoRI and NdeI restriction sites, an ATG initiation codon, a gene encoding pGH and $T_1T_2$ transcription termination signals. Other features, including the ampicillin resistance gene, are shown in FIG. 50.

pAs 575 was constructed by cleaving p4005 with NdeI, isolating the fragment containing the gene for pGH and ligating it to p579 (FIG. 19) cleaved with NdeI.

p4005 may be obtained as described in copending coassigned U.S. patent application Ser. No. 821,830, filed Jan. 23, 1986 which is incorporated herein by reference.

Plasmid pAs 575 may be introduced into *E. coli* by methods known to those of ordinary skill in the art and grown as described in Example 5. This strain produces upon growth and induction an analog of porcine growth hormone (pGH) having a methionine residue at the N-terminus.

The met pGH analog produced is recovered and purified by the methods described in Example 5.

What is claimed is:

1. A plasmid expressing met-asp-gln bovine growth hormone designated p9200 having the restriction map shown in FIG. 26 and deposited in *Escherichia coli* A4255 under ATCC Accession No. 53215.

2. A host plasmid system comprising the plasmid of claim 1 wherein the *E.coli* host is strain A4255, the *E.coli* host plasmid system being deposited as A4320 under ATCC Accession No. 53215.

3. A method for producing met-asp-gln bovine growth hormone which comprises growing a host plasmid system of claim 2 under conditions permitting production of the met-asp-gln bovine growth hormone and recovering the met-asp-gln bovine growth hormone so produced.

* * * * *